(12) United States Patent
Cann et al.

(10) Patent No.: US 10,457,969 B2
(45) Date of Patent: Oct. 29, 2019

(54) POLYNUCLEOTIDE ENRICHMENT USING CRISPR-CAS SYSTEMS

(71) Applicant: Illumina, Inc., San Diego, CA (US)

(72) Inventors: Gordon M. Cann, Redwood City, CA (US); Jeffrey G. Mandell, La Jolla, CA (US); Alex Aravanis, San Mateo, CA (US); Steven Norberg, San Diego, CA (US); Dmitry K. Pokholok, San Marcos, CA (US); Frank J. Steemers, Encinitas, CA (US); Farnaz Absalan, San Francisco, CA (US); Leila Bazargan, Palo Alto, CA (US)

(73) Assignee: Illumina, Inc., San Diego, CA (US)

( * ) Notice: Subject to any disclaimer, the term of this patent is extended or adjusted under 35 U.S.C. 154(b) by 714 days.

(21) Appl. No.: 14/804,068

(22) Filed: Jul. 20, 2015

(65) Prior Publication Data

US 2016/0017396 A1    Jan. 21, 2016

Related U.S. Application Data

(60) Provisional application No. 62/181,084, filed on Jun. 17, 2015, provisional application No. 62/027,191, filed on Jul. 21, 2014.

(51) Int. Cl.
| | | |
|---|---|---|
| *C12P 19/34* | (2006.01) | |
| *C12N 15/10* | (2006.01) | |
| *C12Q 1/6816* | (2018.01) | |
| *C12Q 1/683* | (2018.01) | |
| *C12Q 1/6869* | (2018.01) | |

(52) U.S. Cl.
CPC ............ *C12P 19/34* (2013.01); *C12N 15/102* (2013.01); *C12Q 1/683* (2013.01); *C12Q 1/6816* (2013.01); *C12Q 1/6869* (2013.01); *C12Q 2521/301* (2013.01)

(58) Field of Classification Search
CPC ... C12N 15/102; C12Q 1/6816; C12Q 1/6869
See application file for complete search history.

(56) References Cited

U.S. PATENT DOCUMENTS

| | | |
|---|---|---|
| 2014/0038241 A1 | 2/2014 | Zhou et al. |
| 2014/0356867 A1 | 12/2014 | Peter et al. |
| 2014/0357523 A1 | 12/2014 | Zeiner et al. |

FOREIGN PATENT DOCUMENTS

| | | |
|---|---|---|
| WO | 2011/053987 | 5/2011 |
| WO | 2014/125668 | 8/2014 |
| WO | 2015/075056 | 5/2015 |

OTHER PUBLICATIONS

Fujii, et al., "Isolation of Specific Genomic Regions and Identification of their Associated Molecules by Engineered DNA-Binding Molecule-Mediated Chromatin Imnunoprecipitation (enChIP) Using the CRISPR System and TAL Proteins", International Journal of Molecular Sciences, vol. 16, No. 9. Sep. 9, 2015, pp. 21802-21812.
Fujita, et al., "Efficient isolation of specific genomic regions and identification of associated proteins by engineered DNA-binding molecule-mediated chromatin inmunoprecipitation (enChIP) using CRISPR", Biochemical and Biophysical Research Communications, vol. 439, No. 1, Aug. 11, 2013, pp. 132-136.
Glemzaite, et al., "Targeted gene editing by transfection of in vitro reconstituted *Streptococcus thermophilus* Cas9 nuclease comple", RNA Biology, vol. 12, No. I, 2015, p. 1-4.
Lei, et al., "Repurposing CRISPR as an RNA-Guided Platform for Sequence-Specific Control of Gene Expression", Cell, vol. 152, No. 5, Feb. 1, 2013, pp. 1173-1183.
International Search Report and Written Opinion for PCT Application No. PCT/US2015/041134, dated Oct. 26, 2015, 14 pages.
Schule et al., Parkinson's Disease Associated with Pure ATXN10 repeat expansion, NPJ Parkinson's Disease 2017, 27, 7 pages.
Shin et al., "CRISPR-Cas9-targeted fragmentation and selective sequencing enable massively parallel microsatellite analysis," Nature Communications 2017, 13 pages.

*Primary Examiner* — Antonio Galisteo Gonzalez
(74) *Attorney, Agent, or Firm* — Gavrilovich, Dodd & Lindsey LLP

(57) ABSTRACT

A method for enriching a target nucleic acid comprising providing an endonuclease system having a crRNA or a derivative thereof, and a Cas protein or a variant thereof. The crRNA or the derivative thereof contains a target-specific nucleotide region substantially complementary to a region of the target nucleic acid; contacting the target nucleic acid with the endonuclease system to form a complex; and separating the complex and thereby enriching for the target nucleic acid.

19 Claims, 46 Drawing Sheets

Specification includes a Sequence Listing.

| Lane | Description |
|---|---|
| 1 | Induced Cell Lysate |
| 2 | Cell Extract after His-Tag Purification & TEV Digestion |
| 3 | Ion Exchange Flow-Through |
| 4 | Ion Exchange Eluate |

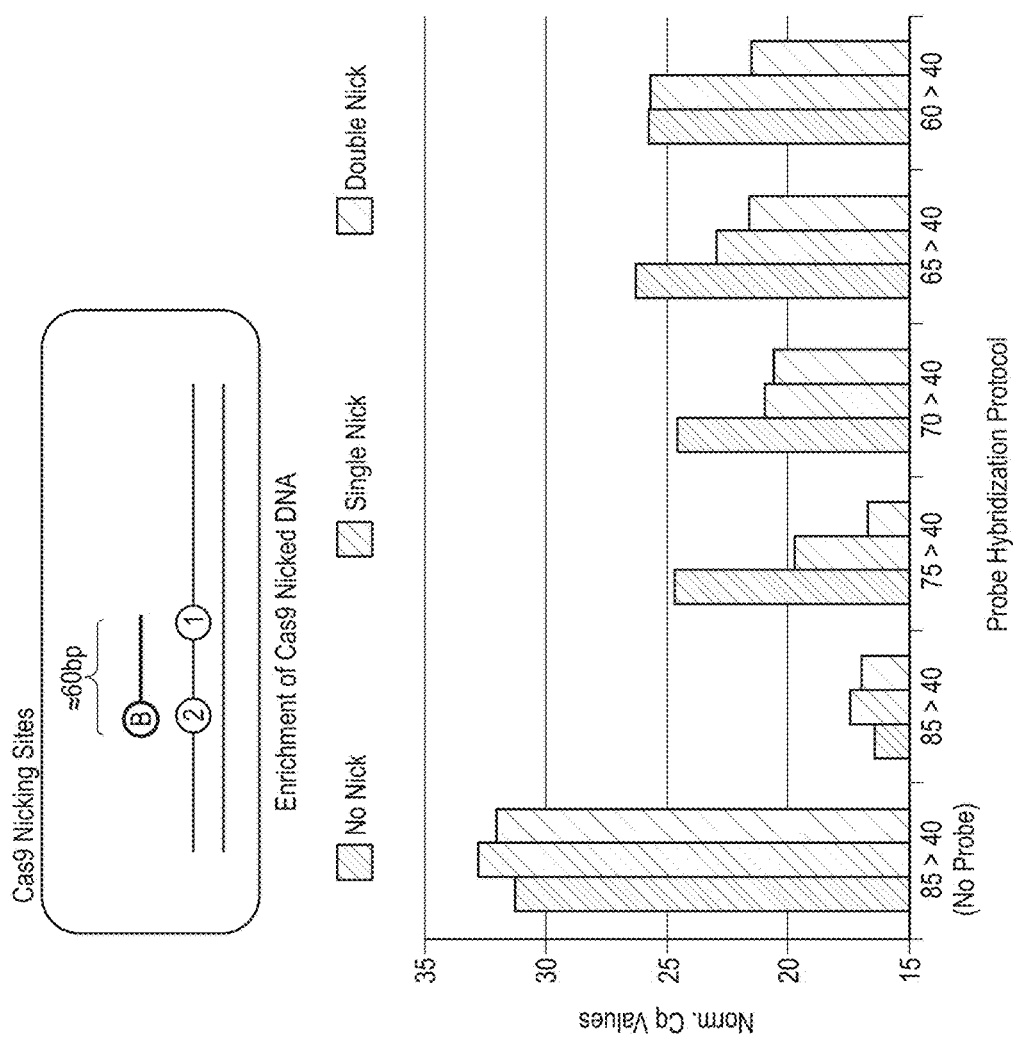

```
                              SEQUENCE LISTING

<160> NUMBER OF SEQ ID NOS: 10

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (36)..(50)
<223> OTHER INFORMATION: a, c, t, g, unknown or other

<400> SEQUENCE: 1
nnnnnnnnnn nnnnntgtac cgctccgctc gctccnnnnn nnnnnnnnnn              50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(15)
<223> OTHER INFORMATION: a, c, t, g, unknown or other
<220> FEATURE:
<221> NAME/KEY: modified_base
<222> LOCATION: (36)..(36)
<223> OTHER INFORMATION: a, c, t, g, unknown or other
<220> FEATURE:
<221> NAME/KEY: modified_base
<222> LOCATION: (39)..(50)
<223> OTHER INFORMATION: a, c, t, g, unknown or other

<400> SEQUENCE: 2
nnnnnnnnnn nnnnnggagc gagcggagcg gtacanggnn nnnnnnnnnn              50

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tgtaccgctc cgctcgctcc                                               20

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: Synthetic
```

```
        oligonucleotide
<220> FEATURE:
<221> NAME/KEY: modified_base
<222> LOCATION: (7)..(11)
<223> OTHER INFORMATION: a, c, t, g, unknown or other

<400> SEQUENCE: 4
ggtctcnnnn n                                                              11

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(8)
<223> OTHER INFORMATION: a, c, t, g, unknown or other
<220> FEATURE:
<221> NAME/KEY: modified_base
<222> LOCATION: (12)..(24)
<223> OTHER INFORMATION: a, c, t, g, unknown or other

<400> SEQUENCE: 5
gagnnnnnct cnnnnnnnnn nnnn                                                24

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acggctgaaa tataccgaag agg                                                 23

<210> SEQ ID NO 7
<211> LENGTH: 42
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
acggcugaaa uauaccgaag guuuuagagc uaugcuguuu ug                            42

<210> SEQ ID NO 8
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
caaaacagca tagctctaaa accttcggta tatttcagcc gtctatagtg agtcgtatta         60
atttc                                                                    65

<210> SEQ ID NO 9
<211> LENGTH: 65
<212> TYPE: DNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 9
gaaattaata cgactcacta tagacggctg aaatataccg aaggttttag agctatgctg    60
ttttg                                                                65

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 10

His His His His His His
1               5
```

POLYNUCLEOTIDE ENRICHMENT USING CRISPR-CAS SYSTEMS

STATEMENT REGARDING FEDERALLY SPONSORED RESEARCH OR DEVELOPMENT

This invention was made with government support under awarded by AI090905 National Institutes of Health. The United States Government has certain rights in the invention.

SEQUENCE LISTING

The instant application contains a Sequence Listing which has been submitted electronically in ASCII format and is hereby incorporated by reference in its entirely. Said ASCII copy created on Aug. 28, 2015, is named IP-1241-US_SL.txt and is 3,623 bytes in size.

The present disclosure relates generally to methods for enriching polynucleotides, and more specifically to methods for enriching polynucleotides using CRISPR-Cas systems and applications thereof.

BACKGROUND

There are a variety of methods and applications for which it is desirable to enrich a target polynucleotide among a population of polynucleotides, e.g., among whole genome. Such methods and applications include, but not limited to, determining existence of a sequence for diagnosing a condition or disease.

Many of the methods currently used for sequence-specific DNA enrichment involve multiple steps and require relatively large amounts of sample nucleic acids, and usually are difficult, tedious, laborious, time-consuming, inefficient, and costly. In addition, methods currently used for targeted enrichment of double-stranded DNA require creating a single-stranded DNA prior to the sequence specific targeting. They also require longer time for hybridizing probes to target DNA. Thus, there exists a need for new methods that enable rapid and efficient sequence-specific polynucleotide enrichment. The present disclosure addresses this need by providing methods for enriching polynucleotide using CRISPR-Cas systems. Related advantages are provided as well.

Clustered regularly interspaced short palindromic repeats (CRISPRs) are involved in an interference pathway that protects cells from bacteriophages and conjugative plasmids in many bacteria and archaea (Marraffini and Sontheimer, 2010, *Nat Rev Genet.* 11(3): 181-190). CRISPR consists of arrays of short repeat sequences interspaced by unique variable DNA sequences of similar size called spacers, which often originate from phage or plasmid DNA (Barrangou et al., 2007, *Science* 315:1709-12; Bolotin et al., 2005, *Microbiology* 151:2551-61; Mojica et al., 2005, *J Mol Evol* 60:174-82). Thus, CRISPR sequences provide an adaptive, heritable record of past infections and express CRISPR RNAs (crRNAs)—small RNAs that target invasive nucleic acids (Marraffini and Sontheimer, 2010, *Nat Rev Genet.* 11(3): 181-190). CRISPRs are often associated with CRISPR-associated (Cas) genes that code for proteins related to CRISPRs. Cas proteins can provide mechanisms for destroying invading foreign nucleic acids targeted by crRNAs. CRISPR together with Cas (CRISPR-associated) genes comprise an adaptive immune system that provides acquired resistance against invading foreign nucleic acids in bacteria and archaea (Barrangou et al., 2007, *Science* 315: 1709-12).

SUMMARY

The present disclosure provides methods for enriching polynucleotides, and more specifically to methods for enriching a target DNA sequence using CRISPR-Cas systems and applications thereof.

In one aspect, provided herein is a method for enriching a target nucleic acid including providing an endonuclease system having: a clustered regularly interspaced short palindromic repeat (CRISPR) RNA (crRNA) or a derivative thereof, and a CRISPR-associated (Cas) protein or a variant thereof, wherein the crRNA or the derivative thereof contains a target-specific nucleotide region complementary to a region of the target nucleic acid; contacting the target nucleic acid with the endonuclease system to form a complex, and separating the complex and thereby enriching for the target nucleic acid.

In some embodiments, the method further includes separating the target nucleic acid from the complex. In some embodiments, the method further includes amplifying the targeted nucleic acid.

In some embodiments, the endonuclease system provided herein further comprises a trans-activating crRNA (tracrRNA) or a derivative thereof. In some embodiments, the crRNA or the derivative thereof is a polynucleotide containing a crRNA polynucleotide fused to a tracrRNA polynucleotide. In some embodiments, the endonuclease system is a Type II CRISPR-Cas system or a derivative thereof. In some embodiments, the target nucleic acid is a double-stranded DNA (dsDNA).

In some embodiments, the endonuclease system is labeled. In some embodiments, the crRNA is labeled with biotin. In some embodiments, the method provided herein further includes adding streptavidin and thereby separating the complex. In some embodiments, the Cas protein or the derivative thereof is labeled with a capture tag.

In some embodiments, one or more of the following Cas9 complex components can be labeled with a binding tag: Cas9 enzyme, crRNA, tracrRNA, and DNA probe targeting the displacement loop. In some embodiments, the binding tag is biotin, or a functional analogue thereof.

In certain embodiments, where the Cas9 enzyme is labeled with a binding tag, the protein can be chemically tagged. For example, Cas9 can be chemically biotinylated. As another example, a fusion can be created by adding additional sequence encoding a fusion to the Cas9 gene. One example of a fusion useful in such embodiments is an AviTag™, which employs a highly targeted enzymatic conjugation of a single biotin on a unique 15 amino acid peptide tag.

In certain embodiments, where crRNA is labeled with a binding tag, the entire crRNA can be labeled using in vitro transcription (IVT) incorporating one or more biotinylated nucleotides, such as, for example biotinylated uracil. In some embodiments, biotin can be chemically or enzymatically added to crRNA, such as, for example, the addition of 2 biotin groups (dual biotin) at the 3' end of crRNA.

In certain embodiments, where tracrRNA is labeled with a binding tag, the entire tracrRNA can be labeled using in vitro transcription (IVT) incorporating one or more biotinylated nucleotides, such as, for example biotinylated uracil. In some embodiments, biotin can be chemically or enzymatically added to tracrRNA, such as, for example, the addition of 2 biotin groups (dual biotin) at the 3' end of tracrRNA.

In certain embodiments, where a probe targeting the displacement loop is labeled with a binding tag, an oligonucleotide having the specific sequence of interest can be synthesized by adding a biotin group at the 5' end of the oligonucleotide probe. For example, one or more biotinylated phosphoramadites can be incorporated into an oligonucleotide during synthesis.

In some embodiments, the Cas protein or the variant thereof is a Cas9 protein or a variant thereof. In some embodiments, the Cas9 protein or the variant thereof retains two nuclease domains and is able to produce a double-stranded DNA break. In some embodiments, the Cas9 protein contains one inactivated nuclease domain comprising a mutation in the domain that cleaves a target nucleic acid strand that is complementary to the crRNA. In some embodiments, said mutation is D10A. In some embodiments, the Cas9 protein contains one inactivated nuclease domain comprising a mutation in the domain that cleaves a target nucleic acid strand that is non-complementary to the crRNA. In some embodiments, said mutation is H840A. In some embodiments, the Cas9 protein contains two inactivated nuclease domains. In some embodiments, the two inactivated nuclease domains comprise a first mutation in the domain that cleaves the strand complementary to the crRNA and a second mutation in the domain that cleaves the strand non-complementary to the crRNA. In some embodiments, said first mutation is D10A and said second mutation is H840A.

In another aspect, provided herein is a method for enriching a target double-stranded nucleic acid including: providing an endonuclease system having: a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of a first strand of the target double-stranded nucleic acid; contacting the target double-stranded nucleic acid with the endonuclease system to form a first complex; hybridizing a labeled nucleic acid to a second strand of the target double-stranded nucleic acid to form a second complex, the second strand of the target double-stranded nucleic acid being non-complementary to the crRNA or the derivative thereof, and separating the second complex and thereby enriching for the target nucleic acid.

In some embodiments, the method further includes separating the target nucleic acid from the complex. In some embodiments, the method further includes amplifying the targeted nucleic acid.

In some embodiments, the endonuclease system provided herein further comprises a trans-activating crRNA (tracrRNA) or a derivative thereof. In some embodiments, the crRNA or the derivative thereof is a polynucleotide comprising a crRNA polynucleotide fused to a tracrRNA polynucleotide. In some embodiments, the endonuclease system is a Type II CRISPR-Cas system or a derivative thereof. In some embodiments, the target nucleic acid is a double-stranded DNA (dsDNA).

In some embodiments, the endonuclease system is labeled as described above. In some embodiments, the crRNA is labeled with biotin. In some embodiments, the method provided herein further comprises adding streptavidin and thereby separating the complex.

In some embodiments, the Cas protein or the derivative thereof is labeled with a capture tag. In some embodiments, the Cas protein or the variant thereof is a Cas9 protein or a variant thereof. In some embodiments, the Cas9 protein or the variant thereof retains two nuclease domains and is able to produce a double-stranded nucleic acid break. In some embodiments, the Cas9 protein contains one inactivated nuclease domain comprising a mutation in the domain that cleaves a target nucleic acid strand that is complementary to the crRNA. In some embodiments, said mutation is D10A. In some embodiments, the Cas9 protein contains one inactivated nuclease domain comprising a mutation in the domain that cleaves a target nucleic acid strand that is non-complementary to the crRNA. In some embodiments, said mutation is H840A. In some embodiments, the Cas9 protein contains two inactivated nuclease domains. In some embodiments, the two inactivated nuclease domains comprise a first mutation in the domain that cleaves the strand complementary to the crRNA and a second mutation in the domain that cleaves the strand non-complementary to the crRNA. In some embodiments, said first mutation is D10A and said second mutation is H840A.

In some embodiments, the method provided herein further includes tagmenting the target nucleic acid. In some embodiments, the method provided herein further includes adding a transposase, wherein the crRNA or the derivative thereof contains a transposon end. In some embodiments, the transposon end is a mosaic end (ME), and wherein the transposase is a Tn5 transposase. In some embodiments, the method provided herein further includes adding transposon end to the target nucleic acid, and tagmenting the target nucleic acid, wherein the endonuclease system further comprises a transposase.

In some embodiments, the transposase binds to a nucleotide sequence of the endonuclease system. In some embodiments, the transposase and the Cas protein form a fusion protein. In some embodiments, the transposon end is a mosaic end (ME), and wherein the transposase is a Tn5 transposase.

In another aspect, provided herein is a method for enriching a target nucleic acid including: obtaining a population of cell free DNA (cfDNA) from a subject's plasma or serum, the population of cell free DNA containing the target nucleic acid; providing an endonuclease system having: a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of the target nucleic acid; contacting the target nucleic acid with the endonuclease system to form a complex, and separating the complex and thereby enriching for the target nucleic acid.

In some embodiments, the target nucleic acid contains a single nucleotide variant (SNV). In some embodiments, the method further includes separating the target nucleic acid from the complex. In some embodiments, the method further includes amplifying the targeted nucleic acid. In some embodiments, the endonuclease system provided herein further includes a trans-activating crRNA (tracrRNA) or a derivative thereof. In some embodiments, the crRNA or the derivative thereof is a polynucleotide comprising a crRNA polynucleotide fused to a tracrRNA polynucleotide. In some embodiments, the endonuclease system provided herein is a Type II CRISPR-Cas system or a derivative thereof. In some embodiments, the target nucleic acid is a double-stranded DNA (dsDNA).

In some embodiments, the endonuclease system is labeled, as described above. In some embodiments, the crRNA is labeled with biotin. In some embodiments, the method provided herein further includes adding streptavidin and thereby separating the complex. In some embodiments, the Cas protein or the derivative thereof is labeled with a capture tag.

In some embodiments, the Cas protein or the variant thereof is a Cas9 protein or a variant thereof. In some embodiments, the Cas9 protein or the variant thereof retains two nuclease domains and is able to produce a double-stranded DNA break. In some embodiments, the Cas9 protein contains one inactivated nuclease domain comprising a mutation in the domain that cleaves a target nucleic acid strand that is complementary to the crRNA. In some embodiments, said mutation is D10A. In some embodiments, the Cas9 protein contains one inactivated nuclease domain comprising a mutation in the domain that cleaves a target nucleic acid strand that is non-complementary to the crRNA. In some embodiments, said mutation is H840A. In some embodiments, the Cas9 protein contains two inactivated nuclease domains. In some embodiments, the two inactivated nuclease domains comprise a first mutation in the domain that cleaves the strand complementary to the crRNA and a second mutation in the domain that cleaves the strand non-complementary to the crRNA. In some embodiments, said first mutation is D10A and said second mutation is H840A.

In some embodiments, the target nucleic acid is in a fetal cell faction of the cell free DNA, and wherein the cell free DNA is from maternal plasma. In some embodiments, the subject is a cancer patient.

In another aspect, provided herein is a method for detecting single nucleotide variant (SNV) including: obtaining a population of cell free DNA from a subject's plasma or serum; providing a first endonuclease system having: a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a first target-specific nucleotide region complementary to a region of a first target nucleic acid, and wherein the first Cas protein has nuclease activity; cleaving the first target nucleic acid using the endonuclease system, and amplifying a second target nucleic acid using Polymerase Chain Reaction (PCR), wherein the the second target nucleic acid contains a single nucleotide variant version of the first target nucleic acid.

In some embodiments, the first endonuclease system provided herein further includes a trans-activating crRNA (tracrRNA) or a derivative thereof. In some embodiments, the crRNA or the derivative thereof is a polynucleotide comprising a crRNA polynucleotide fused to a tracrRNA polynucleotide. In some embodiments, the first endonuclease system provided herein is a Type II CRISPR-Cas system or a derivative thereof. In some embodiments, the target nucleic acid is a double-stranded DNA (dsDNA). In some embodiments, the Cas protein or the variant thereof is a Cas9 protein or a variant thereof.

In some embodiments, the method provided herein further includes: providing a second endonuclease system having: a second clustered regularly interspaced short palindromic repeats (CRISPR) RNA (crRNA) or a derivative thereof, and a second CRISPR-associated (Cas) protein or a variant thereof, wherein the second crRNA or the derivative thereof contains a second target-specific nucleotide region complementary to a region of the second target nucleic acid; contacting the second target nucleic acid with the second endonuclease system to form a complex, and separating the complex and thereby enriching for the second target nucleic acid.

In some embodiments, the method provided herein further includes separating the second target nucleic acid from the complex. In some embodiments, the second endonuclease system further comprises a trans-activating crRNA (tracrRNA) or a derivative thereof. In some embodiments, the second crRNA or the derivative thereof is a polynucleotide comprising a crRNA polynucleotide fused to a tracrRNA polynucleotide. In some embodiments, the second endonuclease system is a Type II CRISPR-Cas system or a derivative thereof. In some embodiments, the second target nucleic acid is a double-stranded DNA (dsDNA).

In some embodiments, the second endonuclease system is labeled, as described above. In some embodiments, the second crRNA is labeled with biotin. In some embodiments, the method provided herein further includes adding streptavidin and thereby separating the complex. In some embodiments, the second Cas protein or the derivative thereof is labeled with a capture tag.

In some embodiments, the second Cas protein or the variant thereof is a Cas9 protein or a variant thereof. In some embodiments, the Cas9 protein or the variant thereof retains two nuclease domains and is able to produce a double-stranded nucleic acid break. In some embodiments, the Cas9 protein contains one inactivated nuclease domain comprising a mutation in the domain that cleaves a target nucleic acid strand that is complementary to the crRNA. In some embodiments, said mutation is D10A. In some embodiments, the Cas9 protein contains one inactivated nuclease domain comprising a mutation in the domain that cleaves a target nucleic acid strand that is non-complementary to the crRNA. In some embodiments, said mutation is H840A. In some embodiments, the Cas9 protein contains two inactivated nuclease domains. In some embodiments, the two inactivated nuclease domains comprise a first mutation in the domain that cleaves the strand complementary to the crRNA and a second mutation in the domain that cleaves the strand non-complementary to the crRNA. In some embodiments, said first mutation is D10A and said second mutation is H840A.

In some embodiments, the target nucleic acid is in a fetal cell faction of the cell free DNA, and wherein the cell free DNA is from maternal plasma. In some embodiments, the subject is a cancer patient.

In another aspect, provided herein is a method for labeling a target nucleic including providing a first nuclease system having: a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a first target-specific nucleotide region complementary to a first region of the target nucleic acid, and wherein the first Cas protein contains one inactivated nuclease domain; contacting a double-stranded nucleic acid containing the target nucleic acid with the first nuclease system to generate a first single-stranded nick at the first region of the target nucleic acid, and labeling the target nucleic acid.

In some embodiments, the method provided herein further includes separating the target nucleic acid through the labeling and thereby enriching the target nucleic acid. In some embodiments, the method provided herein further includes amplifying the target nucleic acid.

In some embodiments, the first nuclease system provided herein further includes a trans-activating crRNA (tracrRNA). In some embodiments, the first crRNA or the derivative thereof is a polynucleotide comprising a crRNA polynucleotide fused to a tracrRNA polynucleotide. In some embodiments, the first nuclease system is a Type II CRISPR-Cas system or a derivative thereof. In some embodiments, the target nucleic acid is a double-stranded DNA (dsDNA).

In some embodiments, the first Cas protein or the variant thereof is a Cas9 protein or a variant thereof. In some embodiments, the Cas9 protein or the variant thereof contains one inactivated nuclease domain comprising a mutation in the domain that cleaves a target nucleic acid strand that is complementary to the first crRNA. In some embodiments, said mutation is D10A. In some embodiments, the first Cas9 protein or the variant thereof contains one inactivated nuclease domain comprising a mutation in the domain that cleaves a target nucleic acid strand that is non-complementary to the first crRNA. In some embodiments, said mutation is H840A. In some embodiments, the method provided herein further includes performing a nick translation. In some embodiments, the nick translation is performed by using a nick translation polymerase selected from a group consisting of DNA Pol 1, Bst, and Taq. In some embodiments, the nick translation is performed in a reaction mixture containing biotinylated dNTPs. In some embodiments, the biotinylated dNTPs are biotinylated dUTPs. In some embodiments, the method provided herein further includes adding magnetic streptavidin beads to enrich biotinylated target nucleic acid.

In some embodiments, the method provided herein further includes providing a second nuclease system having: a second crRNA or a derivative thereof, and a second Cas protein or a variant thereof, wherein the second crRNA or the derivative thereof contains a second target-specific nucleotide region complementary to a second region of the target nucleic acid, and wherein the second Cas protein contains one inactivated nuclease domain, and contacting the double-stranded nucleic acid containing the target nucleic acid with the second nuclease system to generate a second single-stranded nick at the second region of the target nucleic acid, wherein the first region of the target nucleic acid is different from the second region of the target nucleic acid.

In some embodiments, the first single-stranded nick and the second single-stranded nick are on the same strand of the target nucleic acid. In some embodiments, the space between the first single-stranded nick and the second single-stranded nick on the same strand of the target nucleic acid is 1 bp to 20 bp. In some embodiments, the method further includes performing a nick translation. In some embodiments, the nick translation is performed by using a nick translation polymerase Phi29.

In some embodiments, the first region of the target nucleic acid and the second region of the target nucleic acid are on the same strand of the target nucleic acid; wherein the first Cas protein is a first Cas9 protein containing one inactivated nuclease domain comprising a first mutation in the domain that cleaves a target nucleic acid strand that is complementary to the first crRNA, and wherein the second Cas protein is a second Cas9 protein containing one inactivated nuclease domain containing a second mutation in the domain that cleaves a target nucleic acid strand that is complementary to the second crRNA. In some embodiments, the first mutation and the second mutation are both D10A.

In some embodiments, the first region of the target nucleic acid and the second region of the target nucleic acid are on the same strand of the target nucleic acid; wherein the first Cas protein is a first Cas9 protein containing one inactivated nuclease domain comprising a first mutation in the domain that cleaves a target nucleic acid strand that is non-complementary to the first crRNA, and wherein the second Cas protein is a second Cas9 protein containing one inactivated nuclease domain containing a second mutation in the domain that cleaves a target nucleic acid strand that is non-complementary to the second crRNA. In some embodiments, the first mutation and the second mutation are both H840A.

In some embodiments, the first region of the target nucleic acid and the second region of the target nucleic acid are on different strands of the target nucleic acid; the first Cas protein is a first Cas9 protein containing one inactivated nuclease domain comprising a first mutation in the domain that cleaves a target nucleic acid strand that is complementary to the first crRNA, and the second Cas protein is a second Cas9 protein containing one inactivated nuclease domain comprising a second mutation in the domain that cleaves a target nucleic acid strand that is non-complementary to the second crRNA. In some embodiments, said first mutation is D10A, and said second mutation is H840A.

In some embodiments, the space between the first single-stranded nick and the second single-stranded nick is from 20 bp to 500 bp.

In some embodiments, the method provided herein further includes adding a capture probe; and exchanging a single-stranded nucleic acid product between the first single-stranded nick and the second single-stranded nick with the capture probe, wherein the capture probe is able to hybridize to a nucleic acid complementary to the single-stranded nucleic acid product.

In some embodiments, the sequence of the capture probe is 10% to 100% identical to the sequence of the single-stranded nucleic acid product. In some embodiments, the capture probe is a biotinylated probe, and labelling can be performed as described above. In some embodiments, the method provided herein further includes adding magnetic streptavidin beads to enrich the target nucleic acid. In some embodiments, the capture probe contains an overhang nucleotide sequence, the overhang nucleotide sequence is complementary to an oligonucleotide immobilized on a surface.

In some embodiments, the first single-stranded nick and the second single-stranded nick are on opposite strands of the target nucleic acid, thereby generating a first double-stranded nucleic acid break end. In some embodiments, the first region of the target nucleic acid and the second region of the target nucleic acid are on the same strand of the target nucleic acid; the first Cas protein is a first Cas9 protein containing one inactivated nuclease domain comprising a first mutation in the domain that cleaves a target nucleic acid strand that is complementary to the first crRNA, and the second Cas protein is a second Cas9 protein containing one inactivated nuclease domain comprising a second mutation in the domain that cleaves a target nucleic acid strand that is non-complementary to the second crRNA. In some embodiments, the first mutation is D10A, and the second mutation is H840A.

In some embodiments, the first region of the target nucleic acid and the second region of the target nucleic acid are on opposite strands of the target nucleic acid; the first Cas protein is a first Cas9 protein containing one inactivated nuclease domain comprising a first mutation in the domain that cleaves a target nucleic acid strand that is complementary to the first crRNA, and the second Cas protein is a second Cas9 protein containing one inactivated nuclease domain containing a second mutation in the domain that cleaves a target nucleic acid strand that is complementary to the second crRNA. In some embodiments, the first mutation and the second mutation are both D10A.

In some embodiments, the first region of the target nucleic acid and the second region of the target nucleic acid are on opposite strands of the target nucleic acid; the first Cas protein is a first Cas9 protein containing one inactivated nuclease domain comprising a first mutation in the domain that cleaves a target nucleic acid strand that is non-complementary to the first crRNA, and the second Cas protein is a second Cas9 protein containing one inactivated nuclease domain containing a second mutation in the domain that cleaves a target nucleic acid strand that is non-complementary to the second crRNA. In some embodiments, the first mutation and the second mutation are both H840A.

In some embodiments, the method provided herein further includes ligating an adapter to the first double-stranded DNA break end. In some embodiments, the adapter is biotinylated. In some embodiments, the method provided herein further includes adding magnetic streptavidin beads to enrich the target nucleic acid.

In some embodiments, the method provided herein further includes providing a third nuclease system having: a third crRNA or a derivative thereof, and a third Cas protein or a variant thereof, wherein the third crRNA or the derivative thereof contains a third target-specific nucleotide region substantially complementary to a third region of the target nucleic acid, and wherein the third Cas protein contains one inactivated nuclease domain; providing a fourth nuclease system having: a fourth crRNA or a derivative thereof, and a fourth Cas protein or a variant thereof, wherein the fourth crRNA or the derivative thereof contains a fourth target-specific nucleotide region substantially complementary to a fourth region of the target nucleic acid, and wherein the fourth Cas protein contains one inactivated nuclease domain; and contacting the double-stranded nucleic acid containing the target nucleic acid with the third and fourth nuclease systems to generate a third single-stranded nick at the third region of the target nucleic acid and a fourth single-stranded nick at the fourth region of the target nucleic acid, wherein in the third single-stranded nick and the fourth single-stranded nick are on opposite strands of the target nucleic acid, thereby generating a second double-stranded nucleic acid break end, the second double-stranded nucleic acid break end being different from the first double-stranded nucleic acid break end. In some embodiments, the method further includes ligating an adapter to the second double-stranded nucleic acid break end.

In another aspect, provided herein is a method for enriching a target nucleic acid including: providing a population of Cas9 proteins programmed with a set of crRNAs, wherein the set of crRNAs contains crRNAs complementary to a series of different regions of the target nucleic acid; contacting the target nucleic acid with the population of Cas9 proteins programmed with the set of crRNAs to generate a series of nucleic acid fragments, and ligating adaptors to at least one of nucleic acid fragments, wherein the Cas9 protein retains two nuclease domains.

In some embodiments, the set of crRNAs contains crRNAs complementary to two different regions of the target nucleic acid. In some embodiments, the target nucleic acid is a double-stranded DNA. In some embodiments, the target nucleic acid is a genomic DNA, a chromosomal DNA, a genome, or a partial genome.

In another aspect, provided herein is a method for sequencing a target nucleic acid including: providing a population of Cas9 proteins programmed with a set of crRNAs, wherein the set of crRNAs contains crRNAs complementary to a series of different regions across the target nucleic acid; contacting the target nucleic acid with the population of Cas9 proteins programmed with the set of crRNAs to generate a series of nucleic acid fragments, and sequencing the series of nucleic acid fragments.

In some embodiments, provided herein is a method for sequencing a target nucleic acids including: providing a plurality of populations of Cas9 proteins, each population of Cas9 proteins being programmed with a different set of crRNAs, wherein each set of crRNAs contains crRNAs complementary to a different series of regions across the target nucleic acid, contacting the target nucleic acid with each of the plurality of populations of Cas9 proteins in a separate reaction to generate a different series of nucleic acid fragments, and sequencing the nucleic acid fragments.

In some embodiments, the plurality of populations of Cas9 proteins comprises three populations of Cas9 proteins, and wherein the nucleic acid fragments generated by each of the three populations of Cas9 proteins contain overlapping sequences with the nucleic acid fragments generated by at least another of the three populations of Cas9 proteins. In some embodiments, the Cas9 protein retains two nuclease domains. In some embodiments, the target nucleic acid is a double-stranded DNA. In some embodiments, the target nucleic acid is a genomic DNA, a chromosomal DNA, a genome, or a partial genome. In some embodiments, the method further includes ligating an adapter to the nucleic acid fragments. In some embodiments, the method provided herein further includes diluting a DNA sample containing the target DNA to haploid content. In some embodiments, the sequencing the nucleic acid fragments comprises use of one or more of sequencing by synthesis, bridge PCR, chain termination sequencing, sequencing by hybridization, nanopore sequencing, and sequencing by ligation.

Also provided herein is a method for enriching a plurality of target sequence comprising providing a plurality of populations of Cas9 proteins, each population of Cas9 proteins being programmed with a different set of crRNAs, wherein each set of crRNAs contains crRNAs complementary to a different series of regions across the target nucleic acid, contacting the target nucleic acid with each of the plurality of populations of Cas9 proteins in a separate reaction to generate a different series of nucleic acid fragments, wherein at least one of the following is labeled with a binding tag: Cas9 enzyme, crRNA, tracrRNA, and DNA probe targeting the displacement loop, and separating nucleic acid fragments associated with a labeled component of Cas9 complex from other fragments, thereby enriching the fragments of interest.

In certain embodiments, the binding tag comprises biotin. In certain embodiments, tracrRNA is labeled via in vitro transcription incorporating one or more biotinylated nucleotides. In certain embodiments, crRNA is labeled via in vitro transcription incorporating one or more biotinylated nucleotides. In certain embodiments, separating comprises binding nucleic acid fragment-Cas9 complexes with streptavidin labeled beads. In certain embodiments, binding comprises washing with a buffer comprising a salt concentration above 100 mM, 200 mM, 250 mM, 300 mM, 400 mM, 500 mM NaCl. In certain embodiments, contacting comprises buffer conditions comprising a salt concentration above 100 mM, 200 mM, 250 mM, 300 mM, 400 mM, 500 mM NaCl.

BRIEF DESCRIPTION OF THE DRAWINGS

In FIG. 2A, a plasmid containing wild type Braf sequence is first digested by AlwNI prior to providing a CRISPR-Cas system. In FIG. 2B, a plasmid containing wild type Braf sequence is first digested by Bgl 1 prior to providing a CRISPR-Cas system. FIG. 2C illustrates a Cas9 nickase mediated enrichment of fragments from a Nextera plasmid library. FIG. 2D shows the enrichment results of a Cas9 nickase mediated enrichment of fragments from a Nextera plasmid library.

FIG. 3 discloses SEQ ID NOS 1-3, respectively, in order of appearance.

FIG. 4A illustrates a method of tagmenting an enriched target DNA. FIG. 4B illustrates a method using a guide RNA containing a ME sequence. FIG. 4C illustrates a method using a CRIPR-Cas system containing a Tn5 dimer connected to the guide RNA. FIG. 4D illustrates a method using a CRIPR-Cas system containing a Tn5 dimer fused to the Cas9 protein. FIG. 4E illustrates a method for enriching a target nucleic acid using Tn5 and Cas9 protein. FIG. 4F illustrates a method of Cas9 mediated targeted sequencing including a tagmentation step.

FIG. 7A is a schematic illustrating the method of using a Cas9 nickase and nick translation. FIG. 7B illustrates incorporating dGTP and dUTP during a nick translation. FIG. 7C shows the results of a Cas9 nick translation.

FIGS. 8A-8E illustrate a method for generating two consecutive single-stranded nicks on the same strand of a target DNA using Cas9 nickases for enriching the target DNA. FIG. 8A is a schematic illustrating the method for generating two consecutive single-stranded nicks on the same strand of a target DNA using Cas9 nickases for enriching the target DNA. FIG. 8B shows the result of generating double nicks. FIG. 8C shows the results of generating double nicks using various Cas9 nickase concentrations. FIG. 8D shows the results of generating double nicks under denaturation temperature. FIG. 8E is a histogram showing the results of enrichment of Cas9 nicked DNA.

FIG. 12B is a schematic illustrating a targeted sequencing method using Cas9 mediated DNA fragmentation. FIG. 12C is a schematic illustrating a targeted haplotype sequencing using Cas9 mediated fragmentation.

FIG. 21 discloses "GGTCTCn^nnnn" as SEQ ID NO: 4 and "GAGnnnnnCTCnnnnnnnn nnnnn" as SEQ ID NO: 5.

FIG. 25 discloses SEQ ID NOS 6-9, respectively, in order of appearance.

DETAILED DESCRIPTION

Figure 1:
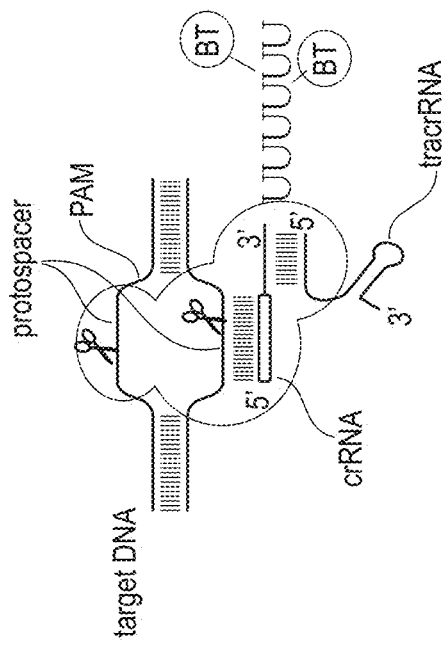
FIG. 1 illustrates a method provided herein for enriching a target DNA sequence using a CRISPR-Cas system. The endonuclease system-target DNA complex is illustrated in the right part of the figure.

The present disclosure provides methods for rapid and efficient enrichment of target nucleic acid using CRISPR-Cas systems. The present disclosure also provides methods for enriching and/or detecting polynucleotide variants using CRISPR-Cas systems. The present disclosure further provides methods for CRISPR-Cas system mediated targeted sequencing.

CRISPR-Cas systems can generally be categorized into three major types (Type I-III), which are further subdivided into ten subtypes, based on core element content and sequences (Makarova et al., 2011, *Nat Rev Microbiol* 9:467-77). The two key elements of these CRISPR-Cas systems are Cas proteins and CRISPR RNA (crRNA). CrRNA consists of short repeat sequences interspersed with spacer sequences derived from invader DNA. Cas proteins have various activities, e.g., nuclease activity. Thus, CRISPR-Cas systems provide mechanisms for targeting a specific sequence as well as certain enzyme activities upon the sequence.

A typical Type I CRISPR-Cas system contains Cas3 protein with separate helicase and DNase activities. For example, in the Type 1-E system, crRNAs are incorporated into a multisubunit effector complex called Cascade (CRISPR-associated complex for antiviral defense) (Brouns et al., 2008, *Science* 321: 960-4), which binds to the target DNA and triggers degradation by the Cas3 protein (Sinkunas et al., 2011, *EMBO J* 30:1335-1342; Beloglazova et al., 2011, *EMBO J* 30:616-627).

Type II CRISPR-Cas systems include the signature Cas9 protein, a single protein (about 160 KDa), capable of generating crRNA and cleaving the target DNA. The Cas9 protein typically contains two nuclease domains, a RuvC-like nuclease domain near the amino terminus and the HNH (or McrA-like) nuclease domain near the middle of the protein. Each nuclease domain of the Cas9 protein is specialized for cutting one strand of the double helix (Jinek et al., 2012, *Science* 337 (6096): 816-821).

Type III CRISPR-Cas systems contain polymerase and RAMP modules. Type III systems can be further divided into sub-types III-A and III-B. Type III-A CRISPR-Cas systems have been shown to target plasmids, and the polymerase-like proteins of Type III-A systems are involved in the cleavage of target DNA (Marraffini and Sontheimer, 2008, *Science* 322:1843-1845). Type III-B CRISPR-Cas systems have also been shown to target RNA (Hale et al., 2009, *Cell* 139:945-956).

The present disclosure relates, in part, to utilizing CRISPR-Cas systems and derivatives thereof for target-specific enrichment. In one embodiment, the present disclosure relates to enriching target DNA using a CRISPR-Cas system derived from a Type II CRISPR-Cas system. As discussed, the Type-II CRISPR-Cas system contains two key elements among other elements: crRNA and Cas9 protein. Both crRNA and Cas9 moieties provided herein can be engineered or programmed by users, enabling various methods for nucleic acid enrichment, detection, and/or sequencing provided herein.

Current target-specific enrichment protocols require that single-stranded nucleic acid be made prior to the target specific hybridization with probes. Among various advantages provided by the present disclosure, the present disclosure provides enrichment methods that can skip this step of generating single-stranded nucleic acid in the first place, and enable direct targeting to double-stranded nucleic acid, e.g., double-stranded DNA (dsDNA). Methods targeting directly to double-stranded DNA (either partly or completely double-stranded) have unique advantages over single-stranded enrichment strategies. For example, non-specific hybridization of single-stranded genomic DNA to targeted regions reduces specificity and often requires extensive stringency washing or other time-consuming steps; and single-stranded enrichment schemes often utilizes Cot-1 or other blocking DNA to reduce non-specific hybridization. These additives are not required from double-stranded DNA enrichment schemes, reducing both cost and number of required reagents. In addition, it is easier to make sequencing libraries from double-stranded DNA than from single-stranded DNA. As such, enrichment of double-stranded DNA allows library preparation (e.g., tagmentation) to occur after enrichment. For another example, since specificity (tree-like structures and non-specific hybridization is less of an issue with double-stranded DNA enrichment, potentially larger DNA fragments can be better specifically enriched compared to single-stranded DNA enrichment schemes. This is a particularly important advantage if one considers targeted sequencing in the context of haplotyping and assembly. Also, since longer DNA fragments can potentially be enriched, we have greater flexibility to where the target probe is designed. For example, we can avoid high polymorphic regions but still capture these regions. Also, fewer probes need to be used to capture large regions, reducing both capture probe cost and design.

In addition, the current protocols of target specific hybridization have slow kinetics and usually require high temperature. The present disclosure provides enzyme-driven sequence targeting methods that offer faster kinetics and easier workflow for enrichment. Because the hybridization to the target nucleic acid is enzyme driven in the present methods, the process can take place isothermally. In some embodiments, the method herein provides isothermal targeting of DNA at 20-37° C. Furthermore, the guide RNA, e.g., crRNA, in the system herein provides for sequence specificity as well as flexible programming that enables multiplex targeted enrichment (e.g., targeting multiple targeted regions with more probes made in various ways including IVT from oligo pool). The present disclosure also provides methods for enriching and/or detecting polynucleotide variants with higher sensitivity and specificity. Furthermore, the present invention also provides methods for targeted sequencing using CRISPR-Cas systems.

Definitions

As used herein, the terms "includes," "including," "includes," "including," "contains," "containing," "have," "having," and any variations thereof, are intended to cover a non-exclusive inclusion, such that a process, method, product-by-process, or composition of matter that includes, includes, or contains an element or list of elements does not include only those elements but can include other elements not expressly listed or inherent to such process, method, product-by-process, or composition of matter.

As used herein, the singular forms "a", "an" and "the" include plural referents unless the content clearly dictates otherwise. Thus, for example, reference to "a protein" includes a mixture of two or more proteins, and the like.

As used herein, the term "about" or "approximately" means within 5% of a given value or range.

As used herein, the term "nucleic acid" means single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH^{4+}$, trialkylammonium, tetraalkylammonium, $Mg^{2+}$, $Na^+$ and the like. A nucleic acid can be a polynucleotide or a oligonucleotide. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotides analogs. Nucleic acid typically ranges in size from a few monomeric units, e.g., 5-40, to several thousands of monomeric nucleotide units. Nucleic acids include, but are not limited to, genomic DNA, cDNA, hnRNA, mRNA, rRNA, tRNA, fragmented nucleic acid, nucleic acid obtained from sub-cellular organelles such as mitochondria or chloroplasts, and nucleic acid obtained from microorganisms or DNA or RNA viruses that may be present on or in a biological sample.

As used herein, the term "target nucleic acid" is intended to mean a nucleic acid that is the object of an analysis or action. The analysis or action includes subjecting the nucleic acid to copying, amplification, sequencing and/or other procedure for nucleic acid interrogation. A target nucleic acid can include nucleotide sequences additional to the target sequence to be analyzed. For example, a target nucleic acid can include one or more adapters, including an adapter that functions as a primer binding site, that flank(s) a target nucleic acid sequence that is to be analyzed. A target nucleic acid hybridized to a capture oligonucleotide or capture primer can contain nucleotides that extend beyond the 5' or 3' end of the capture oligonucleotide in such a way that not all of the target nucleic acid is amenable to extension.

As used herein, the term "target specific" when used in reference to a guide RNA, a crRNA or a derivative thereof, or other nucleotide is intended to mean a polynucleotide that includes a nucleotide sequence specific to a target polynucleotide sequence, namely a sequence of nucleotides capable of selectively annealing to an identifying region of a target polynucleotide, e.g., a target DNA. Target specific nucleotide can have a single species of oligonucleotide, or it can include two or more species with different sequences. Thus, the target specific nucleotide can be two or more sequences, including 3, 4, 5, 6, 7, 8, 9 or 10 or more different sequences. In one embodiment, a crRNA or the derivative thereof contains a target-specific nucleotide region complementary to a region of the target DNA sequence. In one embodiment, a crRNA or the derivative thereof may contain other nucleotide sequences besides a target-specific nucleotide region. In one embodiment, the other nucleotide sequences may be from a tracrRNA sequence.

As used herein, the term "complementary" when used in reference to a polynucleotide is intended to mean a polynucleotide that includes a nucleotide sequence capable of selectively annealing to an identifying region of a target polynucleotide under certain conditions. As used herein, the term "substantially complementary" and grammatical equivalents is intended to mean a polynucleotide that includes a nucleotide sequence capable of specifically annealing to an identifying region of a target polynucleotide under certain conditions. Annealing refers to the nucleotide base-pairing interaction of one nucleic acid with another nucleic acid that results in the formation of a duplex, triplex, or other higher-ordered structure. The primary interaction is typically nucleotide base specific, e.g., A:T, A:U, and G:C, by Watson-Crick and Hoogsteen-type hydrogen bonding. In certain embodiments, base-stacking and hydrophobic interactions can also contribute to duplex stability. Conditions under which a polynucleotide anneals to complementary or substantially complementary regions of target nucleic acids are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349 (1968). Annealing conditions will depend upon the particular application, and can be routinely determined by persons skilled in the art, without undue experimentation.

As used herein, the term "hybridization" refers to the process in which two single-stranded polynucleotides bind non-covalently to form a stable double-stranded polynucleotide. A resulting double-stranded polynucleotide is a "hybrid" or "duplex." Hybridization conditions will typically include salt concentrations of less than about 1 M, more usually less than about 500 mM and may be less than about 200 mM. A hybridization buffer includes a buffered salt solution such as 5% SSPE, or other such buffers known in the art. Hybridization temperatures can be as low as 5° C., but are typically greater than 22° C., and more typically greater than about 30° C., and typically in excess of 37° C. Hybridizations are usually performed under stringent conditions, i.e., conditions under which a probe will hybridize to its target subsequence but will not hybridize to the other, uncomplimentary sequences. Stringent conditions are sequence-dependent and are different in different circumstances, and may be determined routinely by those skilled in the art.

In the context of "polynucleotides," the terms "variant" and "derivative" as used herein refer to a polynucleotide that comprises a nucleotide sequence of a polynucleotide or a fragment of a polynucleotide, which has been altered by the introduction of nucleotide substitutions, deletions or additions. A variant or a derivative of a polynucleotide can be a fusion polynucleotide which contains part of the nucleotide sequence of a polynucleotide. The term "variant" or "derivative" as used herein also refers to a polynucleotide or a fragment thereof, which has been chemically modified, e.g., by the covalent attachment of any type of molecule to the polynucleotide. For example, but not by way of limitation, a polynucleotide or a fragment thereof can be chemically modified, e.g., by acetylation, phosphorylation, methylation, etc. The variants or derivatives are modified in a manner that is different from naturally occurring or starting nucleotide or polynucleotide, either in the type or location of the molecules attached. Variants or derivatives further include deletion of one or more chemical groups which are naturally present on the nucleotide or polynucleotide. A variant or a derivative of a polynucleotide or a fragment of a polynucleotide can be chemically modified by chemical modifications using techniques known to those of skill in the art, including, but not limited to specific chemical cleavage, acetylation, formulation, etc. Further, a variant or a derivative of a polynucleotide or a fragment of a polynucleotide can contain one or more dNTPs or nucleotide analogs. A polynucleotide variant or derivative may possess a similar or identical function as a polynucleotide or a fragment of a polynucleotide described herein. A polynucleotide variant or derivative may possess an additional or different function compared with a polynucleotide or a fragment of a polynucleotide described herein.

As used herein, the term "dNTP" refers to deoxynucleoside triphosphates. NTP refers to ribonucleotide triphosphates such as those used to synthesize crRNA or tracrRNA. The purine bases (Pu) include adenine (A), guanine (G) and derivatives and analogs thereof. The pyrimidine bases (Py) include cytosine (C), thymine (T), uracil (U) and derivatives and analogs thereof. Examples of such derivatives or analogs, by way of illustration and not limitation, are those which are modified with a reporter group, biotinylated, amine modified, radiolabeled, alkylated, and the like and also include phosphorothioate, phosphite, ring atom modified derivatives, and the like. The reporter group can be a fluorescent group such as fluorescein, a chemiluminescent group such as luminol, a terbium chelator such as N-(hydroxyethyl)ethylenediaminetriacetic acid that is capable of detection by delayed fluorescence, and the like.

As used herein, the term "nucleotide analogs" refers to synthetic analogs having modified nucleotide base portions, modified pentose portions, and/or modified phosphate portions, and, in the case of polynucleotides, modified internucleotide linkages, as generally described elsewhere (e.g., Scheit, *Nucleotide Analogs*, John Wiley, New York, 1980; Englisch, *Angew. Chem. Int. Ed. Engl.* 30:613-29, 1991; Agarwal, *Protocols for Polynucleotides and Analogs*, Humana Press, 1994; and S. Verma and F. Eckstein, Ann. Rev. Biochem. 67:99-134, 1998). Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Exemplary modified nucleotide base portions include but are not limited to 5-methylcytosine (5mC); C-5-propynyl analogs, including but not limited to, C-5 propynyl-C and C-5 propynyl-U; 2,6-diaminopurine, also known as 2-amino adenine or 2-amino-dA); hypoxanthine, pseudouridine, 2-thiopyrimidine, isocytosine (isoC), 5-methyl isoC, and isoguanine (isoG; see, e.g., U.S. Pat. No. 5,432,272). Exemplary modified pentose portions include but are not limited to, locked nucleic acid (LNA) analogs including without limitation Bz-A-LNA, 5-Me-Bz-C-LNA, dmf-G-LNA, and T-LNA (see, e.g., The Glen Report, 16(2):5, 2003; Koshkin et al., *Tetrahedron* 54:3607-30, 1998), and 2'- or 3'-modifications where the 2'- or 3'-position is hydrogen, hydroxy, alkoxy (e.g., methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged intersubunit linkages (e.g., Sterchak, E. P. et al., *Organic Chern.*, 52:4202, 1987), and uncharged morpholino-based polymers having achiral intersubunit linkages (see, e.g., U.S. Pat. No. 5,034,506). Some internucleotide linkage analogs include morpholidate, acetal, and polyamide-linked heterocycles.

As used herein, the terms "ligation," "ligating," and grammatical equivalents thereof are intended to mean to form a covalent bond or linkage between the termini of two or more nucleic acids, e.g., oligonucleotides and/or polynucleotides, typically in a template-driven reaction. The nature of the bond or linkage may vary widely and the ligation may be carried out enzymatically or chemically. As used herein, ligations are usually carried out enzymatically to form a phosphodiester linkage between a 5' carbon terminal nucleotide of one oligonucleotide with a 3' carbon of another nucleotide. Template driven ligation reactions are described in the following references: U.S. Pat. Nos. 4,883,750; 5,476,930; 5,593,826; and 5,871,921, incorporated herein by reference in their entireties. The term "ligation" also encompasses non-enzymatic formation of phosphodiester bonds, as well as the formation of non-phosphodiester covalent bonds between the ends of oligonucleotides, such as phosphorothioate bonds, disulfide bonds, and the like.

As used herein, the term "adapter" is a single-stranded or a double-stranded nucleic acid molecule that can be linked to the end of other nucleic acids. In one embodiment, an adapter is a short, chemically synthesized, double-stranded nucleic acid molecule which can be used to link the ends of two other nucleic acid molecules. In one embodiment, an adaptor is a double-stranded nucleic acid (e.g., oligonucleotides) that comprises single-stranded nucleotide overhangs at the 5' and/or 3' ends. In some embodiments, the single-stranded overhangs are 1, 2 or more nucleotides. In some embodiments, adaptors comprise additional nucleic acid sequence for cloning or analysis of "inserts." In some embodiments, adaptors comprise labels or affinity tags for analysis or purification of "inserts." The term "insert" refers to a nucleic acid sequence of interest. In some embodiments, inserts are double-stranded DNAs that comprise single stranded nucleotide overhangs at the 5' and/or 3' ends. In some embodiments, the single stranded overhangs are 1, 2 or more nucleotides.

As used herein, the term "nick translation" refers to a process which replaces some of the nucleotides of a nucleic acid from a single-stranded nucleic acid nick with their labeled analogs by using a polymerase, creating a tagged nucleic acid sequence. The term "nick translation polymerase" refers to a polymerase, e.g., DNA polymerase, used in a nick translation process. In one embodiment, the nick translation polymerase is DNA polymerase I, which elongates the 3' hydroxyl terminus, removing nucleotides by 5'-3' exonuclease activity, replacing them with dNTPs.

As used herein, the term "tagmentation," "tagment," or "tagmenting" refers to transforming a nucleic acid, e.g., a DNA, into adaptor-modified templates in solution ready for cluster formation and sequencing by the use of transposase mediated fragmentation and tagging. This process often involves the modification of the nucleic acid by a transposome complex comprising transposase enzyme complexed with adaptors comprising transposon end sequence. Tagmentation results in the simultaneous fragmentation of the nucleic acid and ligation of the adaptors to the 5' ends of both strands of duplex fragments. Following a purification step to remove the transposase enzyme, additional sequences are added to the ends of the adapted fragments by PCR.

As used herein, the term "transposome complex" refers to a transposase enzyme non-covalently bound to a double stranded nucleic acid. For example, the complex can be a transposase enzyme preincubated with double-stranded transposon DNA under conditions that support non-covalent complex formation. Double-stranded transposon DNA can include, without limitation, Tn5 DNA, a portion of Tn5 DNA, a transposon end composition, a mixture of transposon end compositions or other double-stranded DNAs capable of interacting with a transposase such as the hyperactive Tn5 transposase.

A "transposase" means an enzyme that is capable of forming a functional complex with a transposon end-containing composition (e.g., transposons, transposon ends, transposon end compositions) and catalyzing insertion or transposition of the transposon end-containing composition into the double-stranded target nucleic acid with which it is incubated, for example, in an in vitro transposition reaction. A transposase as presented herein can also include integrases from retrotransposons and retroviruses. Transposases, transposomes and transposome complexes are generally known to those of skill in the art, as exemplified by the disclosure of US 2010/0120098, the content of which is incorporated herein by reference in its entirety. Although many embodiments described herein refer to Tn5 transposase and/or hyperactive Tn5 transposase, it will be appreciated that any transposition system that is capable of inserting a transposon end with sufficient efficiency to 5'-tag and fragment a target nucleic acid for its intended purpose can be used in the present invention. In particular embodiments, a preferred transposition system is capable of inserting the transposon end in a random or in an almost random manner to 5'-tag and fragment the target nucleic acid.

As used herein, the term "transposition reaction" refers to a reaction wherein one or more transposons are inserted into target nucleic acids, e.g., at random sites or almost random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further comprise additional sequences (e.g., adaptor or primer sequences) as needed or desired. In some embodiments, the method provided herein is exemplified by employing a transposition complex formed by a hyperactive Tn5 transposase and a Tn5-type transposon end (Goryshin and Reznikoff, 1998, *J. Biol. Chem.*, 273: 7367) or by a MuA transposase and a Mu transposon end comprising R1 and R2 end sequences (Mizuuchi, 1983, *Cell*, 35: 785; Savilahti et al., 1995, *EMBO J.*, 14: 4893). However, any transposition system that is capable of inserting a transposon end in a random or in an almost random manner with sufficient efficiency to 5'-tag and fragment a target DNA for its intended purpose can be used in the present invention. Examples of transposition systems known in the art which can be used for the present methods include but are not limited to *Staphylococcus aureus* Tn552 (Colegio et al., 2001, *J Bacteriol.*, 183: 2384-8; Kirby et al., 2002, *Mol Microbiol*, 43: 173-86), Ty1 (Devine and Boeke, 1994, *Nucleic Acids Res.*, 22: 3765-72 and International Patent Application No. WO 95/23875), Transposon Tn7 (Craig, 1996, *Science.* 271: 1512; Craig, 1996, Review in: *Curr Top Microbiol Immunol*, 204: 27-48), Tn10 and IS10 (Kleckner et al., 1996, *Curr Top Microbiol Immunol*, 204: 49-82), Mariner transposase (Lampe et al., 1996, *EMBO J.*, 15: 5470-9), Tci (Plasterk, 1996, *Curr Top Microbiol Immunol*, 204: 125-43), P Element (Gloor, 2004, *Methods Mol Biol*, 260: 97-114), TnJ (Ichikawa and Ohtsubo, 1990, *J Biol Chem.* 265: 18829-32), bacterial insertion sequences (Ohtsubo and Sekine, 1996, *Curr. Top. Microbiol. Immunol.* 204:1-26), retroviruses (Brown et al., 1989, *Proc Natl Acad Sci USA*, 86: 2525-9), and retrotransposon of yeast (Boeke and Corces, 1989, *Annu Rev Microbiol.* 43: 403-34). The method for inserting a transposon end into a target sequence can be carried out in vitro using any suitable transposon system for which a suitable in vitro transposition system is available or that can be developed based on knowledge in the art. In general, a suitable in vitro transposition system for use in the methods provided herein requires, at a minimum, a transposase enzyme of sufficient purity, sufficient concentration, and sufficient in vitro transposition activity and a transposon end with which the transposase forms a functional complex with the respective transposase that is capable of catalyzing the transposition reaction. Suitable transposase transposon end sequences that can be used in the invention include but are not limited to wild-type, derivative or mutant transposon end sequences that form a complex with a transposase chosen from among a wild-type, derivative or mutant form of the transposase.

The term "transposon end" (TE) refers to a double-stranded nucleic acid, e.g., a double-stranded DNA, that exhibits only the nucleotide sequences (the "transposon end sequences") that are necessary to form the complex with the transposase or integrase enzyme that is functional in an in vitro transposition reaction. In some embodiments, a transposon end is capable of forming a functional complex with the transposase in a transposition reaction. As non-limiting examples, transposon ends can include the 19-bp outer end ("OE") transposon end, inner end ("IE") transposon end, or "mosaic end" ("ME") transposon end recognized by a wild-type or mutant Tn5 transposase, or the R1 and R2 transposon end as set forth in the disclosure of US 2010/0120098, the content of which is incorporated herein by reference in its entirety. Transposon ends can include any nucleic acid or nucleic acid analogue suitable for forming a functional complex with the transposase or integrase enzyme in an in vitro transposition reaction. For example, the transposon end can include DNA, RNA, modified bases, non-natural bases, modified backbone, and can include nicks in one or both strands. Although the term "DNA" is sometimes used in the present disclosure in connection with the composition of transposon ends, it should be understood that any suitable nucleic acid or nucleic acid analogue can be utilized in a transposon end.

As used herein, the terms "solid surface," "solid support" and other grammatical equivalents herein refer to any material that is appropriate for or can be modified to be appropriate for the attachment of a polynucleotide. Possible substrates include, but are not limited to, glass and modified or functionalized glass, plastics (including acrylics, polystyrene and copolymers of styrene and other materials, polypropylene, polyethylene, polybutylene, polyurethanes, Teflon™, etc.), polysaccharides, nylon or nitrocellulose, ceramics, resins, silica or silica-based materials including silicon and modified silicon, carbon, metals, inorganic glasses, plastics, optical fiber bundles, and a variety of other polymers. In some embodiments, solid supports and solid surfaces are located within a flow cell apparatus. In some embodiments, the solid support comprises a patterned surface suitable for immobilization of molecules in an ordered pattern. A "patterned surface" refers to an arrangement of different regions in or on an exposed layer of a solid support. In some embodiments, the solid support comprises an array of wells or depressions in a surface. The composition and geometry of the solid support can vary with its use. In some embodiments, the solid support is a planar structure such as a slide, chip, microchip and/or array. As such, the surface of a substrate can be in the form of a planar layer. In some embodiments, the solid support comprises one or more surfaces of a flowcell. The term "flowcell" as used herein refers to a chamber comprising a solid surface across which one or more fluid reagents can be flowed. Examples of flowcells and related fluidic systems and detection platforms that can be readily used in the methods of the present disclosure are described, for example, in Bentley et al., *Nature* 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference. In some embodiments, the solid support or its surface is non-planar, such as the inner or outer surface of a tube or vessel. In some embodiments, the solid support comprises microspheres or beads. "Microspheres," "beads," "particles," or grammatical equivalents herein are intended to mean small discrete particles made of various material including, but are not limited to, plastics, ceramics, glass, and polystyrene. In certain embodiments, the microspheres are magnetic microspheres or beads. Alternatively or additionally, the beads may be porous. The bead sizes range from nanometers, e.g. 100 nm, to millimeters, e.g. 1 mm.

As used herein, the term "CRISPR-Cas system" refers to an enzyme system including a guide RNA sequence that contains a nucleotide sequence complementary or substantially complementary to a region of a target polynucleotide, and a protein with nuclease activity. CRISPR-Cas systems include Type I CRISPR-Cas system, Type II CRISPR-Cas system, Type III CRISPR-Cas system, and derivatives thereof. CRISPR-Cas systems include engineered and/or programmed nuclease systems derived from naturally accruing CRISPR-Cas systems. CRISPR-Cas systems may contain engineered and/or mutated Cas proteins. CRISPR-Cas systems may contain engineered and/or programmed guide RNA.

As used herein, the term "guide RNA" refers to a RNA containing a sequence that is complementary or substantially complementary to a region of a target DNA sequence. A guide RNA may contain nucleotide sequences other than the region complementary or substantially complementary to a region of a target DNA sequence. A guide RNA may be a crRNA or a derivative thereof, e.g., a crRNA:tracrRNA chimera.

As used herein, the term "nuclease" refers to an enzyme capable of cleaving the phosphodiester bonds between the nucleotide subunits of nucleic acids; the term "endonuclease" refers to an enzyme capable of cleaving the phosphodiester bond within a polynucleotide chain; and the term "nickase" refers to an endonuclease which cleaves only a single strand of a DNA duplex. The term "Cas9 nickase" refers to a nickase derived from a Cas9 protein, typically by inactivating one nuclease domain of Cas9 protein.

In the context of a polypeptide, the terms "variant" and "derivative" as used herein refer to a polypeptide that comprises an amino acid sequence of a polypeptide or a fragment of a polypeptide, which has been altered by the introduction of amino acid residue substitutions, deletions or additions. A variant or a derivative of a polypeptide can be a fusion protein which contains part of the amino acid sequence of a polypeptide. The term "variant" or "derivative" as used herein also refers to a polypeptide or a fragment of a polypeptide, which has been chemically modified, e.g., by the covalent attachment of any type of molecule to the polypeptide. For example, but not by way of limitation, a polypeptide or a fragment of a polypeptide can be chemically modified, e.g., by glycosylation, acetylation, pegylation, phosphorylation, amidation, derivatization by known protecting/blocking groups, proteolytic cleavage, linkage to a cellular ligand or other protein, etc. The variants or derivatives are modified in a manner that is different from naturally occurring or starting peptide or polypeptides, either in the type or location of the molecules attached. Variants or derivatives further include deletion of one or more chemical groups which are naturally present on the peptide or polypeptide. A variant or a derivative of a polypeptide or a fragment of a polypeptide can be chemically modified by chemical modifications using techniques known to those of skill in the art, including, but not limited to specific chemical cleavage, acetylation, formulation, metabolic synthesis of tunicamycin, etc. Further, a variant or a derivative of a polypeptide or a fragment of a polypeptide can contain one or more non-classical amino acids. A polypeptide variant or derivative may possess a similar or identical function as a polypeptide or a fragment of a polypeptide described herein. A polypeptide variant or derivative may possess an additional or different function compared with a polypeptide or a fragment of a polypeptide described herein.

As used herein, the term "label" refers to a process in which a component, e.g., a RNA or a protein, is modified, e.g., binding to another molecule, so that to facilitate separation of the component and its associated elements. In one embodiment, a RNA in a CRISPR-Cas system is labeled. In some embodiments, the RNA is labeled with biotinylated dNTP. In some embodiments, the RNA is labeled with another polynucleotide probe. The polynucleotide probe may contain a sequence substantially complementary to a region of the RNA. In some embodiments, the RNA end is labeled with an adapter. In one embodiment, a protein, e.g., a Cas protein, is labeled with a capture tag. The term "capture tag" as used herein refers to a molecule used as a target in a pull-down procedure. In some embodiments, the capture tag is an affinity tag. The term "affinity tag" as used herein refers to molecules that have affinity for and "bind" to another substance under certain conditions, referred to as "binding conditions", to form a "specific binding pair." For example, biotin and streptavidin, biotin and avidin, or digoxigenin and a specific antibody that binds digoxigenin are examples of "specific binding pairs."

In some embodiments, one or more of the following Cas9 complex components can be labeled with a binding tag: Cas9 enzyme, crRNA, tracrRNA, and DNA probe targeting the displacement loop. In some embodiments, the binding tag is biotin, or a functional analogue thereof.

In certain embodiments, where the Cas9 enzyme is labeled with a binding tag, the protein can be chemically tagged. For example, Cas9 can be chemically biotinylated. As another example, a fusion can be created by adding additional sequence encoding a fusion to the Cas9 gene. One example of a fusion useful in such embodiments is an AviTag™, which employs a highly targeted enzymatic conjugation of a single biotin on a unique 15 amino acid peptide tag.

In certain embodiments, where crRNA is labeled with a binding tag, the entire crRNA can be labeled using in vitro transcription (IVT) incorporating one or more biotinylated nucleotides, such as, for example biotinylated uracil. In some embodiments, biotin can be chemically or enzymatically added to crRNA, such as, for example, the addition of 2 biotin groups (dual biotin) at the 3' end of crRNA.

In certain embodiments, where tracrRNA is labeled with a binding tag, the entire tracrRNA can be labeled using in vitro transcription (IVT) incorporating one or more biotinylated nucleotides, such as, for example biotinylated uracil. In some embodiments, biotin can be chemically or enzymatically added to tracrRNA, such as, for example, the addition of 2 biotin groups (dual biotin) at the 3' end of tracrRNA.

In certain embodiments, where a probe targeting the displacement loop is labeled with a binding tag, an oligonucleotide having the specific sequence of interest can be synthesized by adding a biotin group at the 5' end of the oligonucleotide probe. For example, one or more biotinylated phosphoramadites can be incorporated into an oligonucleotide during synthesis.

As used herein, in the context of enriching a target polynucleotide, the term "enrich," "enriching", or "enrichment" refers to a process which results in a higher percentage of the target polynucleotide in a polynucleotide population. In one embodiment, the percentage increases about 5%, 10%, 20%, 30%, 40%, 50%, 60%, 70%, 80%, 90% or 100%. In one embodiment, the percentage increases about 2 fold, 5 fold, 10 fold, 50 fold, or 100 fold. In one embodiment, the target polynucleotide is substantially isolated from the polynucleotide population.

As used herein, the term "detecting" a nucleic acid molecule or fragment thereof refers to determining the presence of the nucleic acid molecule, typically when the nucleic acid molecule or fragment thereof has been fully or partially separated from other components of a sample or composition, and also can include determining the chargeto-mass ratio, the mass, the amount, the absorbance, the fluorescence, or other property of the nucleic acid molecule or fragment thereof.

As used herein, the term "single nucleotide polymorphism (SNP)" refers to a DNA sequence variation occurring when a single nucleotide—A, T, C, or G—in the genome (or other shared sequence) differs between members of a species (or between paired chromosomes in an individual).

As used herein, the term "single nucleotide variant (SNV)" refers to one kind of genotype or polynucleotide including a single nucleotide polymorphism (SNP) or point mutation site.

As used herein, the terms "subject" and "patient" are used interchangeably. As used herein, a subject is preferably a mammal such as a non-primate (e.g., cows, pigs, horses, cats, dogs, rats, etc.) or a primate (e.g., monkey and human). In specific embodiments, the subject is a human. In one embodiment, the subject is a mammal (e.g., a human) having a cancer.

As used herein, the terms "haplotype," "haploid genotype," and other grammatical equivalents herein refer to a set of nucleotide sequence polymorphisms or alleles present on a single maternal or paternal chromosome, usually inherited as a unit.

As used herein, the terms "phased sequencing," "haplotype sequencing," and other grammatical equivalents when used in context of a genome or a chromosome refer to determining the nucleic acid sequence of a single genome or single chromosome, respectively, where the nucleic acid sequence is obtained from the sequencing of a single genome or a single chromosome. The terms "phased sequencing," "haplotype sequencing," and other grammatical equivalents when used in context of a chromosomal fragment refer to determining the nucleic acid sequence of a single chromosomal fragment where the nucleic acid sequence is obtained from the sequencing of a single chromosomal fragment.

Methods for Enriching Polynucleotides

In one aspect, the present disclosure provides a method for enriching a target nucleic acid using an endonuclease system derived from a CRISPR-Cas system. The present disclosure is based, in part, on the capability of CRISPR-Cas system to specifically bind with a target nucleic acid. Such target specific binding by the CRISPR-Cas system provides methods for efficiently enriching target nucleic acid, e.g., by pulling down an element of CRISPR-Cas that is associated with the target nucleic acid. CRISPR-Cas mediated nucleic acid enrichment bypasses traditionally required step of generating single-stranded nucleic acid prior to target specific binding, and enables directly targeting double-stranded nucleic acid, e.g., double-stranded DNA (dsDNA). In addition, CRISPR-Cas mediated nucleic acid binding is enzyme-driven, and thus it can offer faster kinetics and easier workflows for enrichment with lower temperature and/or isothermal reaction conditions.

In one embodiment, the present disclosure provides a method for enriching a target nucleic acid including: providing an endonuclease system having a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of the target nucleic acid; contacting the target nucleic acid with the endonuclease system to form a complex, and separating the complex and thereby enriching for the target nucleic acid.

In some embodiments, the method provided herein further includes separating the target nucleic acid from the complex. In one embodiment, the CRISPR-Cas system can be bound to a surface, e.g., in plate once it has found the targeted region. This can prevent dissociation of the complex prematurely, and thus improve efficiency of capture. In some embodiments, the method provided herein further includes amplifying the target nucleic acid sequence.

As illustrated in FIG. 1, a CRISPR-Cas system, e.g., a Type II CRISPR-Cas system, is provided, and the enzyme system contacts a target DNA to form a complex. The right part of FIG. 1 illustrates a CRISPR-Cas system-target DNA complex. As shown, the guide RNA is labeled, e.g., with biotinylated dUTP, and as such the complex can be separated by pulling down the labeled RNA.

In some embodiments, the target nucleic acid provided herein is a double-stranded DNA (dsDNA). Certain CRISPR-Cas systems, e.g., Type II CRISPR-Cas systems, bind to double-stranded DNA in an enzyme-driven and sequence-specific manner. Therefore, one advantage provided herein is directly targeting double-stranded DNA, rather than processed single-stranded DNA, for enrichment.

The endonuclease system provided herein is derived from a CRISPR-Cas system. In some embodiments, the endonuclease system provided herein is a Type I CRISPR-Cas system or a derivative thereof. In some embodiments, the endonuclease system provided herein is a Type II CRISPR-Cas system. In some embodiments, the endonuclease system provided herein is a Type III CRISPR-Cas system or a derivative thereof. The CRISPR-Cas systems provided herein include engineered and/or programmed nuclease systems derived from naturally occurring CRISPR-Cas systems. CRISPR-Cas systems may include contain engineered and/or mutated Cas proteins. CRISPR-Cas systems may also contain engineered and/or programmed guide RNA. For example, in some embodiments, crRNA and tracrRNA are synthesized by in vitro transcription, using a synthetic double stranded DNA template containing the T7 promoter. The tracrRNA has a fixed sequence, whereas the target sequence dictates part of crRNA's sequence. Equal molarities of crRNA and tracrRNA are mixed and heated at 55° C. for 30 seconds. Cas9 is added at the same molarity at 37° C. and incubated for 10 minutes with the RNA mix. 10-20 fold molar excess of Cas9 complex is then added to the target DNA. The cleavage/binding reaction can occur within 15 minutes.

The key elements of a CRISPR-Cas system include a guide RNA, e.g., a crRNA, and a Cas protein. The crRNA or the derivative thereof contains a target specific nucleotide region complementary or substantially complementary to a region of the target nucleic acid. In some embodiments, the crRNA or the derivative thereof contains a user-selectable RNA sequence that permits specific targeting of the enzyme to a complementary double-stranded DNA. In some embodiments, the user-selectable RNA sequence contains 20-50 nucleotides complementary or substantially complementary to a region of the target DNA sequence. In some embodiments, the target specific nucleotide region of the crRNA has 100% base pair matching with the region of the target nucleic acid. In some embodiments, the target specific nucleotide region of the crRNA has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two base pair mismatches between the target specific nucleotide region of the crRNA and the region of the target nucleic acid. In some embodiments, there are three base pair mismatches between the target specific nucleotide region of the crRNA and the region of the target nucleic acid. In some embodiments, there are four base pair mismatches between the target specific nucleotide region of the crRNA and the region of the target nucleic acid. In some embodiments, there are five base pair mismatches between the target specific nucleotide region of the crRNA and the region of the target nucleic acid.

In some embodiments, the endonuclease system provided herein further includes a trans-activating crRNA (tracrRNA) or a derivative thereof. In some embodiments, the crRNA or the derivative thereof provided herein is a polynucleotide having a crRNA polynucleotide fused to a tracrRNA polynucleotide. A chimeric single-guided RNA (sgRNA) is described in Jinek et al., 2012, *Science* 337, 816-821, which is incorporated herein in its entirety. In one embodiment, the Cas protein or the variant thereof provided herein can be directed by a chimeric sgRNA to any genomic locus followed by a 5'-NGG protospacer-adjacent motif (PAM).

In some embodiments, the Cas protein or the variant thereof is a Cas9 protein or a variant thereof. Isolated Cas9-crRNA complex from the *S. thermophilus* CRISPR-Cas system as well as complex assembled in vitro from separate components demonstrate that it binds to both synthetic oligodeoxynucleotide and plasmid DNA bearing a nucleotide sequence complementary to the crRNA. It has been shown that Cas9 has two nuclease domains—RuvC- and HNH-active sites/nuclease domains, and these two nuclease domains are responsible for the cleavage of opposite DNA strands. In some embodiments, the Cas9 protein is derived from Cas9 protein of *S. thermophilus* CRISPR-Cas system. In some embodiments, the Cas9 protein is a multi-domain protein having about 1,409 amino acids residues.

Figure 2A:
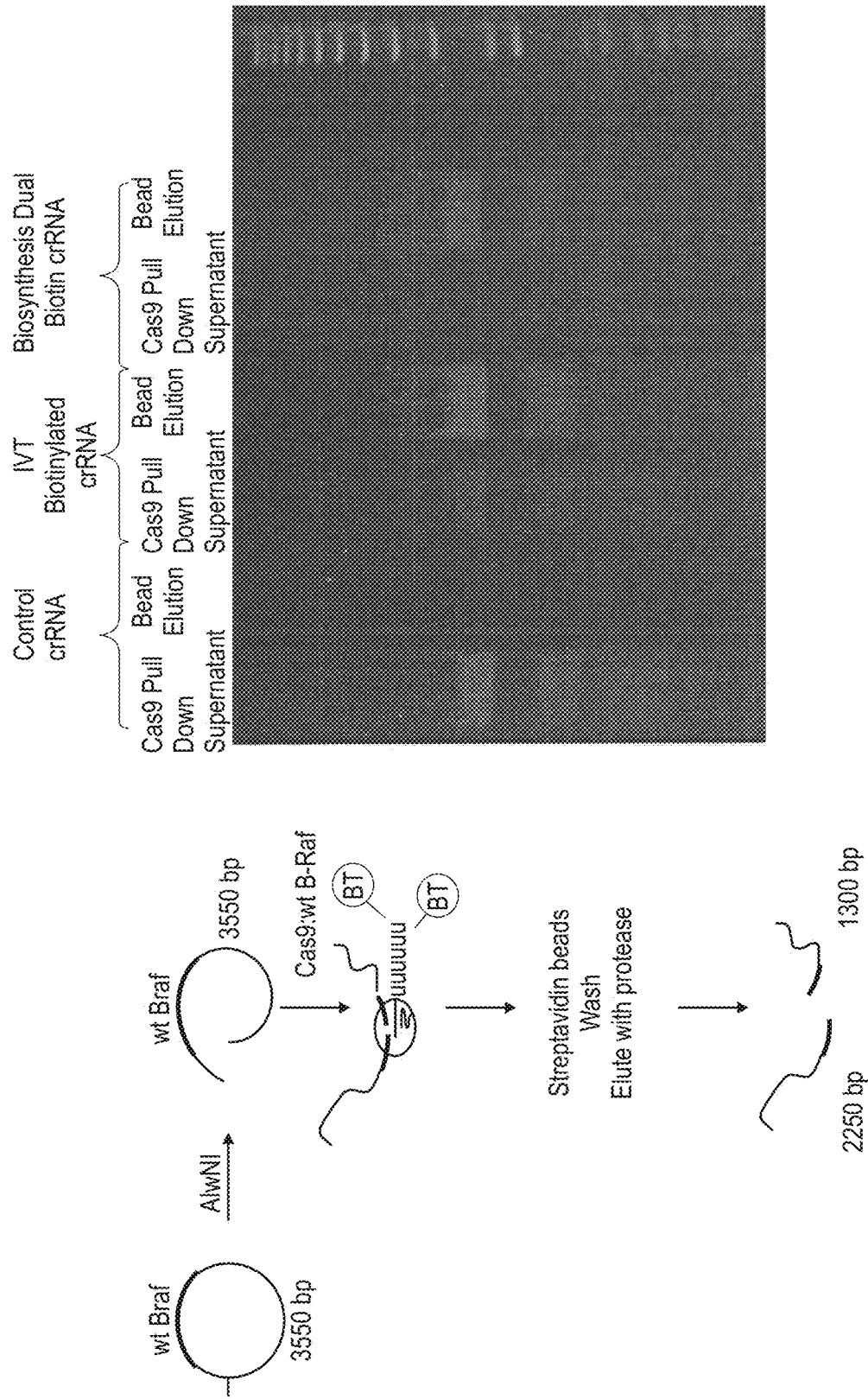
FIGS. 2A-2B exemplify a method provided herein for enriching a target DNA sequence (wild type Braf) using a CRISPR-Cas system containing a wild type Cas9 protein.
Figure 2B:
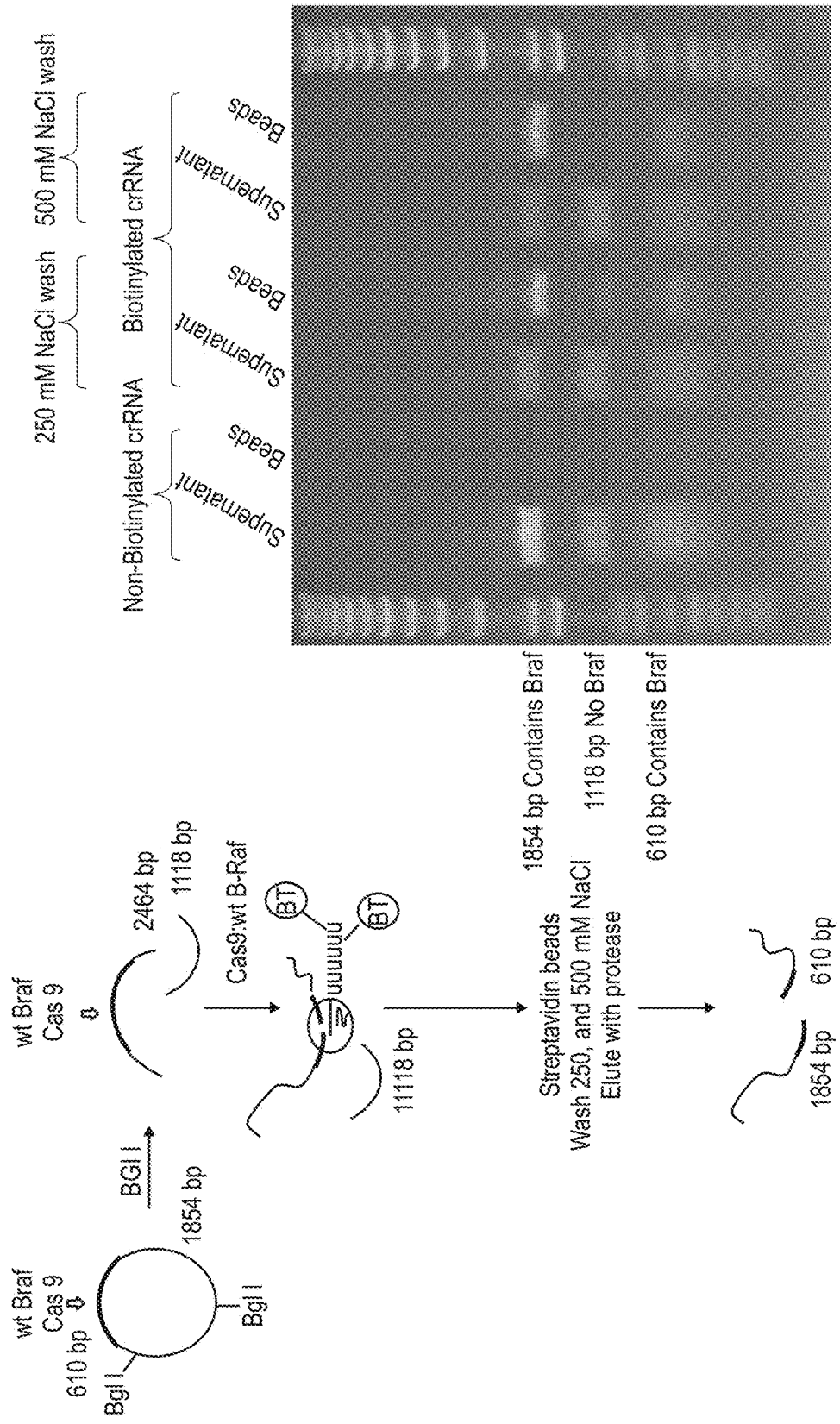

In some embodiments, the Cas9 protein or the variant thereof retains the two nuclease domains and is able to cleave opposite DNA strands and produce a double-stranded DNA break. The present method is partially based on a surprising discovery that wild-type Cas9 protein that retains the two nuclease domains can remain at the binding site following DNA cleavage with sufficient strength and length, so that to enable pulling down the DNA-endonuclease system complex through the endonuclease system. As illustrated in FIG. 2A-2B, the CRISPR-Cas system containing a wild type Cas9 protein is added to a solution containing a target Braf sequence. The system is labeled with biotinylated dUTP, and streptavidin beads are added to pull down the system with its associated DNA fragments. As shown in the right panel of FIG. 2A-2B, the cleaved DNA fragments are detected from the bead elution, indicating the association between the enzyme system and the DNA after the cleavage.

Figure 2C:
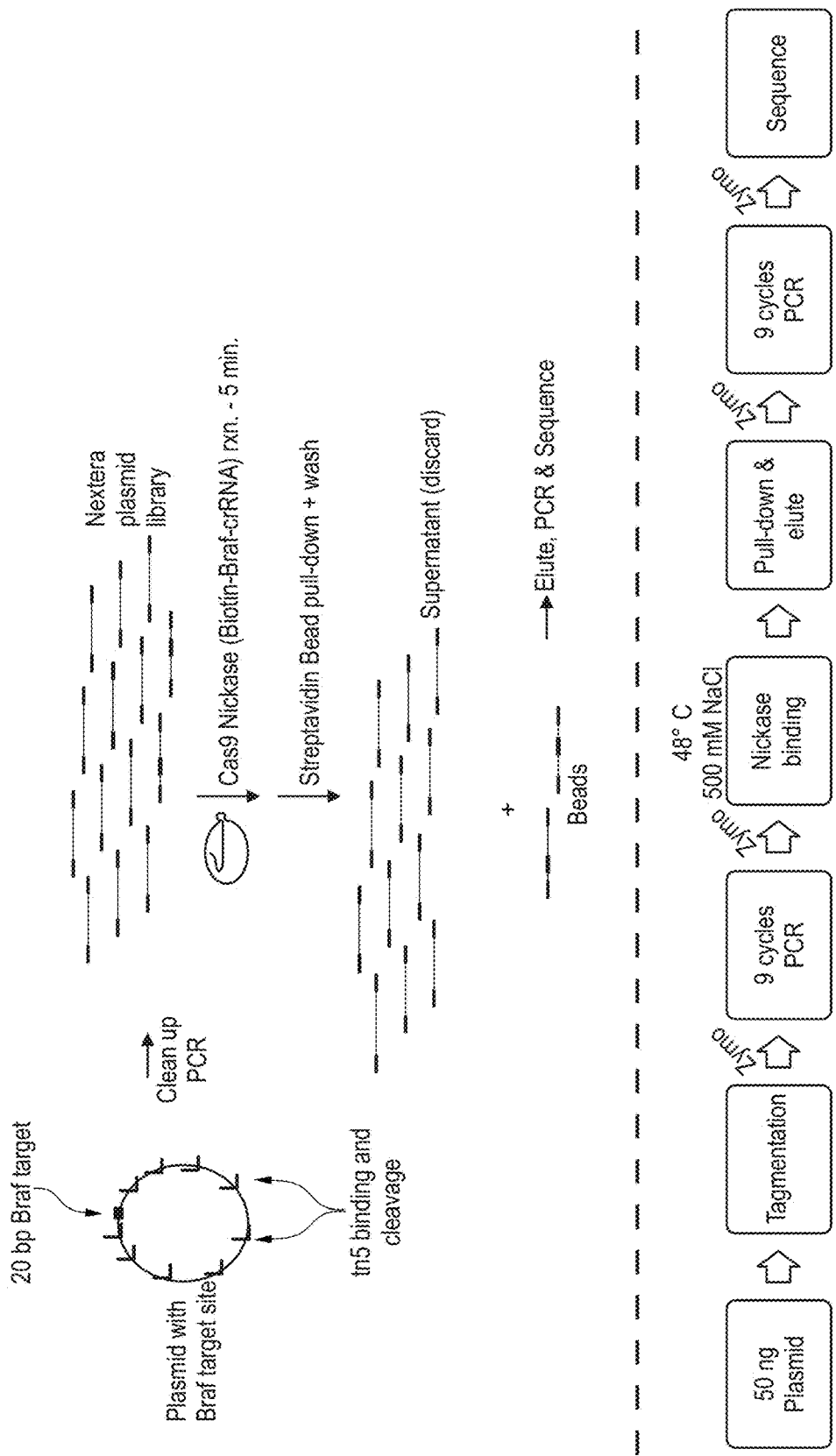
FIGS. 2C-2D exemplify a method provided herein for enriching a target DNA sequence (wild type Braf) using a CRISPR-Cas system containing a Cas9 nickase.

In other embodiments, the Cas9 protein or the variant thereof is a Cas9 nickase and is able to produce a single-stranded nucleic acid nick, e.g., a single-stranded DNA nick. A nickase variant of Cas9 protein stays with the target nucleic acid after creating a nick, and thus it can be used for target specific enrichment. In some embodiment, only RuvC-nuclease domain is mutated and inactivated. In some embodiments, only HNH-nuclease domain is mutated and inactivated. In some embodiments, the Cas9 protein contains one inactivated nuclease domain having a mutation in the domain that cleaves a target nucleic acid strand that is complementary to the crRNA. In one embodiment, the mutation is D10A. In some embodiments, the Cas9 protein contains one inactivated nuclease domain having a mutation in the domain that cleaves a target nucleic acid strand that is non-complementary to the crRNA. In one embodiment, the mutation is mutation is H840A. In some embodiments, the present method can be used to enrich a target nucleic acid fragment in a library of nucleic acid fragments, e.g., prepared using Illumina's Nextera library preparation. FIG. 2C illustrates a Cas9 nickase mediated enrichment of fragments prepared from a Nextera plasmid library. As shown, plasmids containing a Braf target site are first subject to Tn5 mediated tagmentation to result in a population of DNA fragments. Then CRISPR-Cas9 system containing a Cas9 nickase and a biotin labeled crRNA targeting to Braf sequence is added to the fragments. The CRISPR-Cas9 system specifically binds to the DNA fragments containing Braf sequence. By pulling down biotin and its associated components using Streptavidin beads, the DNA fragments containing Braf sequence are enriched. After eluted from the proteins, the enriched DNA fragments can be further subject to DNA amplification and sequencing.

In yet other embodiments, the Cas9 protein or the variant thereof is a nuclease-null variant of the Cas9 protein, in which both RuvC- and HNH-active sites/nuclease domains are mutated. A nuclease-null variant of the Cas9 protein binds to double-stranded DNA, but not cleave the DNA, and thus it can be used for target specific DNA enrichment too. In some embodiments, the Cas9 protein has two inactivated nuclease domains with a first mutation in the domain that cleaves the strand complementary to the crRNA and a second mutation in the domain that cleaves the strand non-complementary to the crRNA. In some embodiments, the Cas9 protein has a first mutation D10A and a second mutation H840A.

A target nucleic acid can be separated by pulling down its associated CRISPR-Cas system. In some embodiments, the endonuclease system is labeled, and the enzyme-nucleic acid complex is pulled down through the label. In some embodiments, the crRNA or the derivative thereof is labeled. In one embodiment, the crRNA is labeled with biotin, as described above. In other embodiments, the tracrRNA is labeled as described above. In other embodiments, the Cas protein or the variant thereof is labeled with a capture tag. The protein capture tag includes, but not limited to, GST, Myc, hemagglutinin (HA), Green fluorescent protein (GFP), flag, His tag, TAP tag, and Fc tag. Other protein capture tags, e.g., affinity tags, recognized in the art can also be used in the present methods. Those skilled in the art will recognize that a protocol chosen for the purification step will be specific to the tag used. In some embodiments, anti-Cas protein antibodies or fragments thereof, e.g., anti-Cas9 antibodies, can also be used to separate the complex.

In another aspect, binding of a guide RNA to a region of a target double-stranded nucleic acid disrupts the interaction between the two strands of the target nucleic acid, and thereby creates a loop structure exposing the strand non-complementary to the guide RNA. This exposed strand can be subjected to hybridization with another nucleotide probe as provided herein. One advantage provided by the method herein is double specificity for the enrichment—one from the crRNA and the other from the probe. In one embodiment, the present disclosure provides a method for enriching a target double-stranded nucleic acid including providing an endonuclease system having a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of a first strand of the target double-stranded nucleic acid; contacting the target double-stranded nucleic acid with the endonuclease system to form a first complex; hybridizing a labeled nucleic acid to a second strand of the target double-stranded nucleic acid to form a second complex, the second strand of the target double-stranded nucleic acid being non-complementary to the crRNA or the derivative thereof, and separating the second complex and thereby enriching for the target nucleic acid.

Figure 3:
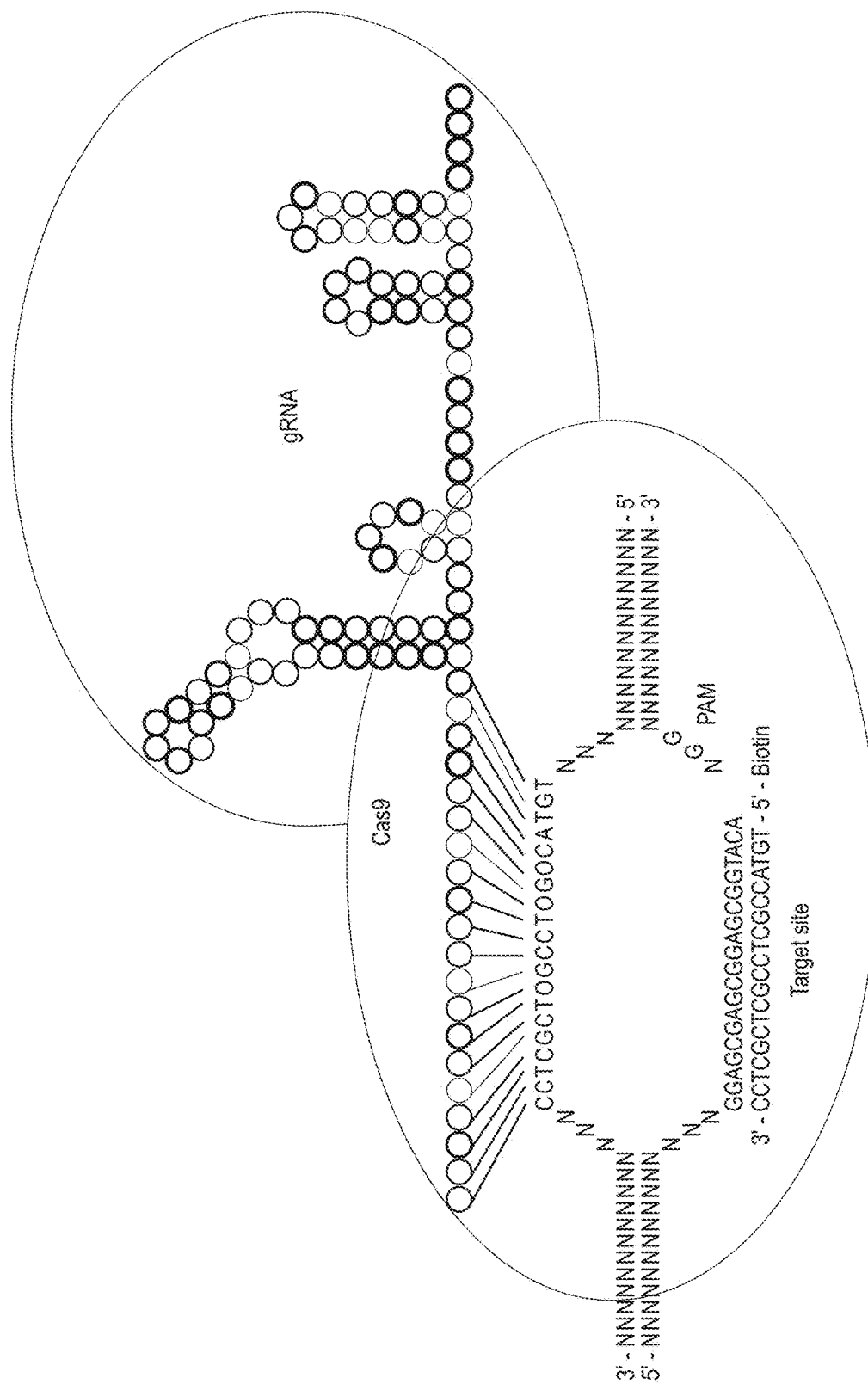
FIG. 3 is a schematic illustrating a method for enriching a target DNA sequencing using a CRISPR-Cas system, wherein the binding of the guide RNA with a strand of the target DNA creates a displacement loop for further labeling by a nucleic acid probe.

As illustrated in FIG. 3, crRNA (guide RNA or gRNA) hybridizes to one strand of a target double-stranded DNA to form a complex, and create a displacement loop. A labeled (e.g., biotin labeled) nucleic acid probe is provided, targeting this displacement loop and hybridizing to the other strand of the target double-stranded DNA, to form a labeled complex. The target double-stranded DNA can then be enriched by pulling down the labeled complex.

In some embodiments, the method of the present disclosure further includes separating the target double-stranded DNA sequence from the second complex. In some embodiments, the method the present application further includes amplifying the targeted double-stranded DNA sequence.

In some embodiments, the target nucleic acid provided herein is a double-stranded DNA (dsDNA). In some embodiments, the endonuclease system provided herein is a Type I CRISPR-Cas system or a derivative thereof. In some embodiments, the endonuclease system provided herein is a Type II CRISPR-Cas system. In some embodiments, the endonuclease system provided herein is a Type III CRISPR-Cas system or a derivative thereof. The CRISPR-Cas systems provided herein include engineered and/or programmed nuclease systems derived from naturally accruing CRISPR-Cas systems. CRISPR-Cas systems may include contain engineered and/or mutated Cas proteins. CRISPR-Cas systems may also contain engineered and/or programmed guide RNA.

In some embodiments, the crRNA or the derivative thereof contains a user-selectable RNA sequence that permits specific targeting of the enzyme to a complementary double-stranded DNA. In some embodiment, the user-selectable RNA sequence contains 20-50 nucleotides complementary or substantially complementary to a region of the target DNA sequence. In some embodiments, the target specific nucleotide region of the crRNA has 100% base pair matching with the region of the target nucleic acid. In some embodiments, the target specific nucleotide region of the crRNA has 90%-100%, 80%-100%, or 70%-100% base pair matching with the region of the target nucleic acid. In some embodiments, there is one base pair mismatch between the target specific nucleotide region of the crRNA and the region of the target nucleic acid. In some embodiments, there are two, three, four, or five base pair mismatches between the target specific nucleotide region of the crRNA and the region of the target nucleic acid.

In some embodiments, the endonuclease system provided herein further includes a trans-activating crRNA (tracrRNA) or a derivative thereof. In some embodiments, the crRNA or the derivative thereof provided herein is a polynucleotide having a crRNA polynucleotide fused to a tracrRNA polynucleotide. In one embodiment, the Cas protein or the variant thereof provided herein can be directed by a chimeric sgRNA to any genomic locus followed by a 5'-NGG protospacer-adjacent motif (PAM).

In some embodiments, the Cas protein or the variant thereof is a Cas9 protein or a variant thereof. In some embodiment, the Cas9 protein is derived from Cas9 protein of S. thermophilus CRISPR-Cas system. In some embodiment, the Cas9 protein is a multi-domain protein of about 1,409 amino acids residues.

In some embodiments, the Cas9 protein or the variant thereof retains the two nuclease domains and is able to cleave opposite DNA strands and produce a double-stranded DNA break. In other embodiments, the Cas9 protein or the variant thereof is a Cas9 nickase and is able to produce a single-stranded nucleic acid nick, e.g., a single-stranded DNA nick. In some embodiment, only RuvC-nuclease domain is mutated and inactivated. In some embodiments, only HNH-nuclease domain is mutated and inactivated. In some embodiments, the Cas9 protein contains one inactivated nuclease domain having a mutation in the domain that cleaves a target nucleic acid strand that is complementary to the crRNA. In one embodiment, the mutation is D10A. In some embodiments, the Cas9 protein contains one inactivated nuclease domain having a mutation in the domain that cleaves a target nucleic acid strand that is non-complementary to the crRNA. In one embodiment, the mutation is mutation is H840A. In yet other embodiments, the Cas9 protein or the variant thereof is a nuclease-null variant of the Cas9 protein, in which both RuvC- and HNH-active sites/nuclease domains are mutated. A nuclease-null variant of the Cas9 protein binds to double-stranded DNA, but not cleave the DNA, and thus it can be used for target specific DNA enrichment too. In some embodiments, the Cas9 protein has two inactivated nuclease domains with a first mutation in the domain that cleaves the strand complementary to the crRNA and a second mutation in the domain that cleaves the strand non-complementary to the crRNA. In some embodiments, the Cas9 protein has a first mutation D10A and a second mutation H840A.

In another aspect, the target nucleic acid can be fragmented and linked to an adaptor, preparing for other procedures such as sequencing. In some embodiments, the target nucleic acid is further subjected to a transposase mediated tagmentation that results in fragmentation of the target nucleic acid and ligation of adaptors to the 5' end of both strands of double-stranded DNA fragments. Optionally, the target nucleic acid can be fragmented and adaptors can be added to the 5' and 3' ends using tagmentation or transposition as described in U.S. Publication No. 2010/0120098, which is incorporated by reference herein in its entirety. Briefly, a transposition reaction is a reaction wherein one or more transposons are inserted into target nucleic acids at random sites. Essential components in a transposition reaction are a transposase and DNA oligonucleotides that exhibit the nucleotide sequences of a transposon, including the transferred transposon sequence and its complement (the non-transferred transposon end sequence) as well as other components needed to form a functional transposition or transposome complex. The DNA oligonucleotides can further include additional sequences (e.g., adaptor or primer sequences) as needed or desired. Exemplary transposition complexes, suitable for use in the methods provided herein, include, but are not limited to, those formed by a hyperactive Tn5 transposase and a Tn5-type transposon end or by a MuA transposase and a Mu transposon end comprising R1 and R2 end sequences (see, e.g., Goryshin and Reznikoff, *J. Biol. Chem.* 273: 7367, 1998; and Mizuuchi, *Cell* 35: 785, 1983; Savilahti et al., *EMBO J.* 14: 4893, 1995; which are incorporated by reference herein in their entireties). However, any transposition system that is capable of inserting a transposon end with sufficient efficiency to tag target nucleic acids for its intended purpose can be used in the provided methods. Other examples of known transposition systems that could be used in the provided methods include, but are not limited to, *Staphylococcus aureus* Tn552, Tyl, Transposon Tn7, Tn/O and IS10, Mariner transposase, Tel, P Element, Tn3, bacterial insertion sequences, retroviruses, and retrotransposon of yeast (see, e.g., Colegio et al., 2001, *J. Bacteriol.* 183: 2384-8; kirby et al., 2002, *Mol. Microbiol.* 43: 173-86; Devine and Boeke, 1994, *Nucleic Acids Res.*, 22: 3765-72; International Patent Application No. WO 95/23875; Craig, 1996, *Science* 271: 1512; Craig, 1996, Review in: *Curr Top Microbiol Immunol.* 204: 27-48; Kleckner et al., 1996, *Curr Top Microbiol Immunol.* 204: 49-82; Lampe et al., 1996, *EMBO J.* 15: 5470-9; Plasterk, 1996, *Curr Top Microbiol Immunol* 204: 125-43; Gloor, 2004, *Methods Mol. Biol.* 260: 97-114; Ichikawa and Ohtsubo, 1990, *J Biol. Chem.* 265: 18829-32; Ohtsubo and Sekine, 1996, *Curr. Top. Microbiol. Immunol.* 204: 1-26; Brown et al., 1989, *Proc Natl Acad Sci USA* 86: 2525-9; Boeke and Corces, 1989, *Annu Rev Microbiol.* 43: 403-34; which are incorporated herein by reference in their entireties). In some embodiments, the method of the present disclosure further comprises removing the transposase enzyme and adding to the ends of the adapted DNA fragments by PCR.

Figure 4A:
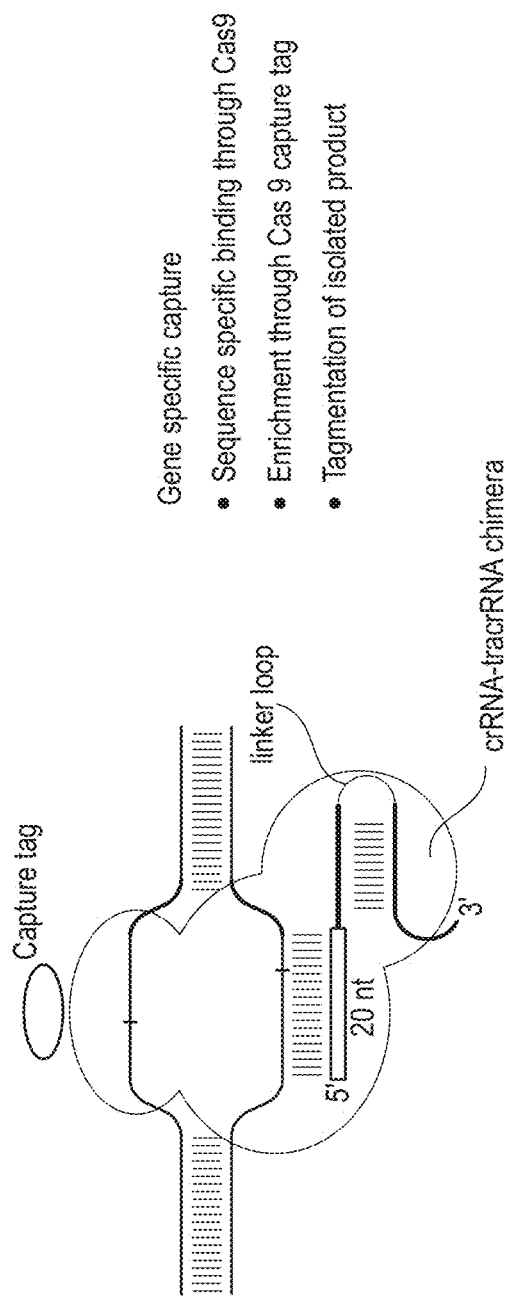
FIGS. 4A-4F illustrate methods provided herein further including tagmenting the target DNA.
Figure 4B:
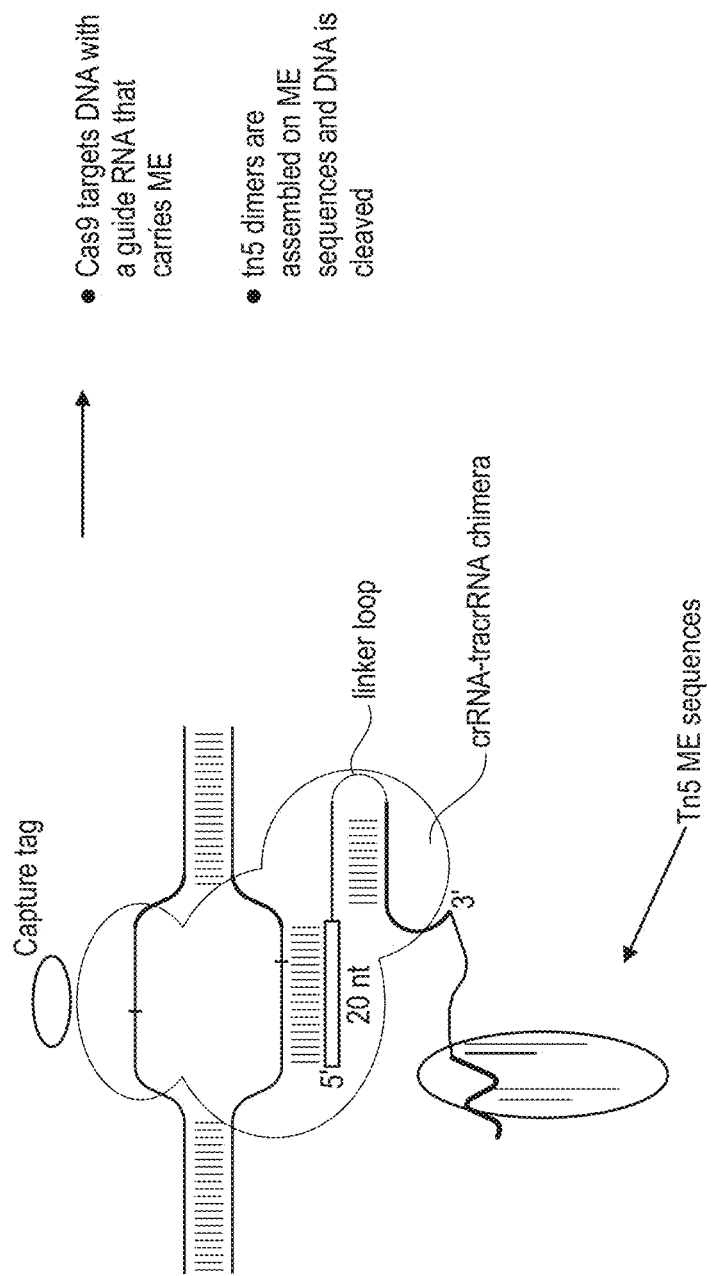
Figure 4C:
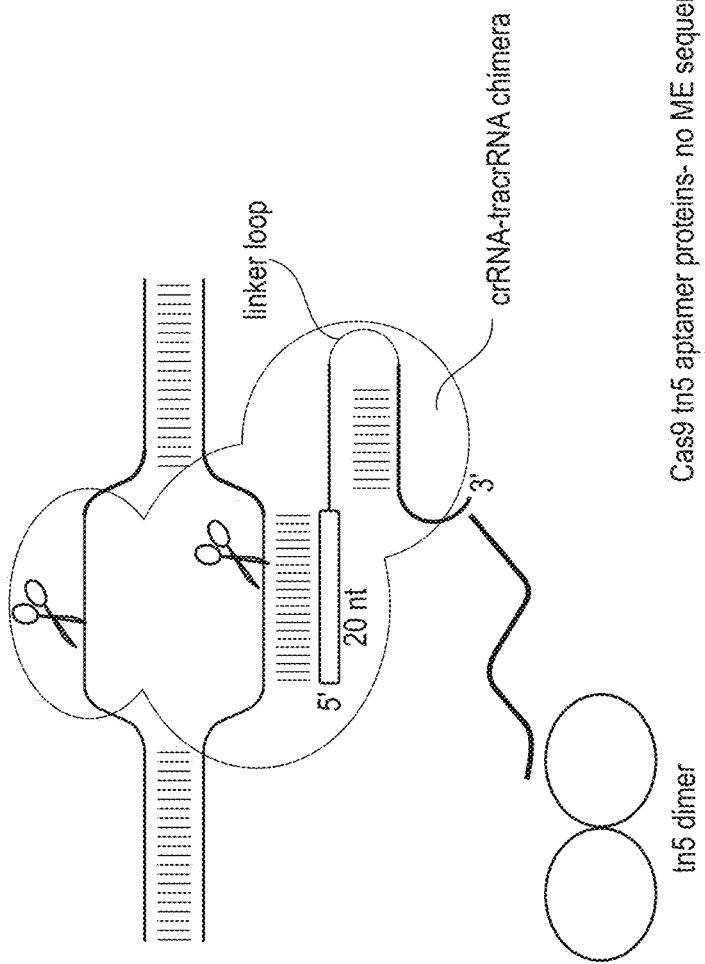
Figure 4D:
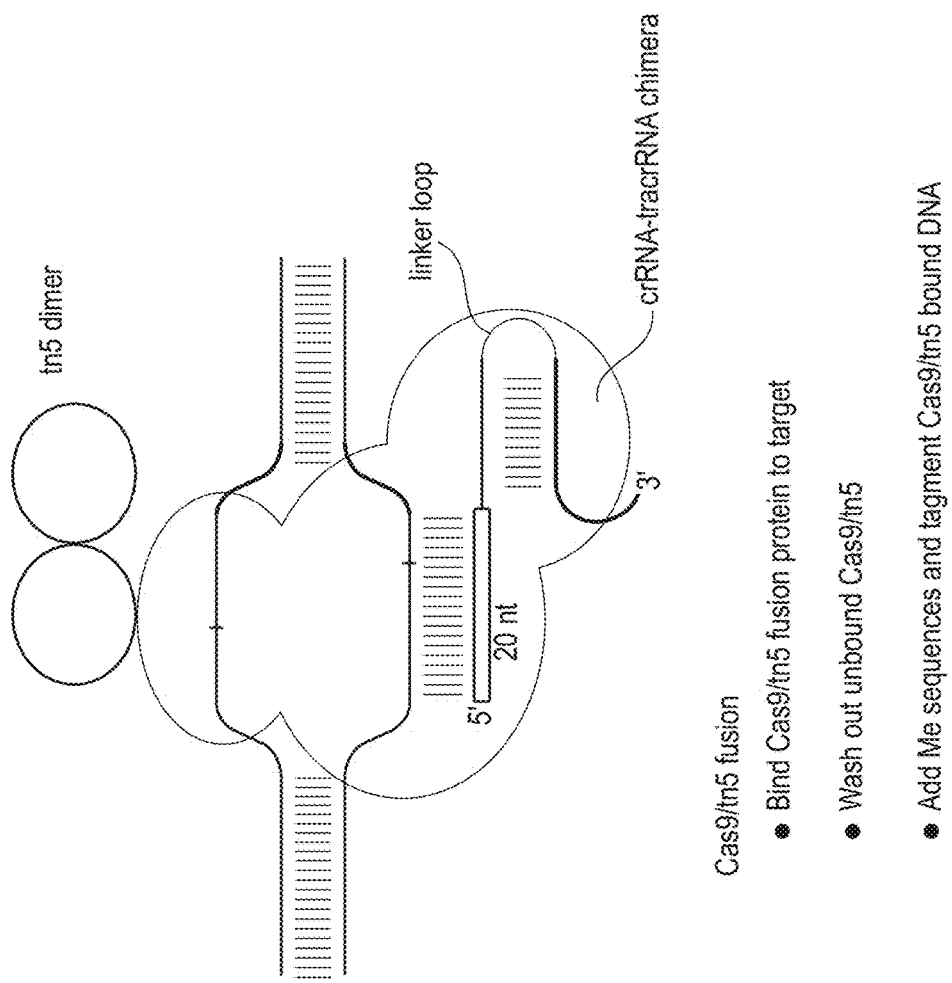

In some embodiments, the tagmentation is performed after the target nucleic acid is enriched. In one embodiment, as illustrated in FIGS. 4A and 4F, a CRISPR-Cas system containing a Cas9 protein and a crRNA-tracrRNA chimera is added and binds to a target DNA sequence to form a complex. The Cas9 protein is labeled with a capture tag, through which the complex is separated. The target DNA is then isolated from the complex and subject to tagmentation.

In some embodiments, a RNA in the CRISPR-Cas system, e.g., a crRNA or a derivative thereof, a sgRNA, and a tracrRNA or a derivative thereof, contains a transposon end, and the method of the present disclosure further includes adding a transposase. The added transposase can assemble on the transposon end and the target DNA is thereby cleaved by the transposase. In some embodiments, the transposon end is a mosaic end (ME), and the transposase is a Tn5 transposase. In one embodiment, as illustrated in FIG. 4B, the CRISPR-Cas system contains a labeled Cas9 protein and a crRNA-tracrRNA chimera carrying a transposon end (ME). The system is added and binds to a target DNA sequence to form a complex. A transposase (Tn5) is added and assembled on ME sequence, and thereby the DNA is cleaved.

In some embodiments, the endonuclease system provided herein further includes a transposase, and thus transposase is part of the endonuclease system, and the method of the present disclosure further includes adding transposon end to the target DNA sequence; and tagmenting the target DNA sequence by the transposase. In some embodiments, the transposase binds to a nucleotide sequence of the endonuclease system. In some embodiments, the transposase binds to a crRNA or a derivative thereof. In some embodiments, the transposase binds to a tracrRNA or a derivative thereof. In some embodiments, the transposase binds to a sgRNA or a chimeric polynucleotide having a crRNA polynucleotide and a tracrRNA polynucleotide. In some embodiments, the transposon end is a mosaic end (ME), and the transposase is a Tn5 transposase. As illustrated in FIG. 4C, in one embodiment, a transposase (Tn5) binds to the endonuclease system through an aptamer connected to the crRNA-tracrRNA chimera. Thus, Tn5 binds to the system without the assistance of ME sequences. The endonuclease system containing Tn5 is added and binds to the target DNA. ME sequences is then added to the DNA, and thus the DNA can be tagmented by Tn5. As illustrated in FIG. 4D, in another embodiment, the transposase provided herein and the Cas protein provided herein form a fusion protein. The endonuclease system containing Tn5 is added and binds to the target DNA. ME sequences is then added to the DNA, and thus the DNA can be tagmented by Tn5 and sequences, e.g., index or universal primer sequences, can be introduced.

Figure 4E:
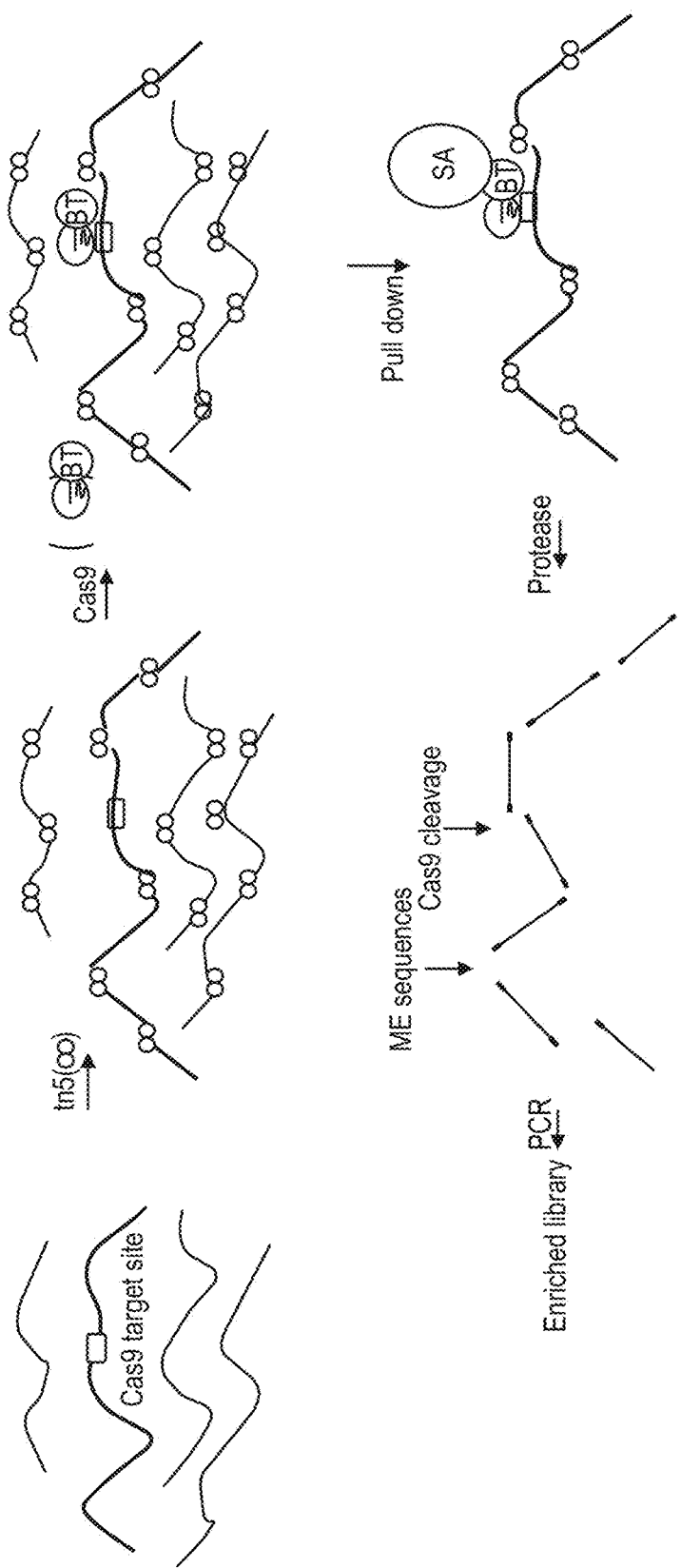
Figure 4F:
Figure 4F:
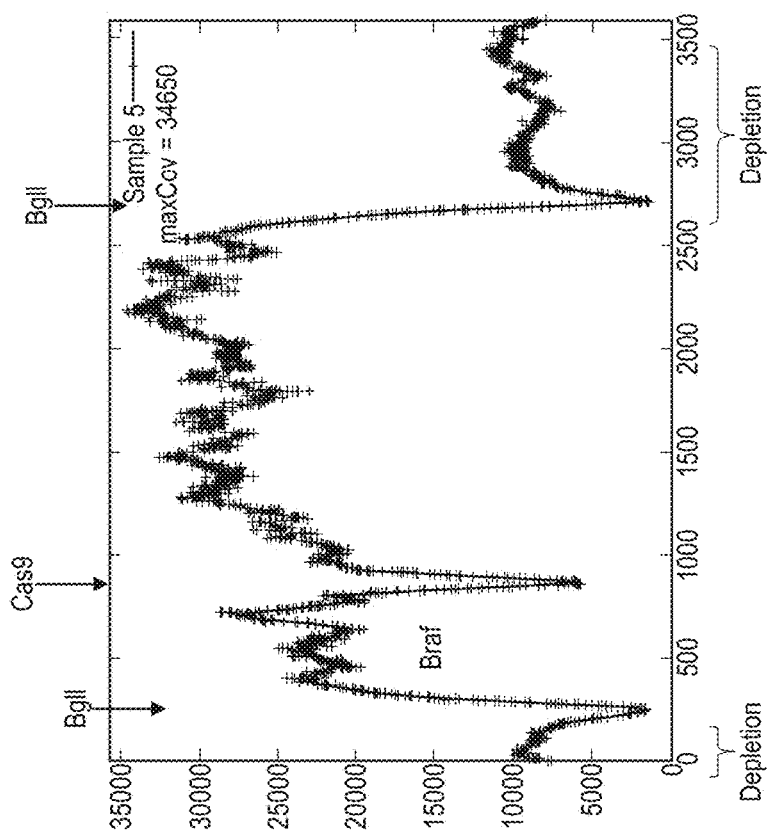

FIG. 4E illustrates a method of enriching a target nucleic acid using a method provided herein. As shown, a Tn5 system and a CRISPR-Cas9 system are added to a population of nucleic acid containing a target nucleic acid. CRISPR-Cas9 system contains a Cas9 with two nuclease domains. Thus, both the Tn5 system and the CRISPR-Cas9 system can cut nucleic acid, and after the cutting, both systems are staying with the cleaved ends of nucleic acid. The CRISPR-Cas9 system is labeled, through which the target nucleic acid can be pulled down. After treated with proteases, the DNA fragments generated from the target nucleic acid are released, and can be subject to further amplification and/or library preparation.

In another aspect, the present disclosure provides methods for enriching and/or detecting target nucleic acid in a population of cell free DNA using CRISPR-Cas systems. Cell free DNA in plasma or serum holds enormous potential as a non-invasive diagnostic tool in many areas of medicine. For example, cell free fetal DNA has been studied and even optimized for testing non-compatible RhD factors, sex determination for X-linked genetic disorders, testing for single gene disorders, identification of preeclampsia, and so on. For instance, sequencing the fetal cell fraction of cell free DNA in maternal plasma is a reliable approach for detecting copy number changes associated with fetal chromosome anueploidy. For another instance, sequencing cell free DNA isolated from cancer patients (also called circulating tumor DNA) has been used to detect mutations in key genes that have relevance for treatment decisions. The present disclosure provides methods for improving enriching and/or detecting target DNA sequences in cell free DNA.

In some embodiments, the present disclosure provides a method for enriching a target nucleic acid including obtaining a population of cell free DNA (cfDNA) from a subject's plasma or serum, the population of cell free DNA containing the target nucleic acid; providing an endonuclease system having a clustered regularly interspaced short palindromic repeats (CRISPR) RNA (crRNA) or a derivative thereof, and a CRISPR-associated (Cas) protein or a variant thereof, wherein the crRNA or the derivative thereof contains a target-specific nucleotide region complementary to a region of the target nucleic acid; contacting the target nucleic acid with the endonuclease system to form a complex, and separating the complex and thereby enriching for the target nucleic acid.

In some embodiments, the method provided herein further includes separating the target DNA sequence from the complex. In some embodiments, the method provided herein further includes amplifying the targeted DNA sequence. In some embodiments, the target nucleic acid provided herein is a double-stranded DNA (dsDNA).

In some embodiments, the endonuclease system provided herein is a Type I CRISPR-Cas system or a derivative thereof. In some embodiments, the endonuclease system provided herein is a Type II CRISPR-Cas system. In some embodiments, the endonuclease system provided herein is a Type III CRISPR-Cas system or a derivative thereof. The CRISPR-Cas systems provided herein include engineered and/or programmed nuclease systems derived from naturally accruing CRISPR-Cas systems. CRISPR-Cas systems may include contain engineered and/or mutated Cas proteins. CRISPR-Cas systems may also contain engineered and/or programmed guide RNA.

In some embodiments, the crRNA or the derivative thereof contains a user-selectable RNA sequence that permits specific targeting of the enzyme to a complementary double-stranded DNA. In some embodiment, the user-selectable RNA sequence contains 20-50 nucleotides complementary or substantially complementary to a region of the target DNA sequence. In some embodiments, the target specific nucleotide region of the crRNA has 100% base pair matching with the region of the target nucleic acid. In some embodiments, there is one base pair mismatch between the target specific nucleotide region of the crRNA and the region of the target nucleic acid. In some embodiments, there are two, three, four, or five base pair mismatches between the target specific nucleotide region of the crRNA and the region of the target nucleic acid.

In some embodiments, the endonuclease system provided herein further includes a trans-activating crRNA (tracrRNA) or a derivative thereof. In some embodiments, the crRNA or the derivative thereof provided herein is a polynucleotide having a crRNA polynucleotide fused to a tracrRNA polynucleotide. In one embodiment, the Cas protein or the variant thereof provided herein can be directed by a chimeric sgRNA to any genomic locus followed by a 5'-NGG protospacer-adjacent motif (PAM).

In some embodiments, the Cas protein or the variant thereof is a Cas9 protein or a variant thereof. In some embodiment, the Cas9 protein is derived from Cas9 protein of S. thermophilus CRISPR-Cas system. In some embodiment, the Cas9 protein is a multi-domain protein of about 1,409 amino acids residues.

In some embodiments, the Cas9 protein or the variant thereof retains the two nuclease domains and is able to cleave opposite DNA strands and produce a double-stranded DNA break. In other embodiments, the Cas9 protein or the variant thereof is a Cas9 nickase and is able to produce a single-stranded nucleic acid nick, e.g., a single-stranded DNA nick. In some embodiment, only RuvC-nuclease domain is mutated and inactivated. In some embodiments, only HNH-nuclease domain is mutated and inactivated. In some embodiments, the Cas9 protein contains one inactivated nuclease domain having a mutation in the domain that cleaves a target nucleic acid strand that is complementary to the crRNA. In one embodiment, the mutation is D10A. In some embodiments, the Cas9 protein contains one inactivated nuclease domain having a mutation in the domain that cleaves a target nucleic acid strand that is non-complementary to the crRNA. In one embodiment, the mutation is mutation is H840A. In yet other embodiments, the Cas9 protein or the variant thereof is a nuclease-null variant of the Cas9 protein, in which both RuvC- and HNH-active sites/nuclease domains are mutated. A nuclease-null variant of the Cas9 protein binds to double-stranded DNA, but not cleave the DNA, and thus it can be used for target specific DNA enrichment too. In some embodiments, the Cas9 protein has two inactivated nuclease domains with a first mutation in the domain that cleaves the strand complementary to the crRNA and a second mutation in the domain that cleaves the strand non-complementary to the crRNA. In some embodiments, the Cas9 protein has a first mutation D10A and a second mutation H840A.

In some embodiments, the target DNA is in a fetal cell faction of the cell free DNA, and the cell free DNA is from maternal plasma. Protocols for extracting cell free fetal DNA are known in the art (see. e.g., Li et al., 2004, *Clinical Chemistry* 50 (6): 1002-1011; and Li et al., 2005, *The Journal of the American Medical Association* 293 (7): 843-849, which are incorporated herein by reference in their entireties). Many protocols for extracting the fetal DNA from the maternal plasma use the size of the fetal DNA to distinguish it from the maternal DNA. Typical steps for isolation of plasma from maternal blood include centrifugation, followed by isolation and purification of cell-free DNA (see, e.g., Chiu et al., 2001, *Clinical Chemistry* 47 (9): 1607-1613). Optionally, protocol developed by Legler et al. can be used for extracting cell free fetal DNA (see Legler et al. 2007, *Prenatal Diagnosis* 27 (9): 824-829). Optionally, formaldehyde can be added to maternal blood samples to increase the percentage of cell free fetal DNA. It has been shown that formaldehyde can stabilize intact cells, and inhibit further release of maternal DNA (see, e.g., Dhallan et al. 2004, *The Journal of the American Medical Association* 291 (9): 1114-1119).

In some embodiments, the subject is a cancer patient. A tumor itself is usually the major source of tumor DNA. However, acquiring DNA through a biopsy is invasive and risky if possible at all. Cell-free circulating tumor DNA in the bloodstream released from dying tumor cells provides another useful tool for detecting somatic mutation present in the tumors. Cell free circulating tumor DNA with mutations has been identified in many types of cancers at both early stage and advanced stage. In addition, the amount of cell free circulating DNA has been shown to increase as the cancer advances. Accordingly, cell free circulating DNA can also be used as a way of monitoring tumor progression and testing whether a patient's tumor would respond to targeted drug treatments (see, e.g., Bettegowda et al., 2014, *Sci. Transl. Med*, 6(224): 24). The present disclosure provides a method for enriching and/or detecting a target DNA sequence in the cell free circulating DNA from a cancer patient. In one embodiment, the cancer patient has pancreatic, ovarian, colorectal, bladder, gastroesophageal, breast, melanoma, hepatocellular, or head and neck cancer. In some embodiments, the cancer patient has brain, renal, prostate, or thyroid cancer. In some embodiments, the cancer patient has carcinoma. In some embodiments, the cancer patient has sarcoma. In some embodiments, the cancer patient has a lymphoma or leukemia. In some embodiments, the method provided herein is used to diagnose a cancer. In some embodiments, the method provided herein is used to monitor tumor progression and/or test a tumor patient's response to targeted drug treatments.

In some embodiments, the target nucleic acid contains a single nucleotide variant (SNV). In some embodiments, the SNV contains a single nucleotide polymorphism (SNP). In some embodiments, the SNV contains a point mutation. Single nucleotide polymorphism (SNP) is a common type of genetic variation which includes polymorphism in a DNA position at which two or more alternative bases occur at appreciable frequency in the people population (usually more than or equal to 1%). Point mutations are base variations with the frequency less than 1%. Single nucleotide polymorphism (SNP) and point mutations represent the largest source of diversity in the genome of a human. These single nucleotide polymorphisms (SNP) and point mutations can serve as biological markers for locating a disease on the human genome map because they are usually located near a gene associated with a certain disease. Thus, detection of single nucleotide polymorphisms (SNPs), point mutations, and similar mutations are of great importance to clinical activities, human health, and control of genetic disease. Detection of fetal or cancer related SNV by sequencing cell free DNA can be difficult since these variants often are present at a very low percentage of total cell free DNA (typically 0.1% and below). One advantage provided by the present disclosure is a more sensitive method for detecting and/or enriching a DNA sequence having SNV. In one embodiment, the method of the present disclosure allows detection of SNV present in a cell free DNA sample in the 0.1% to 0.01% frequency range. In one embodiment, the method provided herein enriches and/or detects SNV present in a cell free DNA sample in the 0.01% to 0.05% frequency range. In some embodiments, the method provided herein enriches and/or detects SNV present in a cell free DNA sample at about 0.01%, 0.02%, 0.03%, 0.04%, 0.05%, 0.06%, 0.07%, 0.08%, 0.09%, or 0.1% frequency.

Figure 5:
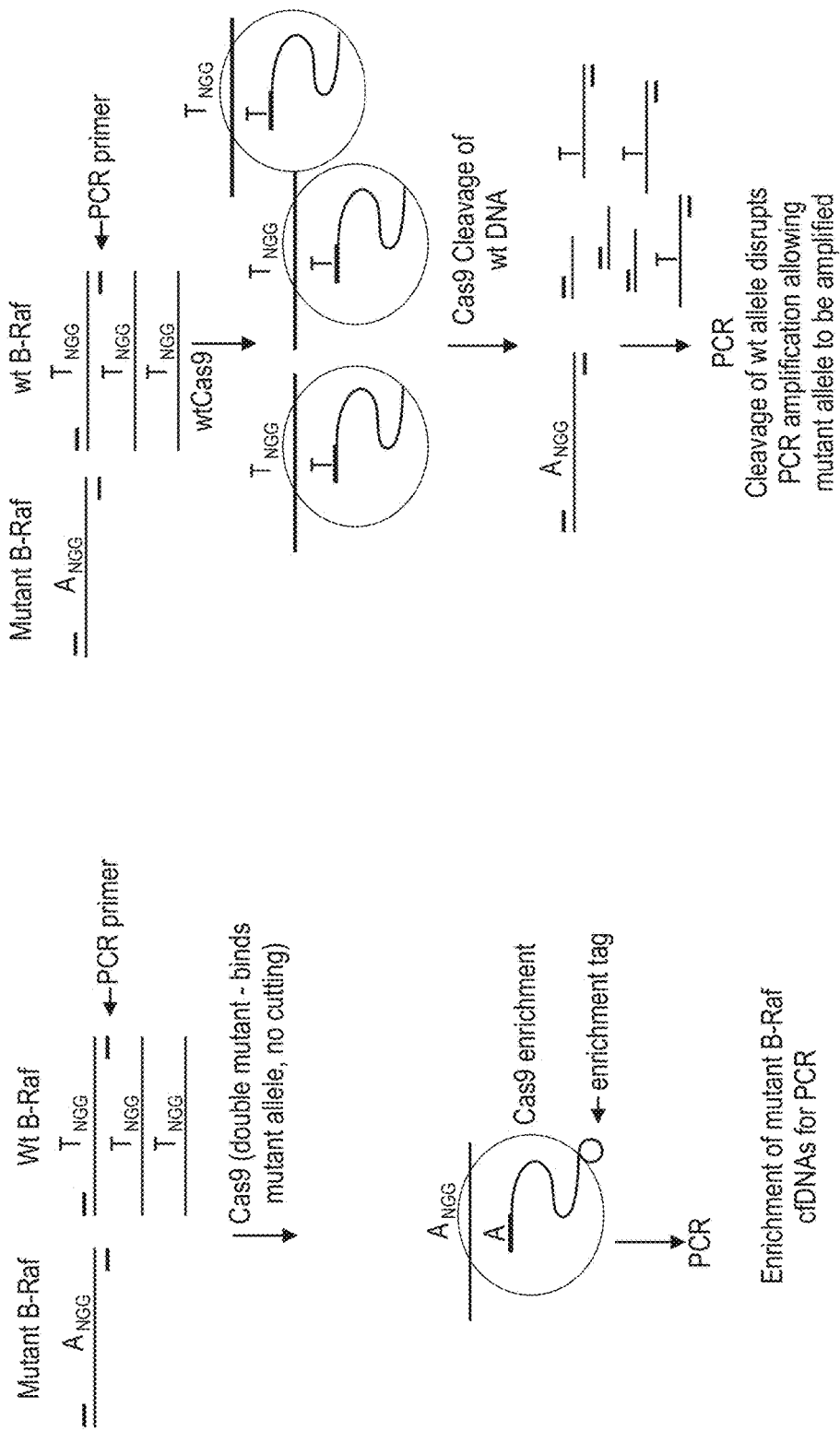
FIG. 5 is a schematic illustrating methods of enriching and detecting polynucleotide variants.

By way of example but not limitation, enrichment of rare mutant alleles (B-Raf V600E) in the presence of an excess of wild type allele (B-Raf) is illustrated in FIG. 5. In one embodiment, as illustrated in the left panel of FIG. 5, prior to use, the CRISPR-Cas system is modified with a tag such as biotin to facilitate recovery of bound target DNA. The CRISPR-Cas system is programmed to contain a nuclease-null variant of the Cas9 protein and a guide RNA that has a sequence complementary to the mutant allele (B-Raf V600E). The mutant allele B-RAF V600E is mixed with purified cell free DNA containing an excess amount of wild type allele DNA fragments. The CRISPR-Cas system is added to the mixture containing mutant alleles (B-Raf V600E) and an excess of wild type allele (B-Raf). The CRISPR-Cas system specifically binds to the polynucleotide containing the mutant allele (B-Raf V600E) to form a complex but the enzyme does not cleave the DNA. The complex is pulled out from the mixture using streptavidin coated beads. The mutant allele (B-Raf V600E) is then separated from the complex. Following wash, enriched DNA bearing the mutant allele is amplified by PCR using primer sets that flank the V600E allele site. Amplicons can then be sequenced.

As an alternative to direct enrichment of the target nucleic acid sequence containing SNV, the present disclosure also provides a method for enriching nucleic acid sequence containing SNV by destroying other genotypes or polynucleotides that do not contain SNV using CRISPR-Cas systems. In some embodiments, the present disclosure provides a method for detecting single nucleotide variant (SNV) including obtaining a population of cell free DNA from a subject's plasma or serum; providing a first endonuclease system having a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a first target-specific nucleotide region complementary to a region of a first target nucleic acid, and wherein the first Cas protein has nuclease activity; cleaving the first target nucleic acid using the endonuclease system; and amplifying a second target nucleic acid using Polymerase Chain Reaction (PCR), wherein the the second target nucleic acid contains a single nucleotide variant version of the first target nucleic acid.

As illustrated in the right panel of FIG. 5, rather than using a guide RNA complementary to mutant allele, a guide RNA complementary to wild type allele (B-Raf) is used. In addition, the Cas9 protein retains the nuclease activity in both nuclease domains. As a result, the CRISPR-Cas system binds to wild type allele and cleaves it. Because the system makes a double stranded break in the wild type allele sequences, these sequences cannot not be served as templates for subsequent PCR reactions. As such, only cell free DNA that bears mutant allele will serve as the template and be amplified.

In some embodiments, the second target nucleic acid provided herein is a double-stranded DNA (dsDNA).

In some embodiments, the first endonuclease system provided herein is a Type I CRISPR-Cas system or a derivative thereof. In some embodiments, the endonuclease system provided herein is a Type II CRISPR-Cas system. In some embodiments, the endonuclease system provided herein is a Type III CRISPR-Cas system or a derivative thereof. The CRISPR-Cas systems provided herein include engineered and/or programmed nuclease systems derived from naturally accruing CRISPR-Cas systems. CRISPR-Cas systems may include contain engineered and/or mutated Cas proteins. CRISPR-Cas systems may also contain engineered and/or programmed guide RNA.

In some embodiments, the first crRNA or the derivative thereof contains a user-selectable RNA sequence that permits specific targeting of the enzyme to a complementary double-stranded nucleic acid. In some embodiment, the user-selectable RNA sequence contains 20-50 nucleotides complementary to a region of the first target DNA sequence. In some embodiments, the first target specific nucleotide region of the crRNA has 100% base pair matching with the region of first the target nucleic acid. In some embodiments, there is one base pair mismatch between the first target specific nucleotide region of the crRNA and the region of the first target nucleic acid. In some embodiments, there are two, three, four, or five base pair mismatches between the first target specific nucleotide region of the crRNA and the region of the first target nucleic acid.

In some embodiments, the first endonuclease system provided herein further includes a trans-activating crRNA (tracrRNA) or a derivative thereof. In some embodiments, the first crRNA or the derivative thereof provided herein is a polynucleotide having a crRNA polynucleotide fused to a tracrRNA polynucleotide. In one embodiment, the first Cas protein or the variant thereof provided herein can be directed by a chimeric sgRNA to any genomic locus followed by a 5'-NGG protospacer-adjacent motif (PAM).

In some embodiments, the first Cas protein or the variant thereof is a Cas9 protein or a variant thereof. In some embodiment, the Cas9 protein is derived from Cas9 protein of *S. thermophilus* CRISPR-Cas system. In some embodiment, the Cas9 protein is a multi-domain protein of about 1,409 amino acids residues. In some embodiments, the Cas9 protein or the variant thereof retains the two nuclease domains and is able to cleave opposite DNA strands and produce a double-stranded DNA break.

In some embodiments, the second target nucleic acid contains a single nucleotide variant (SNV). In some embodiments, the SNV contains a single nucleotide polymorphism (SNP). In some embodiments, the SNV contains a point mutation. In one embodiment, the method of the present disclosure allows detection of SNV present in a cell free DNA sample in the 0.1% to 0.01% frequency range. In one embodiment, the method provided herein enriches and/or detects SNV present in a cell free DNA sample in the 0.01% to 0.05% frequency range. In some embodiments, the method provided herein enriches and/or detects SNV present in a cell free DNA sample at about 0.01%, 0.02%, 0.03%, 0.04%, 0.05%, 0.06%, 0.07%, 0.08%, 0.09%, or 0.1% frequency.

Alternatively, two endonuclease systems can be provided: the first endonuclease system is used to digest the nucleic acid that does not contain SNV, and the second endonuclease system is used to pull down the nucleic acid with SNV. In some embodiments, the method herein further includes providing a second endonuclease system having a second clustered regularly interspaced short palindromic repeats (CRISPR) RNA (crRNA) or a derivative thereof, and a second CRISPR-associated (Cas) protein or a variant thereof, wherein the second crRNA or the derivative thereof contains a second target-specific nucleotide region complementary to a region of the second target nucleic acid; contacting the second target nucleic acid with the second endonuclease system to form a complex, and separating the complex and thereby enriching for the second target nucleic acid.

In some embodiments, the method provided herein further includes separating the second target nucleic acid from the complex. In some embodiments, the second target nucleic acid provided herein is a double-stranded DNA (dsDNA).

In some embodiments, the second endonuclease system provided herein is a Type I CRISPR-Cas system or a derivative thereof. In some embodiments, the second endonuclease system provided herein is a Type II CRISPR-Cas system. In some embodiments, the second endonuclease system provided herein is a Type III CRISPR-Cas system or a derivative thereof. The CRISPR-Cas systems provided herein include engineered and/or programmed nuclease systems derived from naturally accruing CRISPR-Cas systems. CRISPR-Cas systems may include contain engineered and/or mutated Cas proteins. CRISPR-Cas systems may also contain engineered and/or programmed guide RNA.

In some embodiments, the second crRNA or the derivative thereof contains a user-selectable RNA sequence that permits specific targeting of the enzyme to a complementary double-stranded DNA. In some embodiment, the user-selectable RNA sequence contains 20-50 nucleotides complementary or substantially complementary to a region of the target DNA sequence. In some embodiments, the target specific nucleotide region of the crRNA has 100% base pair matching with the region of the target nucleic acid. In some embodiments, there is one base pair mismatch between the target specific nucleotide region of the crRNA and the region of the target nucleic acid. In some embodiments, there are two, three, four, or five base pair mismatches between the target specific nucleotide region of the crRNA and the region of the target nucleic acid.

In some embodiments, the second endonuclease system provided herein further includes a trans-activating crRNA (tracrRNA) or a derivative thereof. In some embodiments, the crRNA or the derivative thereof provided herein is a polynucleotide comprising a crRNA polynucleotide fused to a tracrRNA polynucleotide.

In some embodiments, the second Cas protein or the variant thereof is a Cas9 protein or a variant thereof. In some embodiment, the Cas9 protein is derived from Cas9 protein of *S. thermophilus* CRISPR-Cas system. In some embodiment, the Cas9 protein is a multi-domain protein of about 1,409 amino acids residues.

In some embodiments, the Cas9 protein or the variant thereof retains the two nuclease domains and is able to cleave opposite DNA strands and produce a double-stranded DNA break. In other embodiments, the Cas9 protein or the variant thereof is a Cas9 nickase and is able to produce a single-stranded nucleic acid nick, e.g., a single-stranded DNA nick. In some embodiment, only RuvC-nuclease domain is mutated and inactivated. In some embodiments, only HNH-nuclease domain is mutated and inactivated. In some embodiments, the Cas9 protein contains one inactivated nuclease domain having a mutation in the domain that cleaves a target nucleic acid strand that is complementary to the crRNA. In one embodiment, the mutation is D10A. In some embodiments, the Cas9 protein contains one inactivated nuclease domain having a mutation in the domain that cleaves a target nucleic acid strand that is non-complementary to the crRNA. In one embodiment, the mutation is mutation is H840A. In yet other embodiments, the Cas9 protein or the variant thereof is a nuclease-null variant of a Cas9 protein, in which both RuvC- and HNH-active sites/nuclease domains are mutated. In some embodiments, the Cas9 protein has two inactivated nuclease domains with a first mutation in the domain that cleaves the strand complementary to the crRNA and a second mutation in the domain that cleaves the strand non-complementary to the crRNA. In some embodiments, the Cas9 protein has a first mutation D10A and a second mutation H840A.

In some embodiments, the second target nucleic acid is in a fetal cell faction of the cell free DNA, and the cell free DNA is from maternal plasma. In some embodiments, the subject is a cancer patient. In one embodiment, the cancer patient has pancreatic, ovarian, colorectal, bladder, gastroesophageal, breast, melanoma, hepatocellular, or head and neck cancer. In some embodiments, the cancer patient has brain, renal, prostate, or thyroid cancer. In some embodiments, the cancer patient has carcinoma. In some embodiments, the cancer patient has sarcoma. In some embodiments, the cancer patient has a lymphoma or leukemia. In some embodiments, the method provided herein is used to diagnose a cancer. In some embodiments, the method provided herein is used to monitor tumor progression and/or test a tumor patient's response to targeted drug treatments.

In yet another aspect, the present disclosure provides a method for labeling a target nucleic acid sequence using CRISPR-Cas system containing a nickase. The nickase provided herein can introduce target specific nicks to the double-stranded nucleic acid. The nicks can be further used to insert capture tags, such as biotinylated dNTP, oligo probes, or double-stranded nucleic acid adapters, for enrichment strategies of the target nucleic acid. The current methods of a single-stranded nucleic acid enrichment schemes requires generating a "tree structure" of hybridized products, and such structure usually reduces specificity. The method provided herein directly targets to double-stranded nucleic acid and thus circumvents the need of creating such a "tree structure." In addition, the method provided here enables enrichment of long nucleic acid fragments.

In some embodiments, the method provided herein includes generating one single-stranded nick, and from this nick a nick translation is performed to introduce a capture label for recovering the target nucleic acid. In other embodiments, the method provided herein includes generating two consecutive single-stranded nicks on the same strand of the target nucleic acid. The single-stranded nucleic acid product between the two nicks can be replaced with a capture label for recovering the target nucleic acid. In yet other embodiments, the method provided herein includes generating two consecutive single-stranded nicks on the opposite strands of the target nucleic acid, and thus generate a double-stranded nucleic acid break that can be linked to an adapter for enrichment.

In some embodiment, the present disclosure provides a method for labeling a target nucleic acid including providing a first nuclease system having a first clustered regularly interspaced short palindromic repeats (CRISPR) RNA (crRNA) or a derivative thereof, and a first CRISPR-associated (Cas) protein or a variant thereof, wherein the first crRNA or the derivative thereof contains a first target-specific nucleotide region complementary to a first region of the target nucleic acid, and wherein the first Cas protein contains one inactivated nuclease domain; contacting a double-stranded nucleic acid containing the target nucleic acid with the first nuclease system to generate a first single-stranded nick at the first region of the target nucleic acid, and labeling the target nucleic acid. In some embodiments, the method herein further includes separating the target nucleic acid through the labeling and thereby enriching the target nucleic acid. In some embodiments, the method provided herein further includes amplifying the target nucleic acid.

Figure 6A:
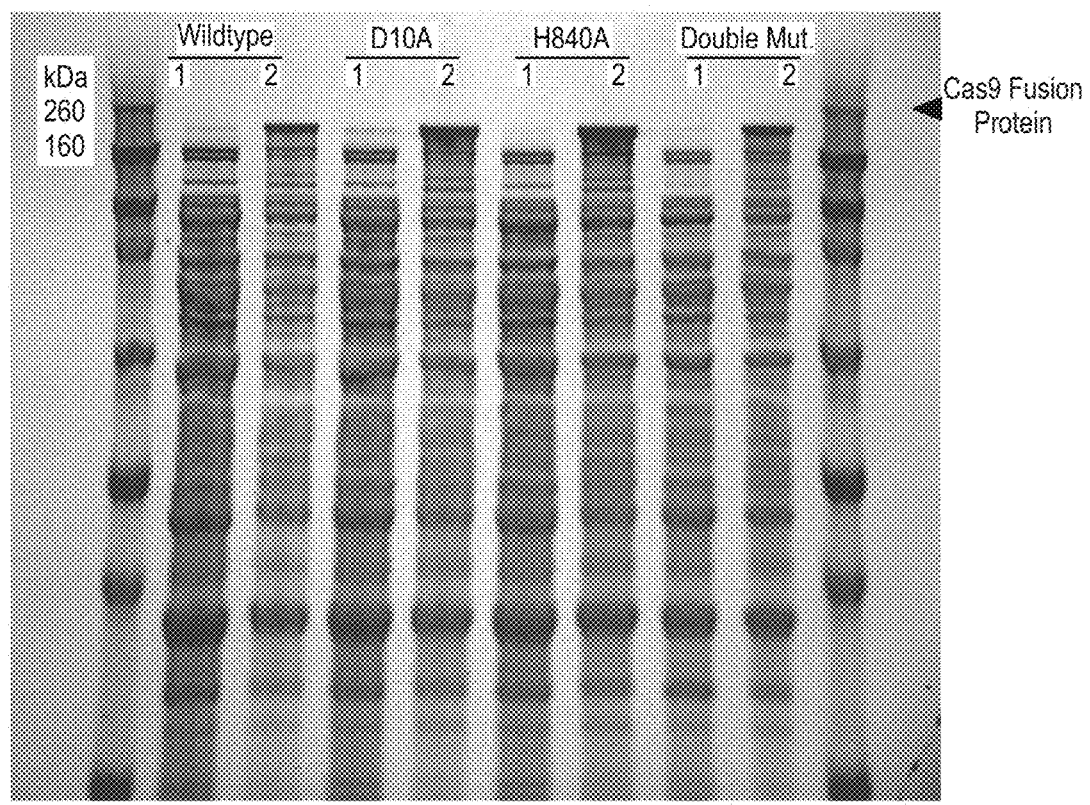
FIG. 6A shows the expressions of the Cas9 fusion proteins.
Figure 6B:
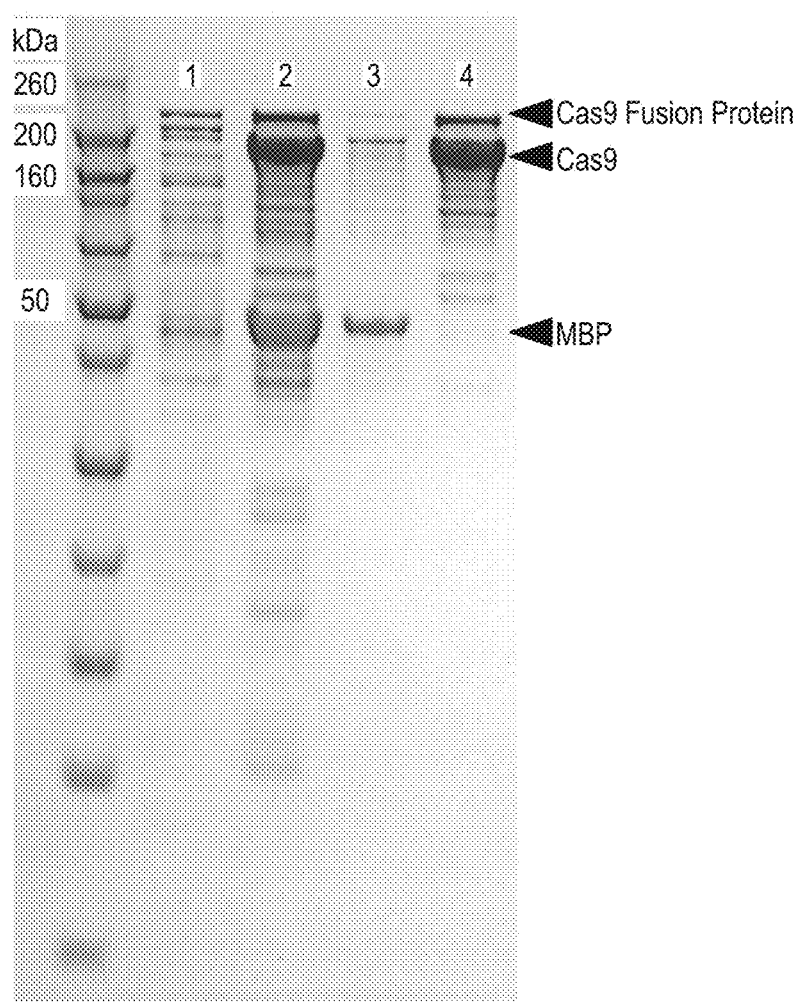
FIG. 6B exemplifies purification of a Cas9 nickase (m10).

In some embodiments, the first nuclease system provided herein further includes a trans-activating crRNA (tracrRNA). In some embodiments, the first crRNA or the derivative thereof provided herein is a polynucleotide having a crRNA polynucleotide fused to a tracrRNA polynucleotide. In some embodiments, the first nuclease system provided herein is a Type II CRISPR-Cas system or a derivative thereof. In some embodiments, the first Cas protein or the variant thereof is a Cas9 protein or a variant thereof. In some embodiments, the Cas9 protein or the variant thereof contains one inactivated nuclease domain with a mutation in the domain that cleaves a target nucleic acid strand that is complementary to the first crRNA. In some embodiments, the mutation is D10A. In some embodiments, the first Cas9 protein or the variant thereof contains one inactivated nuclease domain with a mutation in the domain that cleaves a target nucleic acid strand that is non-complementary to the first crRNA. In some embodiments, the mutation is H840A. As illustrated in FIGS. 6A-6B, purified Cas9 nickase possesses sequence specific nicking activity.

In some embodiments, the method of the present disclosure further includes performing a nick translation. In some embodiments, the nick translation provided herein is performed by using a nick translation polymerase selected from a group consisting of DNA Pol 1, Bst, and Taq. Other nick translation polymerases known in the art are also included in the method provided herein. In some embodiments, the nick translation provided herein is performed in a reaction mixture containing biotinylated dNTPs. In some embodiments, the biotinylated dNTPs provided herein are biotinylated dUTPs. In some embodiments, the method of the present disclosure further includes adding magnetic streptavidin beads to enrich biotinylated target DNA.

Figure 7A:
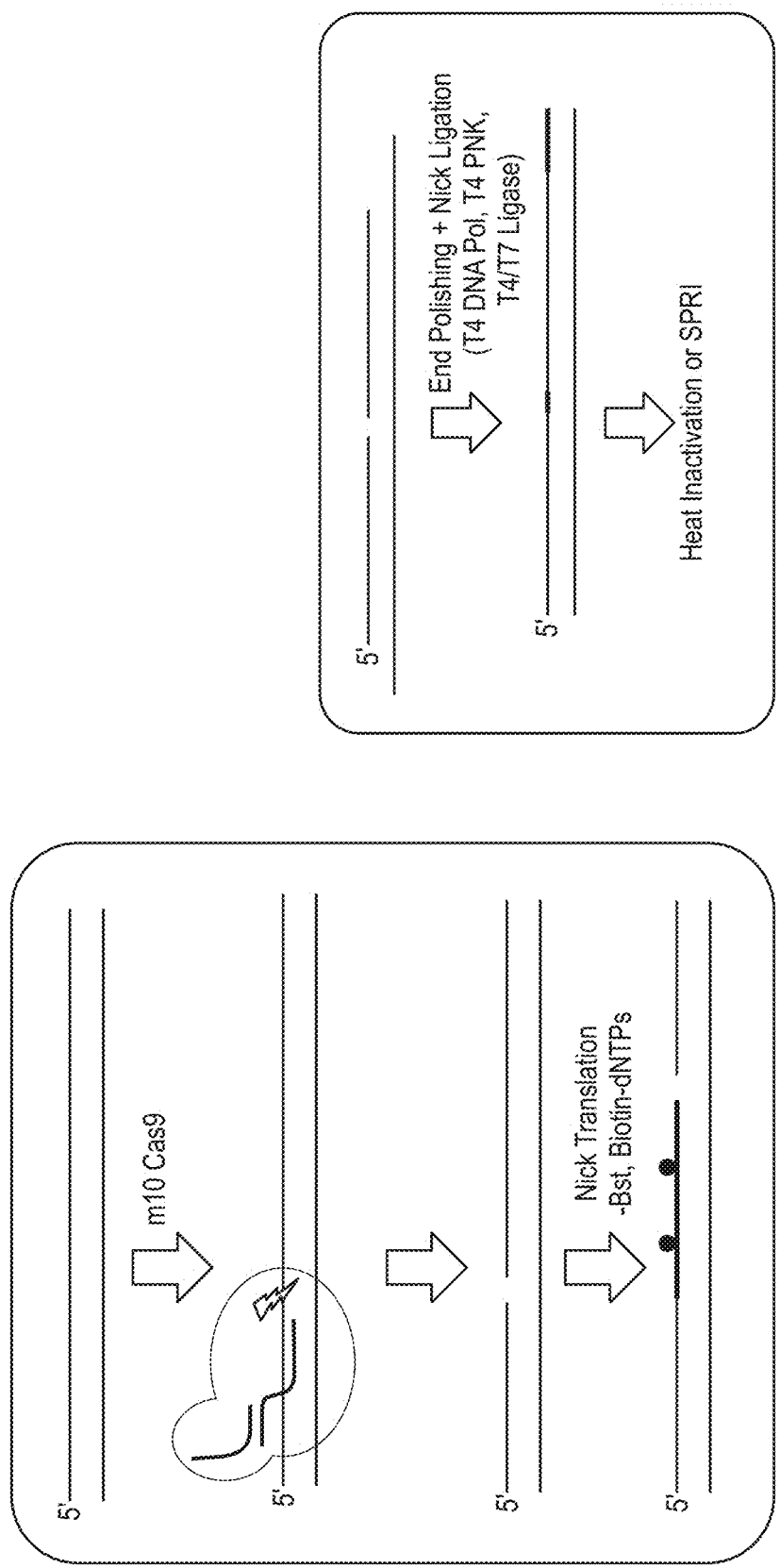
FIGS. 7A-7C illustrate a method for enriching a target double-stranded DNA sequence using a Cas9 nickase and nick translation.

As illustrated in FIG. 7A, a CRISPR-Cas system contains a Cas9 nickase in which one of the two nuclease domains is inactivated, e.g., D10A and H840 Cas9 mutants. The CRISPR-Cas system also contains a guide RNA, e.g., crRNA and crRNA-tracrRNA chimera, that contains a sequence substantially complementary to the target DNA sequence. The enzyme system binds to the target double-stranded DNA and creates a single-stranded nick. This nick serves as the starting point for nick translation using a nick translation polymerase, such as Bst. During the nick translation, biotinylated dNTPs are used to generate biotin labeled DNA fragment, so that the target DNA can be separated by adding magnetic streptavidin beads, as illustrated in the left panel of FIG. 7A. In some embodiments, to prevent non-specific nick translation, nicks present in the DNA prior to Cas9 cleavage can be removed using various methods known in the art, e.g., using DNA ligase, and 3' and 5' overhangs can also be filled in or chewed back with polymerase, as illustrated in the right panel of FIG. 7A. In some embodiments, targeted DNA can first be treated with a cocktail of DNA polymerase, ligases and kinase to remove any preexisting nicks and recessive ends. Repaired DNA is incubated with Cas9 nickase complexes introducing single stranded nicks at targeted regions of the genome, which are used in nick translation reaction with biotinylated nucleotide. Biotinylated targeted regions of the genome are enriched with streptavidin coated beads in a pull down assay.

In some embodiments, the method of present disclosure further includes providing a second nuclease system having a second crRNA or a derivative thereof, and a second Cas protein or a variant thereof, wherein the second crRNA or the derivative thereof contains a second target-specific nucleotide region complementary to a second region of the target nucleic acid, and wherein the second Cas protein contains one inactivated nuclease domain, and contacting the double-stranded nucleic acid containing the target nucleic acid with the second nuclease system to generate a second single-stranded nick at the second region of the target nucleic acid, wherein the first region of the target nucleic acid is different from the second region of the target nucleic acid.

In some embodiments, the first single-stranded nick and the second single-stranded nick are on the same strand of the target nucleic acid. In some embodiments, the first region of the target nucleic acid and the second region of the target nucleic acid are on the same strand of the target nucleic acid, and the first Cas9 protein and the second Cas9 protein both contain a mutation in the domain that cleaves a target nucleic acid strand that is complementary to their respective crRNAs, so that the first single-stranded nick and the second single-stranded nick are on the same strand of the target nucleic acid. In some embodiments, the first Cas protein is a first Cas9 protein containing one inactivated nuclease domain having a first mutation in the domain that cleaves a target nucleic acid strand that is complementary to the first crRNA, and the second Cas protein is a second Cas9 protein containing one inactivated nuclease domain containing a second mutation in the domain that cleaves a target nucleic acid strand that is complementary to the second crRNA. In some embodiments, the first mutation and the second mutation are both D10A.

In some embodiments, the first region of the target nucleic acid and the second region of the target nucleic acid are on the same strand of the target nucleic acid, and the first Cas9 protein and the second Cas9 protein both contain a mutation in the domain that cleaves a target nucleic acid strand that is non-complementary to their respective crRNAs, so that the first single-stranded nick and the second single-stranded nick are on the same strand of the target nucleic acid. In some embodiments, the first Cas protein is a first Cas9 protein containing one inactivated nuclease domain having a first mutation in the domain that cleaves a target nucleic acid strand that is non-complementary to the first crRNA, and the second Cas protein is a second Cas9 protein containing one inactivated nuclease domain containing a second mutation in the domain that cleaves a target nucleic acid strand that is non-complementary to the second crRNA. In some embodiments, the first mutation and the second mutation are both H840A.

In some embodiments, the first region of the target nucleic acid and the second region of the target nucleic acid are on different strands of the target nucleic acid, and the two Cas9 proteins retain different nuclease domains, so that the first single-stranded nick and the second single-stranded nick are on the same strand of the target nucleic acid. In some embodiments, the first Cas protein is a first Cas9 protein containing one inactivated nuclease domain with a first mutation in the domain that cleaves a target nucleic acid strand that is complementary to the first crRNA, and the second Cas protein is a second Cas9 protein containing one inactivated nuclease domain with a second mutation in the domain that cleaves a target nucleic acid strand that is non-complementary to the second crRNA. In some embodiments, the first mutation is D10A, and said second mutation is H840A.

In some embodiments, the space between the first single-stranded nick and the second single-stranded nick is from 20 base pairs (bp) to 10 kp. In some embodiments, the space between the first single-stranded nick and the second single-stranded nick is from 20 base pairs (bp) to 5 kp. In some embodiments, the space between the first single-stranded nick and the second single-stranded nick is from 20 base pairs (bp) to 1000 bp. In some embodiments, the space between the first single-stranded nick and the second single-stranded nick is from 20 base pairs (bp) to 500 bp. In some embodiments, the space between the first single-stranded nick and the second single-stranded nick is about 20 bp, 30 bp, 40 bp, 50 bp, 60 bp, 70 bp, 80 bp, 90 bp, 100 bp, 200 bp, 300 bp, 400 bp, or 500 bp.

In some embodiments, the method of the present disclosure further includes adding a capture probe; and exchanging a single-stranded nucleic acid product between the first single-stranded nick and the second single-stranded nick with the capture probe, wherein the capture probe is able to hybridize to a nucleic acid strand complementary to the single-stranded nucleic acid product. In some embodiments, the sequence of the capture probe is 10% to 100% identical to the sequence of the single-stranded nucleic acid product. In some embodiments, the sequence of the capture probe is about 10%, 20%, 30%, 40%, 50%, 60%, 70%, 80%, or 90% identical to the sequence of the single-stranded nucleic acid product. In some embodiments, the capture probe provided herein is a biotinylated probe. In some embodiments, the method of the present disclosure further includes adding magnetic streptavidin beads to enrich the target nucleic acid.

Figure 8A:
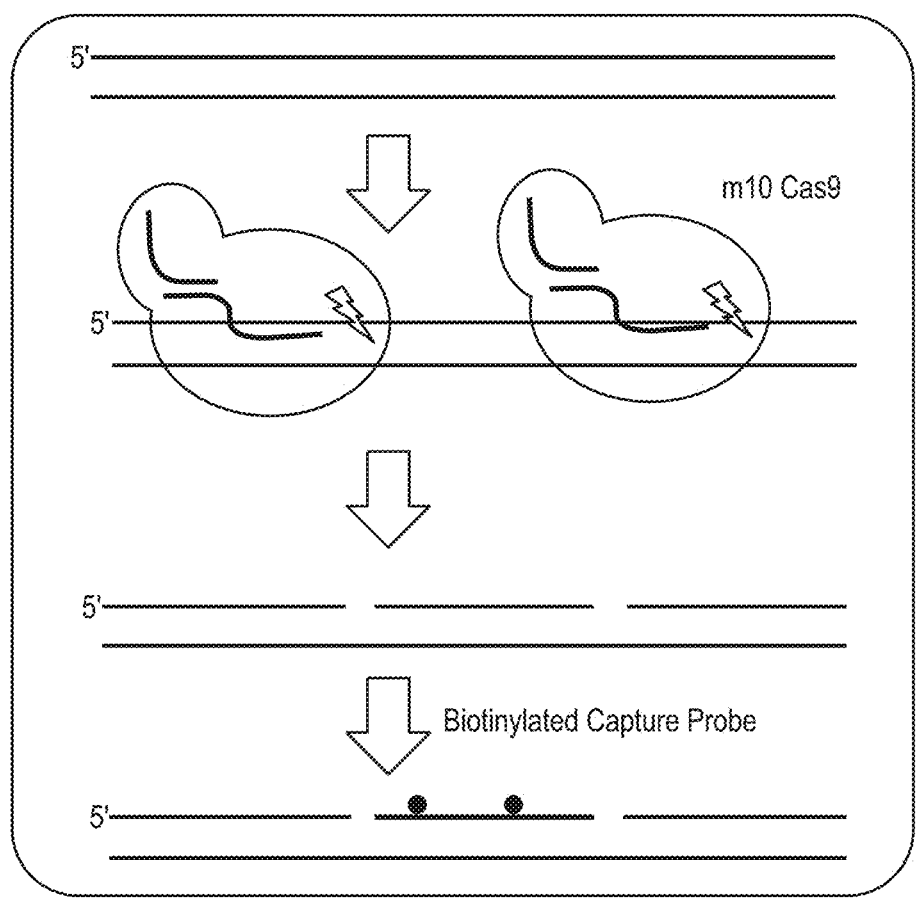

FIG. 8A illustrates one embodiment in which the Cas9 nickases generate two consecutive single-stranded nicks on the same strand of the target DNA. As shown, two enzymes systems are added with each targeting to a different region of the target DNA sequence, and thus two consecutive single-stranded nicks are generated on the same strand. The single-stranded DNA product between the two nicks is then replaced with a capture probe, e.g., a biotinylated capture probe, for an enrichment step.

Figure 9:
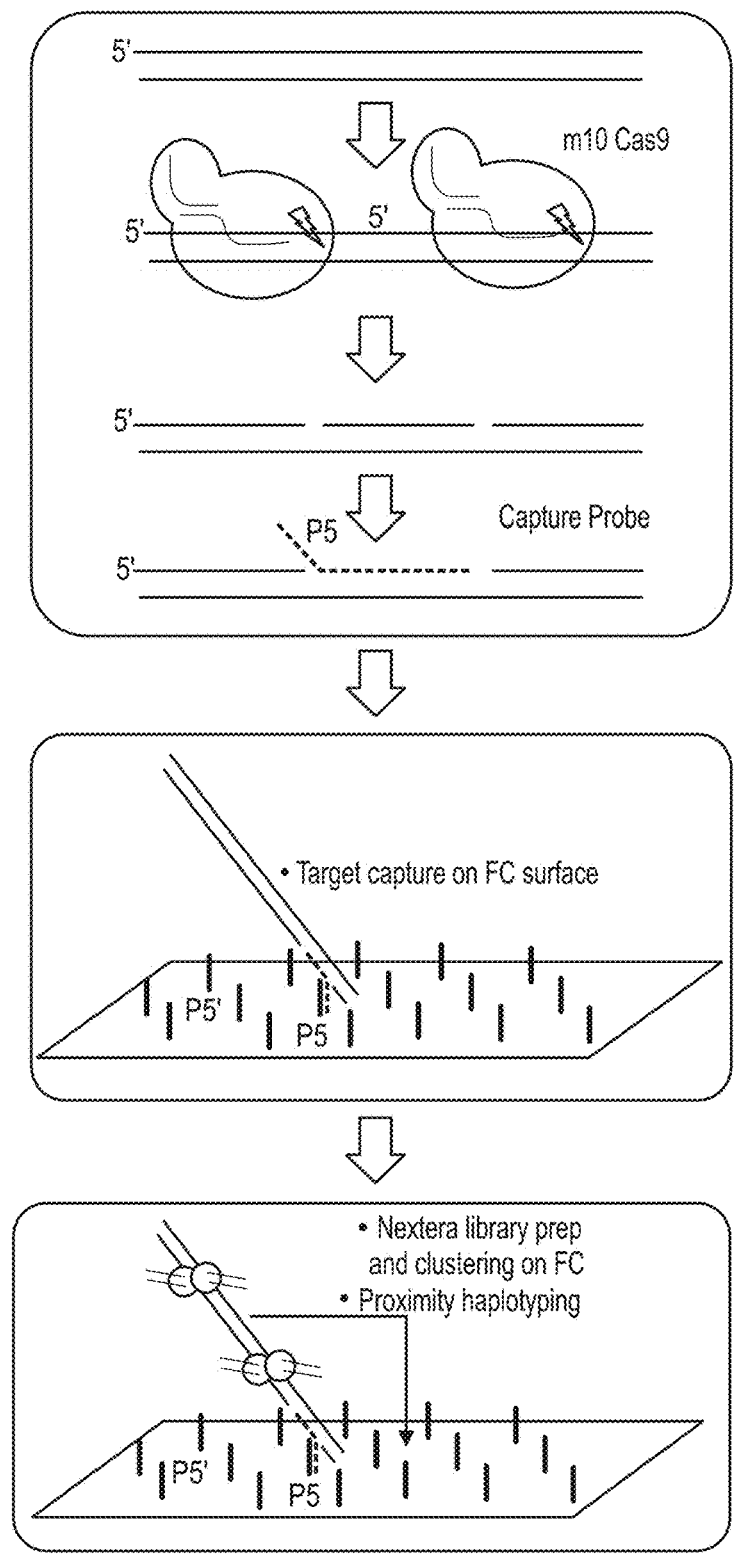
FIG. 9 is a schematic illustrating a method of enriching a target DNA sequence using an overhang capture probe.

In another embodiment, as illustrated in FIG. 9, the capture probe contains an overhang nucleotide sequence, the overhang nucleotide sequence is substantially complementary to an oligo immobilized on a surface. Therefore, the overhang can be used to pull down the target DNA by annealing the overhang to a complementary oligo immobilized on a surface. In one embodiment, the overhang contains or is complementary to the universal Illumina® capture primers P5 (available from Illunima, Inc, San Diego, Calif.). The surface can be an external part or external layer of a solid support. The solid support can be a rigid solid and optionally can be impermeable to liquids or gases. The solid support can also be a semi-rigid solid, for example, being permeable to liquids or gases. The surface can be in contact with another material such as a gas, liquid, gel, second surface of a similar or different solid support, metal, or coat. The surface, or regions thereof, can be substantially flat. The surface can have surface features such as wells, pits, channels, ridges, raised regions, pegs, posts or the like. In some embodiments, a surface or region thereof can be located in a vessel such as a well, tube, channel, cuvette, Petri plate, bottle or the like. A useful vessel is a flow-cell. Exemplary flow-cells are those that are commercially available from Illumina, Inc (San Diego, Calif.). Another useful vessel is a well in a multiwell plate or microtiter plate. In some embodiments, the method provided herein further includes Nextera library preparation and clustering on the surface. In some embodiments, transposition can be performed prior to flow cell capture. Various embodiments have been described in context of a commercially available solid phase platform, e.g., available from Illumina Inc. (San Diego, Calif.), and those skilled in the art will understand that any of the various embodiments can be performed with various other solid phase configurations well known in the art. Such configurations essentially include solid phase and capture probe.

Figure 10:
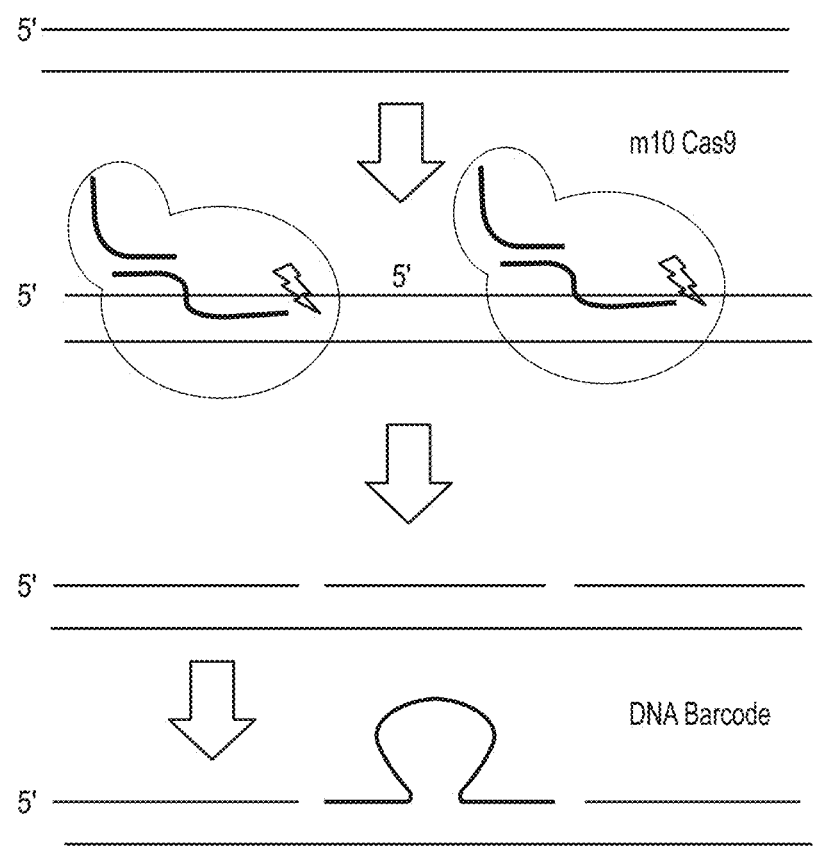
FIG. 10 is a schematic illustrating a method of incorporating a DNA landmark (DNA barcode) into a double-stranded DNA.

In other embodiments, the methods provided herein can be used to introduce specific gaps in repeat regions. In one embodiment, the capture probe has a "hairpin" or is a mismatched probes with 5' and 3' regions complementary to the target DNA as illustrated in FIG. 10. As a result, each repeat unit is replaced with a unique marker (or barcode) allowing the introduction of landmarks. The landmarks can be used for assembly of repeat regions or counting the exact number of repeats.

Certain polymerases e.g., Phi29, can initiate a nick translation from a gap. Thus, in yet other embodiments, the space between the first single-stranded nick and the second single-stranded nick on the same strand of the target nucleic acid is 1 bp to 20 bp. In some embodiments, the method provided herein can further comprise performing a nick translation. In some embodiments, the nick translation is performed by using a nick translation polymerase Phi29.

In some embodiments, the first single-stranded nick and the second single-stranded nick are on opposite strands of the target DNA sequence, thereby generating a first double-stranded DNA break end.

In some embodiments, the first region of the target nucleic acid and the second region of the target nucleic acid are on the same strand of the target nucleic acid; the first Cas protein is a first Cas9 protein with one inactivated nuclease domain having a first mutation in the domain that cleaves a target nucleic acid strand that is complementary to the first crRNA, and the second Cas protein is a second Cas9 protein with one inactivated nuclease domain having a second mutation in the domain that cleaves a target nucleic acid strand that is non-complementary to the second crRNA. In some embodiments, the first mutation is D10A, and the second mutation is H840A.

In some embodiments, the first region of the target nucleic acid and the second region of the target nucleic acid are on opposite strands of the target nucleic acid; first Cas protein is a first Cas9 protein containing one inactivated nuclease domain having a first mutation in the domain that cleaves a target nucleic acid strand that is complementary to the first crRNA, and the second Cas protein is a second Cas9 protein containing one inactivated nuclease domain containing a second mutation in the domain that cleaves a target nucleic acid strand that is complementary to the second crRNA. In some embodiments, both the first mutation and the second mutation are D10A.

In some embodiments, the first region of the target nucleic acid and the second region of the target nucleic acid are on opposite strands of the target nucleic acid; the first Cas protein is a first Cas9 protein containing one inactivated nuclease domain having a first mutation in the domain that cleaves a target nucleic acid strand that is non-complementary to the first crRNA, and the second Cas protein is a second Cas9 protein containing one inactivated nuclease domain containing a second mutation in the domain that cleaves a target nucleic acid strand that is non-complementary to the second crRNA. In some embodiments, the first mutation and the second mutation are both H840A.

In some embodiments, nicks are made at relatively close nucleic acid positions, and a blunt ended break can be produced. In some embodiments, nicks are made at relatively far away from each other, and a sticky ended break with 5' or 3' overhangs can be produced. In some embodiments, the method of the present disclosure further includes ligating an adaptor to the double-stranded nucleic acid break end. In some embodiments, the adaptor of the present disclosure is biotinylated. In some embodiments, the method of the present disclosure includes adding magnetic streptavidin beads to enrich the target nucleic acid.

In some embodiments, the method provided herein further includes providing a third nuclease system having a third crRNA or a derivative thereof, and a third Cas protein or a variant thereof, wherein the third crRNA or the derivative thereof contains a third target-specific nucleotide region substantially complementary to a third region of the target nucleic acid, and wherein the third Cas protein contains one inactivated nuclease domain; providing a fourth nuclease system having a fourth crRNA or a derivative thereof, and a fourth Cas protein or a variant thereof, wherein the fourth crRNA or the derivative thereof contains a fourth target-specific nucleotide region substantially complementary to a fourth region of the target nucleic acid, and wherein the fourth Cas protein contains one inactivated nuclease domain; and contacting the double-stranded nucleic acid containing the target nucleic acid with the third and fourth nuclease systems to generate a third single-stranded nick at the third region of the target nucleic acid and a fourth single-stranded nick at the fourth region of the target nucleic acid, wherein in the third single-stranded nick and the fourth single-stranded nick are on opposite strands of the target nucleic acid, thereby generating a second double-stranded nucleic acid break end, the second double-stranded nucleic acid break end being different from the first double-stranded nucleic acid break end.

In some embodiments, the nucleic acid fragment between the first and second double-stranded nucleic acid break ends can contain from 10 to multiple thousands of nucleotides. In some embodiments, capture probes, such as single-stranded oligos, DNA dumbbells, and double-stranded DNA adapters can be added to label the nucleic acid fragment. In some embodiments, the method provided herein further includes ligating an adapter to the second double-stranded nucleic acid break end.

Figure 11A:
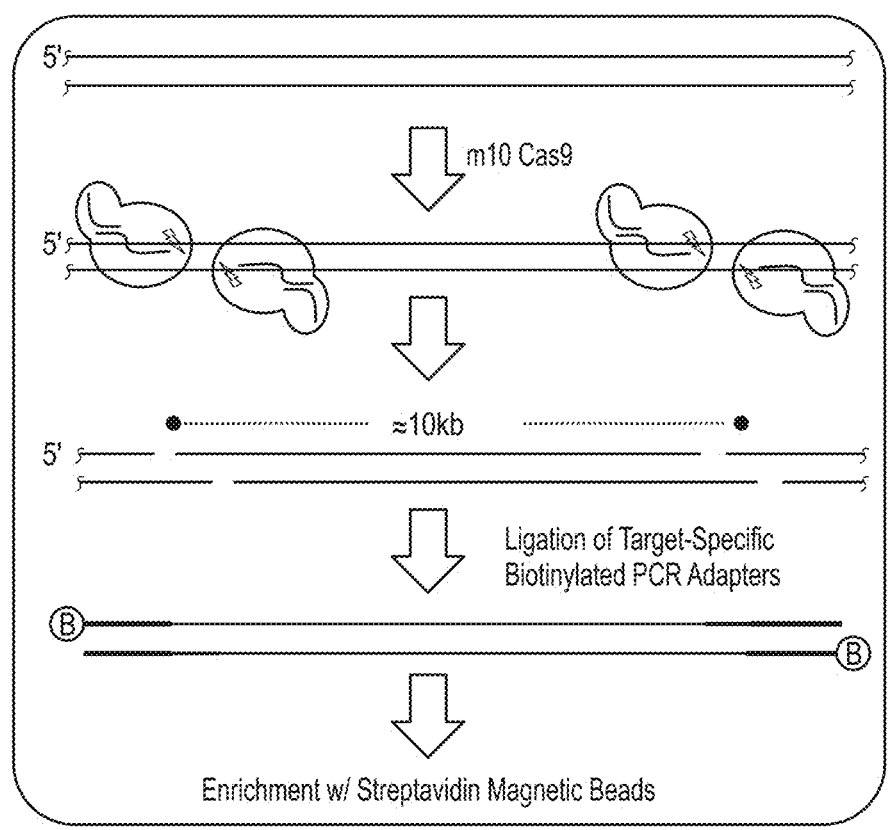
FIG. 11A illustrates a method for generating two consecutive single-stranded nicks on opposite strands of a target DNA using Cas9 nickases for enriching the target DNA.

As illustrated in FIG. 11A, two pairs of CRISPR-Cas systems are provided. Each pair of enzymes contains two Cas9 nickases, and the two Cas9 nickases can generate single-stranded DNA nicks on opposite strands of DNA. As such, each pair of enzymes generates a double-stranded DNA break end, and two double-stranded DNA break ends are generated surrounding or at the two ends of the target DNA sequence. In one embodiment, the DNA fragment between the two double-stranded DNA break ends is about 10 kb. In some embodiments, the DNA fragment between the two double-stranded DNA break ends is about 1 kb, 2 kb, 3 kb, 4 kb, 5 kb, 6 kb, 7 kb, 8 kb, or 9 kb. The DNA fragment can be further ligated to target-specific biotinylated PCR adapters through which the target DNA can be enriched.

Figure 11B:
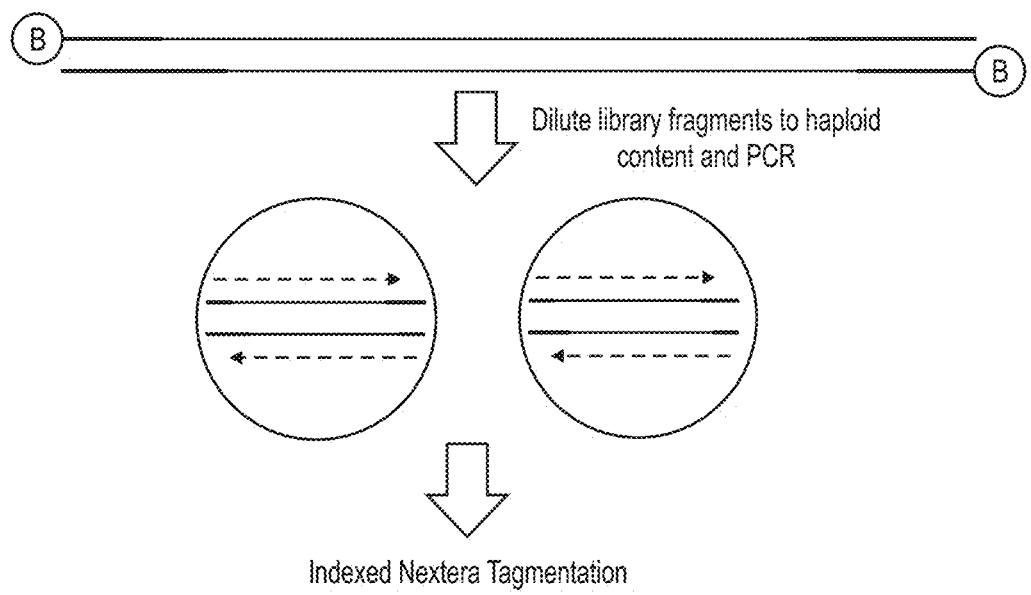
FIG. 11B illustrates a method of diluting fragments to haploid content prior to tagmentation.

The enriched double-stranded nucleic acid can be further subject to sequencing. In one embodiment, the enriched DNA is tagmented to smaller fragments and introduced to sequencing adapters. As illustrated in FIG. 11B, in some embodiments, the method provided herein further includes dilution prior to tagmentation. In one embodiment, the enriched DNA is diluted to haploid content prior to PCR and/or tagmentation.

In some embodiments, Nextera library preparation (available from Illumina, Inc, San Diego, Calif.) is performed to fragment input DNA and introduce sequencing primers, and then the fragmented DNA is contacted with the CRISPR-Cas system provided herein to form a complex. The complex is pulled down and the target DNA can be released from the complex, e.g., using EDTA, heat, SDS, and RNase. The sequencing can then be performed.

In another aspect, the present disclosure provides a method of enriching double-stranded DNA using multiple wild-type Cas9 containing two nuclease domains. In some embodiments, provided herein is a method for enriching a target nucleic acid including: providing a population of Cas9 proteins programmed with a set of crRNAs, wherein the set of crRNAs contains crRNAs complementary to a series of different regions of the target nucleic acid; contacting the target nucleic acid with the population of Cas9 proteins programmed with the set of crRNAs to generate a series of nucleic acid fragments, and ligating adaptors to at least one of nucleic acid fragments, wherein the Cas9 protein retains two nuclease domains.

In some embodiments, the set of crRNAs contains crRNAs complementary to two different regions of the target nucleic acid. The method provided herein can be useful for enriching a long DNA fragment. In some embodiments, the space between the two different region is longer than 10 kb.

In some embodiments, the target nucleic acid is a double-stranded DNA. In some embodiments, the target nucleic acid is a genomic DNA, a chromosomal DNA, a genome, or a partial genome.

Figure 12A:
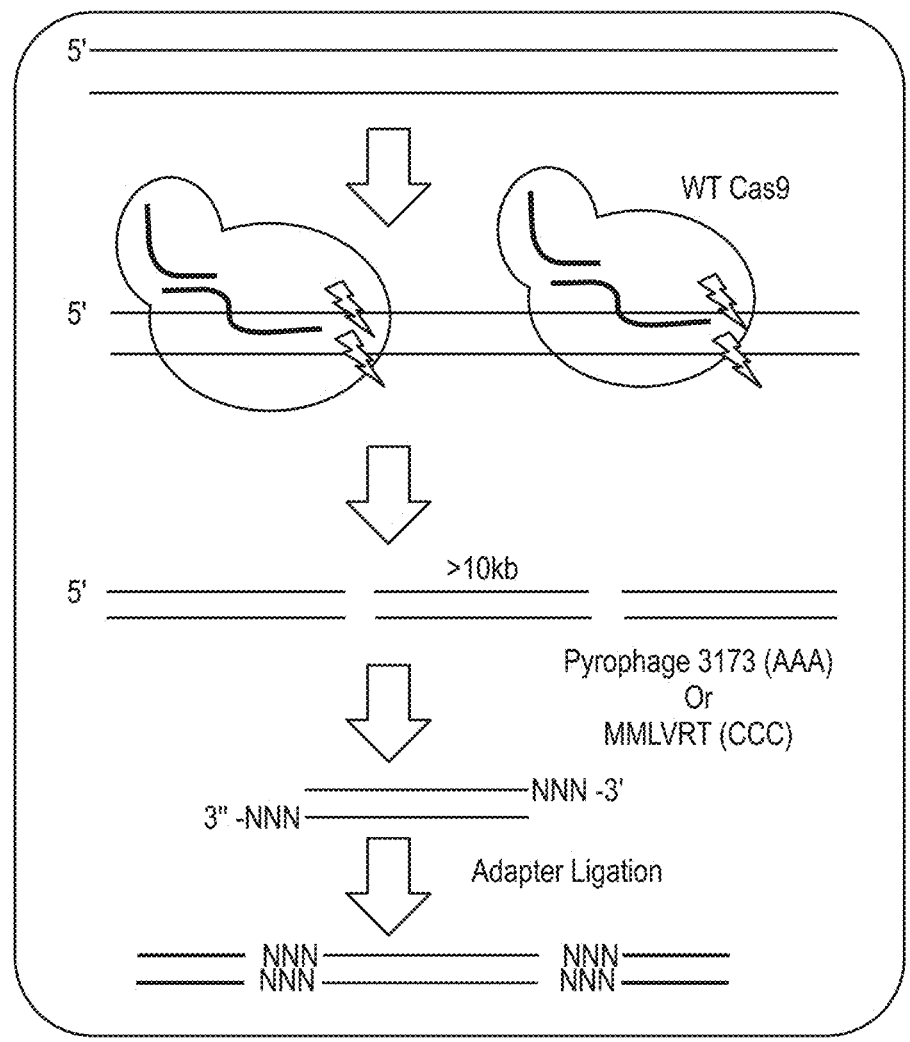
FIG. 12A illustrates a method of enrichment of double-stranded DNA using multiple WT Cas9s.

As illustrated in FIG. 12A, two Cas9 proteins each containing two nuclease domains are used to treat a double-stranded nucleic acid. Each Cas9 is programmed with a crRNA targeting to a different region on the double-stranded DNA, and thus the reaction generates a double-stranded DNA fragment between the two cutting sites. The DNA fragment can be ligated to adaptors and be prepared for other process and/or analysis, e.g., pull down and sequencing.

In another aspect, the present disclosure provides a method of Cas9 mediated nucleic acid fragmentation and targeted sequencing. The present disclosure provides a method for fragmenting DNA in a sequence specific manner in user defined regions, and generating nucleic acid fragments for subsequent sequencing, e.g., DNA fragments amendable for incorporation into Illumina's sequencing libraries. In some embodiments, the method for sequencing a target nucleic acid provided herein includes providing a population of Cas9 proteins programmed with a set of crRNAs, wherein the set of crRNAs contains crRNAs complementary to a series of different regions across the target nucleic acid; contacting the target nucleic acid with the population of Cas9 proteins programmed with the set of crRNAs to generate a series of nucleic acid fragments, and sequencing the series of nucleic acid fragments.

In some embodiments, targeted fragmentation of nucleic acid can be achieved by preparing a population of Cas9 proteins that are programmed with crRNAs targeting regions tiled across the target nucleic acid. In some embodiments, the Cas9 proteins provided herein retain two nuclease domains, they can generate double-stranded nucleic acid breaks and thus a series of nucleic acid fragments. These nucleic acid fragments can be further subjected to nucleic acid sequencing workflows.

The same nucleic acid sample can be treated separately with multiple populations of Cas9 proteins programmed with different sets of crRNAs targeting regions tiled across the target nucleic acid. The nucleic acid fragments generated by each population overlap with nucleic acid fragments generated by another population. More reliable and comprehensive sequencing data can be achieved by sequencing nucleic acid fragments with overlapping sequences. In some embodiments, the method for sequencing a target nucleic acid provided herein includes providing a plurality of populations of Cas9 proteins, each population of Cas9 proteins being programmed with a different set of crRNAs, wherein each set of crRNAs contains crRNAs complementary to a different series of regions across the target nucleic acid; contacting the target nucleic acid with each of the plurality of populations of Cas9 proteins in a separate reaction to generate a different series of nucleic acid fragments, and sequencing the nucleic acid fragments.

Figure 12B:
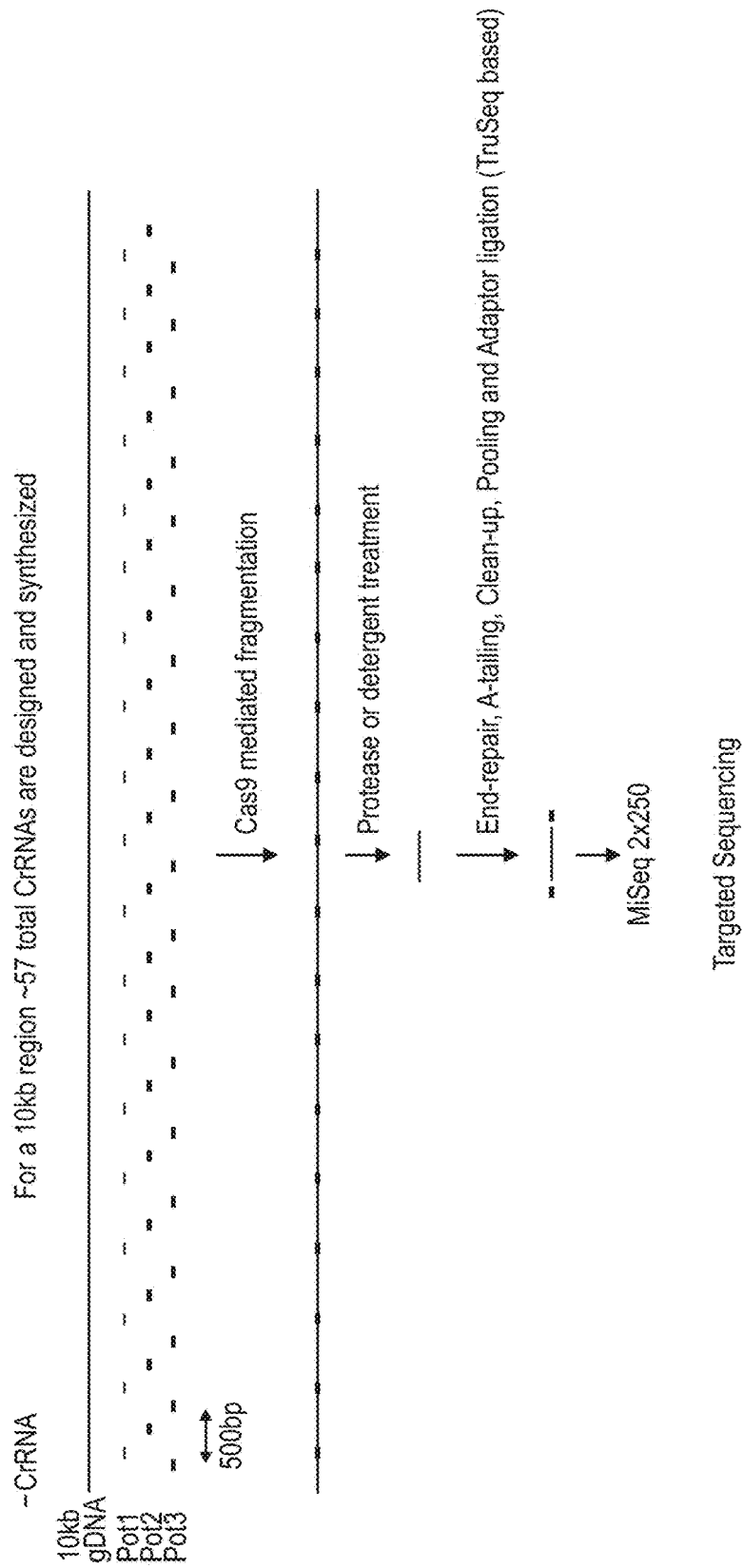
FIGS. 12B-12C illustrate methods for DNA sequencing using CRISPR-Cas systems.

In some embodiments, the plurality of populations of Cas9 proteins includes three populations of Cas9 proteins, and wherein the nucleic acid fragments generated by each of the three populations of Cas9 proteins contain overlapping sequences with the nucleic acid fragments generated by at least another of the three populations of Cas9 proteins. As illustrated in FIG. 12B, a 10 kb target DNA is treated with the Cas9 proteins programmed with three sets of crRNAs targeting regions with about 500 bp intervals across the target DNA sequence. Each set of crRNAs contains about 57 crRNAs. Cas9 proteins remain non-covalently associated with the ends of cleaved DNAs, cleaved target DNA can be released by treatment of the sample with protease or detergent. Cleavage products are then pooled and converted to sequencing libraries, e.g., using Illumina's TruSeq Nano workflow. The cleavage can be carried out using a different set of crRNAs in a separate reaction. For instance, as illustrated in FIG. 12B, cleavage is carried out in 3 tubes (Pot 1, Pot 2, and Pot 3) with three libraries of Cas9 complexes reconstituted with cRNAs that generate overlapping fragments about 500 bp in size. Such overlapping fragments can improve the sequencing accuracy.

In some embodiments, the present disclosure provides a method for targeted haplotype sequencing (phased sequencing). In some embodiments, the method provided herein further includes diluting a DNA sample containing the target DNA to haploid content. Phase or haplotype information, which refers to the unique content of the two homologous chromosomes in diploid organisms, provides a useful tool to better understand relationships between human DNA sequence and phenotype, including diseases. The present disclosure provides a method for haplotype sequencing using CRISPR-Cas systems. A haplotype sequencing workflow can take advantage of the ability of Cas9 proteins to hold onto ends of cleaved DNA. Since Cas9 proteins remain association with the ends of cleaved DNAs, this creates a haplotype block of DNA proportional in size to the number and distance between Cas9 target regions in a target sequence. In some embodiments, following cleave, reactions can be diluted in microtiter wells to subhaplotype levels, and then can be treated with protease to release joined fragments and converted into a sequencing library, e.g., using TruSeq Nano library preparation method available from Illumina, Inc. (San Diego, Calif.).

Figure 12C:
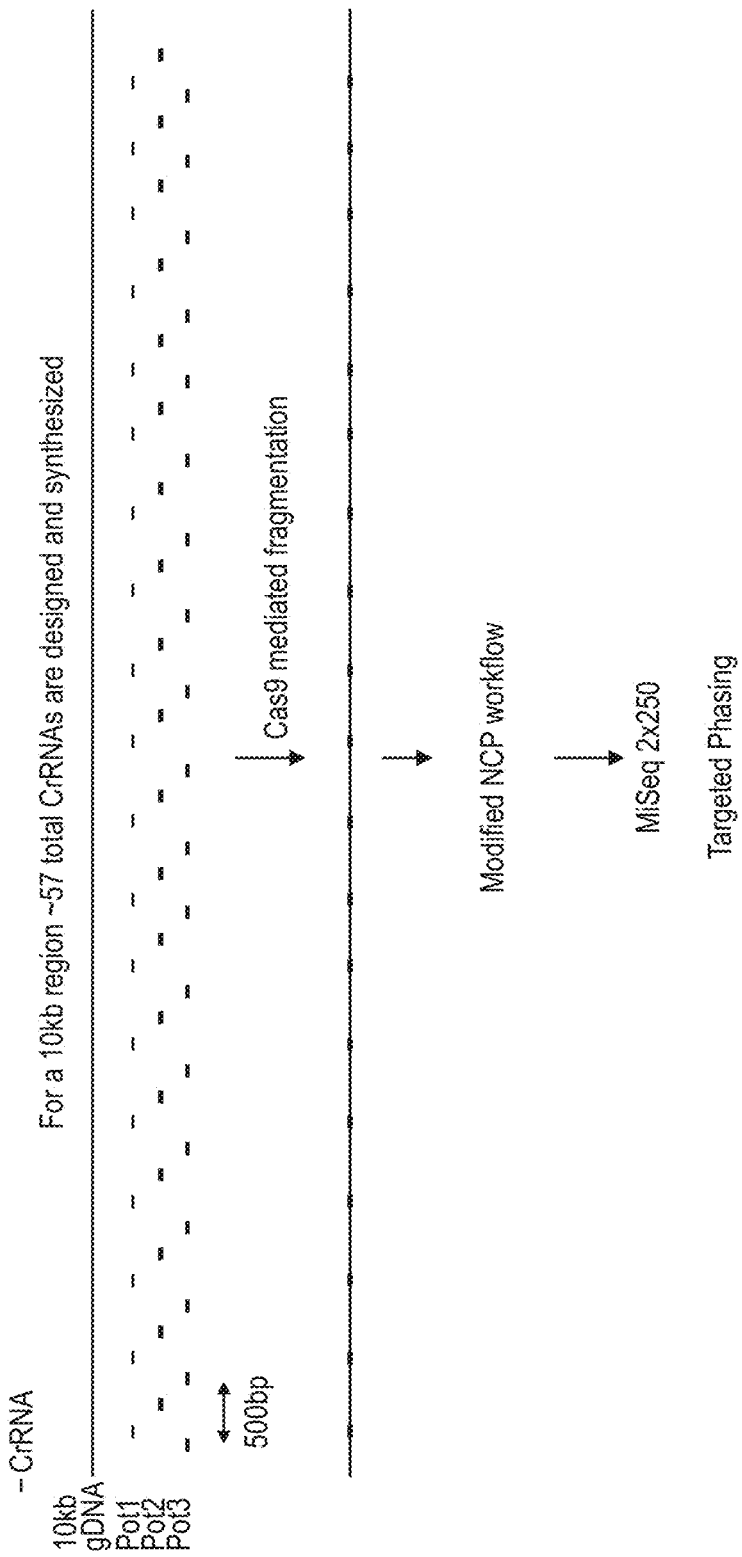

As illustrated in FIG. 12C, a 10 kb target DNA is treated with the Cas9 proteins programmed with a set of crRNAs targeting regions with about 500 bp intervals across the target DNA sequence. Following cleavage, reactions are diluted in microtiter wells to sub-haplotype levels. Then cleaved target DNA can be released by treatment of the sample with protease or detergent. Cleavage products are then pooled and converted to sequencing libraries, e.g., using Illumina's TruSeq Nano workflow. The cleavage can be carried out using multiple reactions with different sets of crRNAs. For instance, as illustrated in FIG. 12C, cleavage is carried out in 3 tubes (Pot 1, Pot 2, and Pot 3) with three libraries of Cas9 complexes reconstituted with cRNAs that generate overlapping fragments about 500 bp in size. Such overlapping fragments can improve haplotype sequencing accuracy.

In some embodiments, the target nucleic acid provided herein is a double-stranded DNA. In some embodiments, the target nucleic acid provided herein is a genomic DNA, a chromosomal DNA, a genome, or a partial genome.

In some embodiments, the nucleic acid fragments can be amplified, e.g., using limited-cycle polymerase chain reaction (PCR), to introduce other end sequences or adaptors, e.g., index, universal primers and other sequences required for cluster formation and sequencing.

In some embodiments, the sequencing the nucleic acid fragments includes use of one or more of sequencing by synthesis, bridge PCR, chain termination sequencing, sequencing by hybridization, nanopore sequencing, and sequencing by ligation.

In some embodiments, the sequencing methodology used in the method provided herein is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., *Analytical Biochemistry* 242(1), 84-9 (1996); Ronaghi, *Genome Res.* 11(1), 3-11 (2001); Ronaghi et al. *Science* 281(5375), 363 (1998); U.S. Pat. Nos. 6,210,891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883 and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zeromode waveguides (ZMWs). Techniques and reagents for FRET-based sequencing are described, for example, in Levene et al. *Science* 299, 682-686 (2003); Lundquist et al. *Opt. Lett.* 33, 1026-1028 (2008); Korlach et al. *Proc. Natl. Acad. Sci. USA* 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available from Ion Torrent (Guilford, Conn., a Life Technologies subsidiary) or sequencing methods and systems described in US 2009/0026082 A1; US 2009/0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another useful sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

From the foregoing description, it will be apparent that variations and modifications can be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

The following examples are provided by way of illustration, not limitation.

EXAMPLES

Example 1

Enriching Target DNA Using a CRISPR-Cas System Containing a Wild Type Cas9 Protein This example illustrates a method of enriching a target DNA sequence using a CRISPR-Cas system containing a wild type Cas9 protein which retains nuclease activity for both of the two nuclease domains. The left panel of FIG. 2A illustrates the procedure of the experiment. First, a plasmid with 3550 bp containing a wild type Braf sequence is treated with a restriction enzyme AlwNI which produces a DNA break outside the Braf sequence. Second, a CRISPR-Cas system containing a wild type Cas9 protein and a biotin labeled guide RNA is added. The guide RNA contains a sequence complementary to the wild type Braf sequence, and thus the enzyme system recognizes and binds to a region of Braf sequence to form a complex. The Cas9 nuclease cuts at a region of Braf to produce two DNA fragments—one is 2250 bp and the other is 1300 bp. Third, streptavidin beads, which can bind to biotin, are then added. Finally, after washing the beads and eluting with protease, the Cas9 pull down supernatant and bead elution samples are subject to polyacrylamide gel electrophoresis and the result is visualized by phosphorimaging. The experiment is done with control crRNA, crRNA entirely labeled with biotinylated dUTP (IVT), and crRNA with 2 biotin groups on 3' end (BioSynthesis). The gel electrophoresis result is shown in the right panel of FIG. 2A. As shown, when control crRNA is used, two DNA fragments, one about 2250 bp and one about 1300 bp, are present in the Cas9 pull down supernatant. But these DNA fragments are not in bead elution. In contrast, when IVT biotinylated crRNA or BioSynthesis dual biotin crRNA is used, the amount of the two DNA fragments in the Cas9 pull down supernatant is much reduced if detectable at all. Instead, the two DNA fragments are present in the bead elusion.

The experiment is also done using Bgl 1 restriction enzyme. Specifically, the procedure of the experiment is illustrated in the left panel of FIG. 2B. First, a plasmid with 3550 bp containing a wild type Braf sequence is treated with a restriction enzyme Bgl 1 which produces two DNA breaks outside the Braf sequence. As a result, the plasmid is divided to two DNA fragments: one is 2464 bp containing the Braf sequence and the other is 1118 bp. Second, a CRISPR-Cas system containing a wild type Cas9 protein and a biotin labeled guide RNA is added. The guide RNA contains a sequence complementary to the wild type Braf sequence, and thus the enzyme system recognizes and binds to a region of Braf sequence within the 2464 bp fragment to form a complex. The Cas9 nuclease cuts at a region of Braf to produce two DNA fragments—one is 1854 bp and the other is 610 bp. Third, streptavidin beads, which can bind to biotin, are then added. Finally, after washing the beads and eluting with protease, the Cas9 pull down supernatant and bead elution samples are subject to polyacrylamide gel electrophoresis and the result is visualized by phosphorimaging. The result is shown in the right panel of FIG. 2B. As shown, when crRNA is not biotinylated, the supernatant contains three DNA fragments with 1854 bp, 1118 bp, and 610 bp; but these three DNA fragments are absent in the bead elution. In contrast, when biotinylated crRNA is used, the bead elution contains two DNA fragments with 1854 bp and 610 bp. It is noted that when streptavidin beads are washed with 250 mM NaCl, the bead elution contains detectable 1118 bp DNA fragment indicating non-specific binding. Improved binding specificity is shown when high salt wash (500 mM NaCl) is used. As shown, when the beads are washing with 500 mM NaCl, the amount of 1118 bp fragment is significantly reduced in bead elution.

The results of these experiments show that the wild type Cas9 protein remains at the DNA ends after the cleavage and this association is sufficient for pulling down the nuclease-DNA complex for enrichment.

Example 2

Figure 2D:
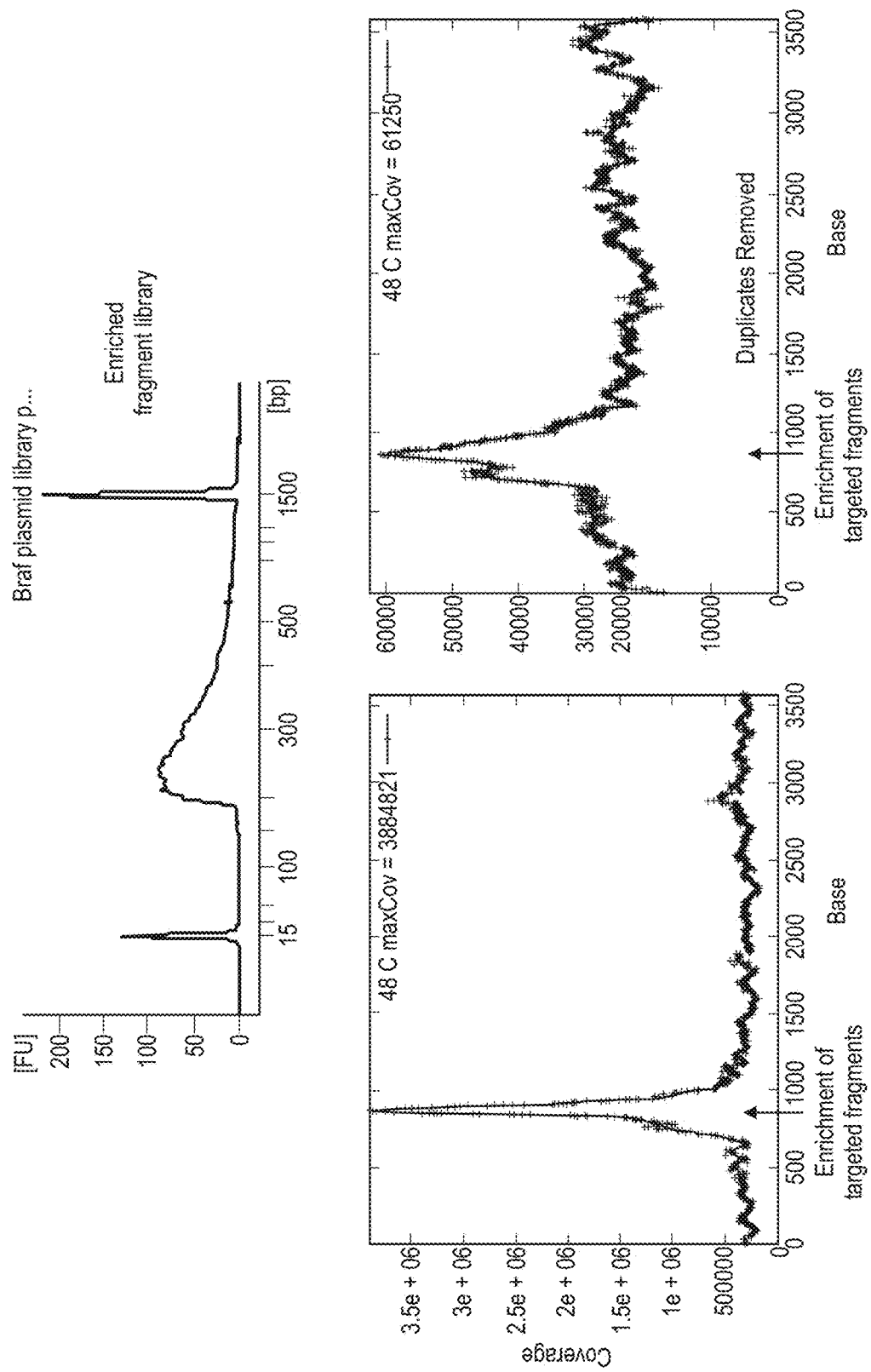

Cas9 Nickase Mediated Enrichment of Fragments from a Low Complexity Nextera Plasmid Library This example illustrates a method for enriching DNA fragments using a CRISPR-Cas system containing a Cas9 nickase. As illustrated in FIG. 2C, plasmids containing a Braf target site were first subject to Tn5 mediated tagmentation to result in a population of DNA fragments. Then CRISPR-Cas9 system containing a Cas9 nickase and a biotin labeled crRNA targeting to Braf sequence was then added to the fragments. The CRISPR-Cas9 system specifically bound to the DNA fragments containing Braf sequence. By pulling down biotin and its associated components using Streptavidin beads, the DNA fragments containing Braf sequence were enriched. After eluted from the proteins, the enriched DNA fragments were further subject to DNA amplification and sequencing. The results of the sequencing are shown in FIG. 2D. As shown, target DNA fragments containing a Braf sequence are successfully enriched.

Example 3

Tagmenting Target DNA Enriched by CRISPR-Cas Systems

The target plasmid contains part of Braf sequence spanning the V600 codon. A biotinylated crRNA is designed to target 20 bp spanning the V600 codon. 50 ng of the target plasmid DNA was cut with Cas9 complex (biotinylated), and bglI restriction enzyme in 1×NEB buffer 3.1 in a 20 ul reaction for 15 minutes at 37° C. The reaction temperature and the bead binding temperature can be raised up to 48° C. to reduce background (nonspecific) binding of Cas9 to non-target DNA. Up to 500 mM NaCl can also be used in binding reactions and washing to reduce the background binding. 20 ul Dynabeads® M-280 Streptavidin beads where added to the reaction and incubated for 30 minutes. Beads were resuspended in the reaction every 10 minutes by brief vortexing. Reaction tubes were then transferred onto a magnet and supernatant was discarded. Beads were washed in 20 ul 1×NEB buffer 3.1 with 400 mM additional NaCl. DNA was released from the beads at 55° C. in 1×NEB buffer 3.1 and 50 ng/ul protease for 15 minutes. Reaction tubes were then transferred onto a magnet and supernatant was transferred to a new tube and cleaned up using the Zymo DNA clean and concentrator kit from Zymo Research. The released DNA was then subject to tagmentation and was converted into Nextera libraries (available from Illumina, Inc, San Diego, Calif.). The libraries were sequenced on a MiSeq and the plasmid coverage plots where generated. As shown in FIG. 4F, reads show enrichment of 610 bp and 1845 bp targeted DNA fragments.

Example 4

Purification of Cas9 Proteins and Testing for Activity and Specificity of Cas9 Proteins FIG. 9A shows the expressions of Cas9 fusion proteins in BL21 cells. BL21 cells were transformed with expression vectors encoding four MBP_CAS9 fusion variants: wild type and three mutants including single mutants D10A, H840A, and D10A_H840A double mutant. Cell cultures were grown at 37° C. with good aeration, induced with IPTG (0.2 mM) at OD600 of 1, and transferred to 17° C. and grown with good aeration for additional 16 hours. Cells were pelleted down, lysed and cellular proteins before (indicated as 1 in the figure) and after induction (indicated as 2 in the figure) were analyzed by SDS_PAGE. The presence of ~250 KDa band in samples after IPTG induction confirmed the expressions of all four MBP_CAS9 fusion proteins.

Purification of M10A Cas9 nickase is illustrated in Example 2. Cell lysate was generated using 1 L cell culture expressing His tagged Cas9 m10 nickase, and then run by His column for purification. The column was then washed by butter. Finally, proteins were eluated from the column. Samples were taken from cell lysate, His Column prior to washing, follow-through washing buffer, and eluate. Specifically, MBP_Cas9 fusion protein, containing an N-terminal hexahistidin tag (SEQ ID NO: 10), was expressed in BL21 cells (Lane 1), purified with His-column chromatography, and His_MBP tag was removed using TEV digestion (Lane 2). Ion-exchange chromatography was used to separate His_MBP tag (Lane 3) from leftovers of undigested MBP_Cas9 fusion and fully processed Cas9 (Lane 4). The samples were analyzed by gel electrophoresis and the results were shown in FIG. 6B. As shown, M10A Cas9 nickases were detected and enriched in eluate.

Both wildtype Cas9 and Cas9 nickase were analyzed for their activities. Two crRNA and one tracrRNA were generated by in vitro transcription with T7 RNA polymerase, purified and each crRNA (10 uM) was annealed with tracrRNA in equal molar ratio. Each crRNA:tracrRNA duplex (1 uM) was incubated with purified Cas9 wid type or D10A nickase (0.5 uM) at 37° C. for 10 minutes in a Cas9 cleavage buffer (20 mM HEPES pH 7.5, 150 mM KCl, 10 mM MgCl2, 0.5 mM DTT). Formed complexes were incubated with corresponding target DNA amplicon (0.025 uM) for various times. Reaction was stopped by adding EDTA (10 mM) and complexes were purified with ZYMO DNA purification-concentration columns. Purified DNA was separated on 8% TBE-Urea PAAG and visualized with SYBR Gold stain.

Figure 6C:
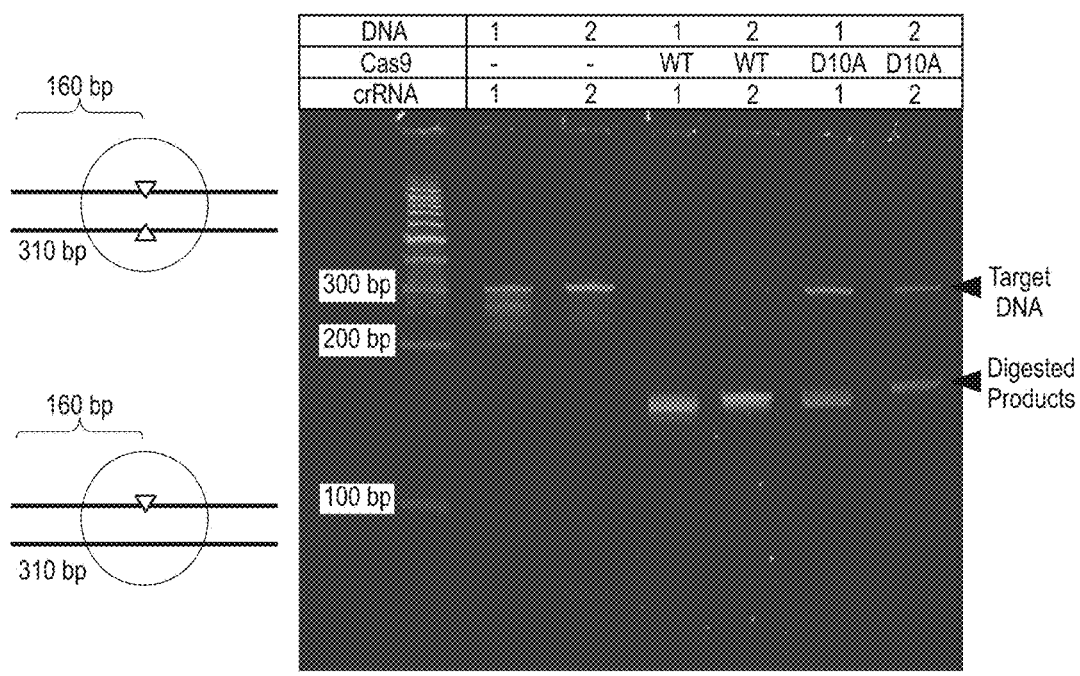
FIGS. 6C-D show the results of activity assays testing the activities of wildtype Cas9 protein and Cas9 nickase.

As shown in panels on the left of FIG. 6C, a 310 bp target amplicon depicted as two black lines representing two DNA strands cut by wild type Cas9 on the top panel, or nicked by D10A nickase on top strand only on the bottom panel. Cas9 WT and D10A nickase recognition site is 160 bases away from the 5' end of target amplicon. Two amplicons (1 and 2) were individually digested with wildtype Cas9 (WT) or D10A nickase Cas9 (D10A) containing complimentary crRNAs (1 and 2). Cleavage products were analyzed on 8% TBE-Urea gel. As shown, 100 ng of amplicon DNA was efficiently cleaved after incubation with 0.5 uM of Cas9 complex for 3 hours at 37° C.

Figure 6D:
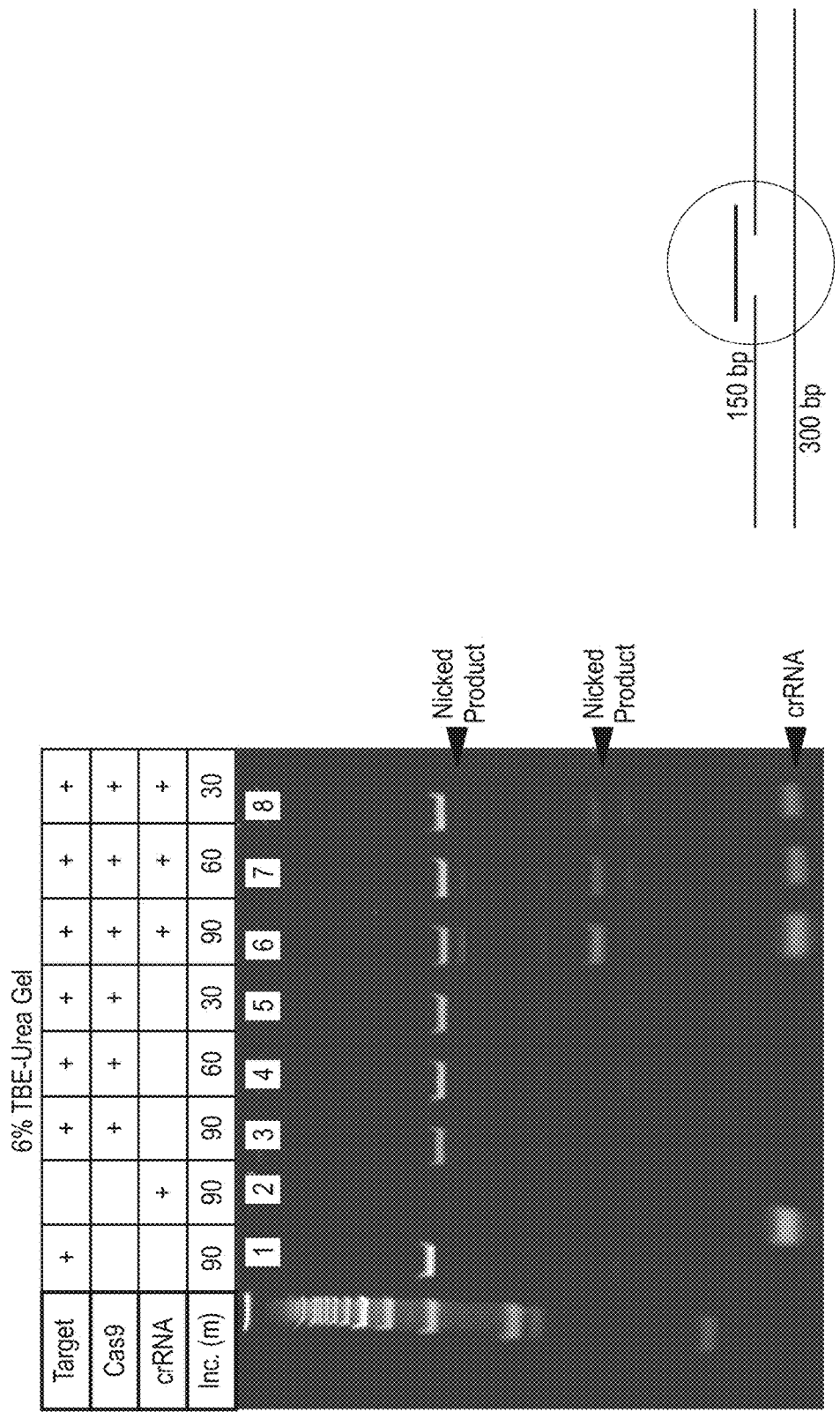

310 bp amplicon (as shown in the right panel of FIG. 6D) was also treated with M10A Cas9 nickase at 37° C. for 30 min, 60 min, or 90 min. The results were shown in the left panel of FIG. 6D. As shown, when both Cas9 nickase and crRNA were present in the complex, nicked products were detected as indicated by arrows. More nicked products were generated as the reaction time increased.

Next, the nicking specificity of the purified M10A Cas9 nickase was tested. Two crRNA and one tracrRNA were generated by in vitro transcription with T7 RNA polymerase, purified and each crRNA (10 uM) was annealed with tracrRNA in equal molar ratio. Each crRNA:tracrRNA duplex (1 uM) was incubated with purified D10A nickase (0.5 uM) at 37° C. for 10 minutes in a Cas9 cleavage buffer (20 mM HEPES pH 7.5, 150 mM KCl, 10 mM MgCl2, 0.5 mM DTT). Formed complexes were incubated with complimentary and non-complimentary target DNA amplicons (0.025 uM) for 72 hours. Reaction was stopped by adding EDTA (50 mM), separated on 6% TBE-Urea PAAG and visualized with SYBR Gold stain.

Figure 6E:
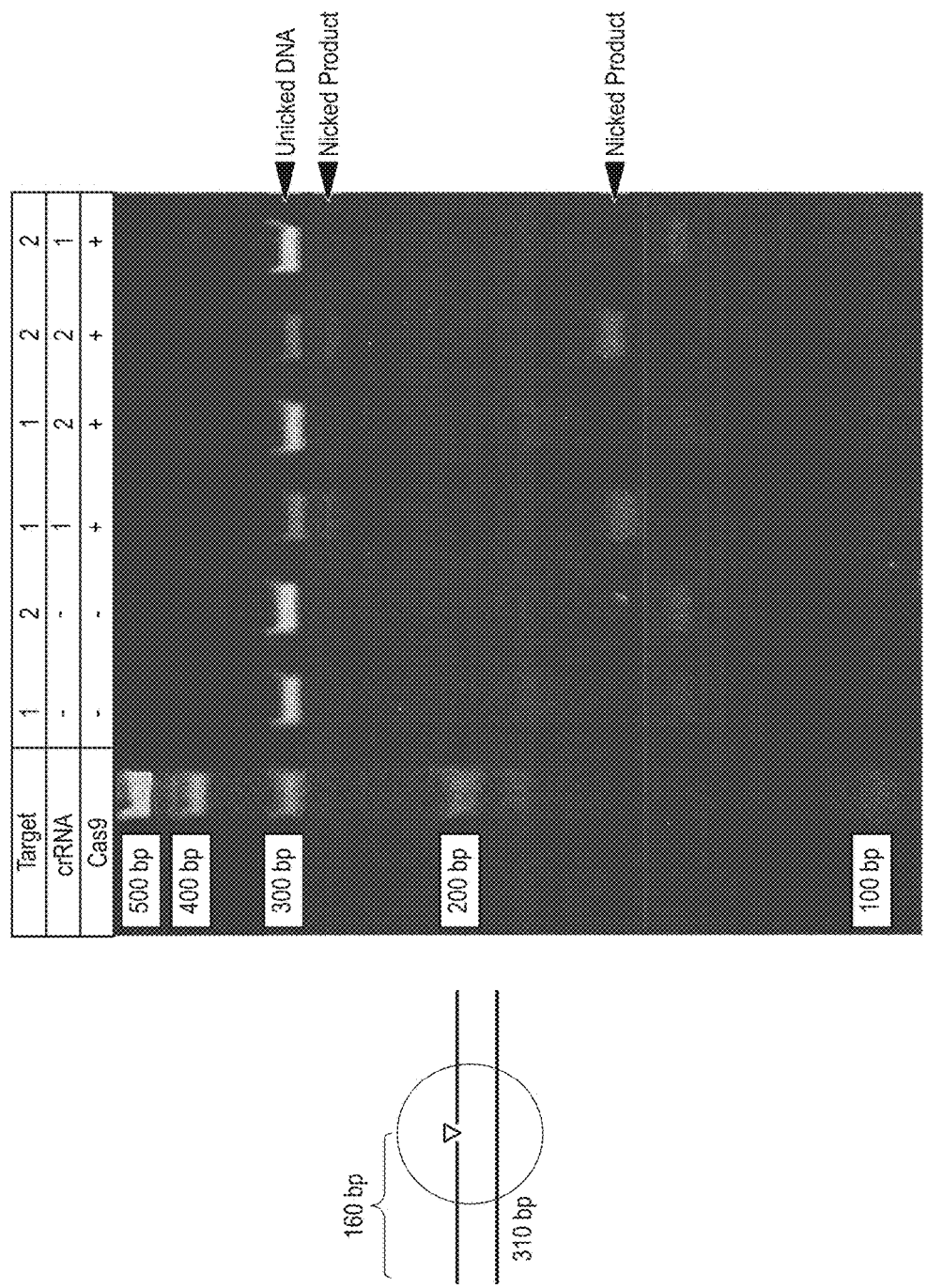
FIG. 6E shows the sequence specificity of the Cas9 nickase.

Panel on the left of FIG. 6E illustrates a 310 bp target amplicon depicted as two black lines representing two DNA strands with a top strand nicked by D10A nickase. D10A nickase recognition site is 160 bases away from the 5' end of target amplicon. Two amplicons (1 and 2) were individually digested for 72 hours with D10A nickase complexes formed with complimentary or non-complimentary crRNA:tracrRNA duplexes. As shown in FIG. 6E, nicked products are observed only when the target amplicon and crRNA are complimentary.

Example 5

Nick Translation

In this Example, the efficiency of incorporating different biotin-dNTP during a nick translation was analyzed using Streptavidin shift assay. After the nick translation was performed and various dNTP were incorporated into the translation products, Streptavidin was added to the reaction products and formed complex with the translation products by binding to biotin labeled dNTP. Then an electrophoretic mobility shift assay was performed to analyze the translation products.

Specifically, 3 ug of 120 bp long amplicon originated from HLA region of human genome containing a recognition site for Nb.BtsI nicking endonuclease was incubated for 1 hour at 37° C. with 5 units of Nb. BtsI in CutSmart™ Buffer (50 mM Potassium Acetate, 20 mM Tris-acetate, 10 mM Magnesium Acetate, 100 µg/ml BSA, pH 7.9). One crRNA and one tracrRNA were generated by in vitro transcription with T7 RNA polymerase, purified and crRNA (10 uM) was annealed with tracrRNA in equal molar ratio. crRNA:tracrRNA duplex (1 uM) was incubated with purified Cas9 D10A nickase (0.5 uM) at 37° C. for 10 minutes in a Cas9 cleavage buffer (20 mM HEPES pH 7.5, 150 mM KCl, 10 mM MgCl2, 0.5 mM DTT). Formed complex was incubated with a target DNA amplicon (0.025 uM) for 3 hours. Reaction was stopped by adding EDTA (10 mM) and complexes were purified with ZYMO DNA purification-concentration columns. Purified DNA was taken for a nick translation reaction. 20 ul nick translation reactions containing 10 ng of DNA amplicon, 50 uM of each dNTP, 10 uM of either Biotin-dGTP or Biotin-dUTP, nick translation buffer and 2 units of Bst DNA polymerase were incubated at 37° C. for 30 minutes, stopped by EDTA (50 mM) and purified with ZYMO DNA purification-concentration columns. Purified DNA was divided and one half was incubated for 10 min at room temperature with 10 ug of streptavidin. All samples were separated on 8% TBE PAAG and visualized with SYBR Gold stain.

Figure 7B:
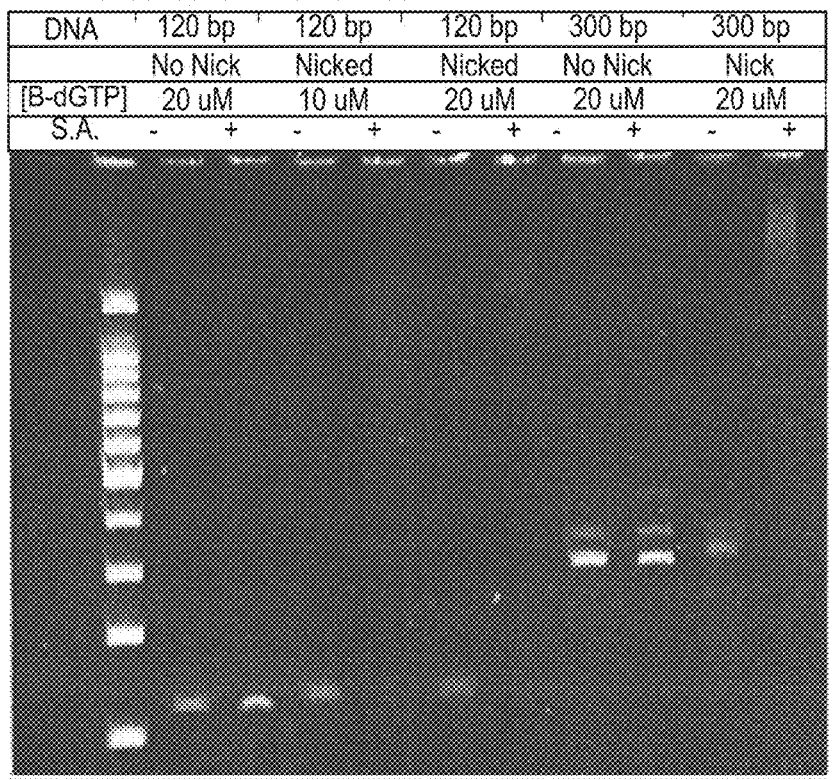
Figure 7B:
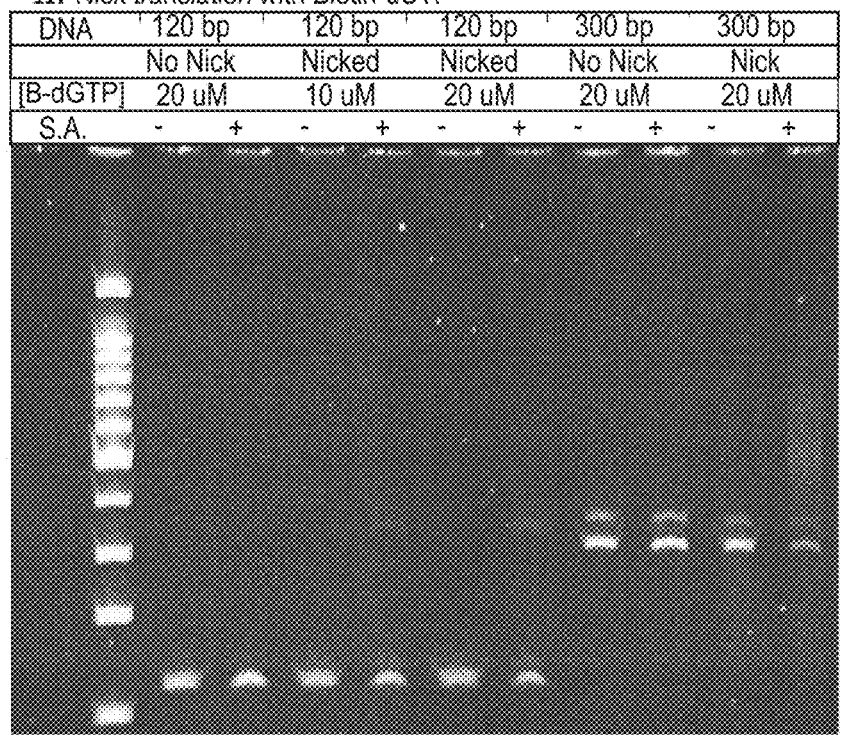

The results were shown in FIG. 7B. The left panel showed the gel shift assay results when biotin-dGTP was used during the nick translation. The right panel showed the gel shift assay results when biotin-dUTP was used during the nick translation. As shown, biotin-dGTP is more efficiently incorporated than biotin-dUTP, but was also non-specifically incorporated in non-nicked DNA.

DNA enrichment using nick translation was exemplified using Bst polymerase and biotin-dUTP. Three target DNA sequences were analyzed: HLA-A3 (100 bp), 1037 (300 bp), and 1216 (300 bp). The DNA enrichment was then quantified using quantitative PCR. Nick translations were performed on a 120 bp amplicon nicked with a nicking endonuclease Nb.BtsI and on a 300 bp amplicon nicked with Cas9 D10A nickase. Nick translation reaction mixtures were supplemented with either Biotin-dGTP (panel I) or Biotin-dUTP (panel II). After nick translation, a half of each sample was taken for a streptavidin-shift assay (S.A), followed by an analysis on 8% TBE-PAAG. In this nick translation experiment, Bst DNA polymerase was used.

Specifically, 3 ug of amplicon originated from HLA region of human genome containing a recognition site for Nb.BtsI nicking endonuclease was incubated for 1 hour at 37° C. with 5 units of Nb. BtsI in CutSmart™ Buffer (50 mM Potassium Acetate, 20 mM Tris-acetate, 10 mM Magnesium Acetate, 100 µg/ml BSA, pH 7.9). Two crRNA and one tracrRNA were generated by in vitro transcription with T7 RNA polymerase, purified and each crRNA (10 uM) was annealed with tracrRNA in equal molar ratio. crRNA:tracrRNA duplexes (1 uM) was incubated with purified CAS9 D10A nickase (0.5 uM) at 37 C for 10 minutes in a Cas9 cleavage buffer (20 mM HEPES pH 7.5, 150 mM KCl, 10 mM MgCl2, 0.5 mM DTT). Formed complexes were incubated with a target DNA amplicons (0.025 uM) for 3 hours. Reaction was stopped by adding EDTA (10 mM) and complexes were purified with ZYMO DNA purification-concentration columns. Purified DNA was taken for a nick translation reaction in a background of genomic DNA library, prepared using Illumina's v2 Nextera Library Prep kit according to the manufactures protocol (available from Illumina Inc., San Diego, Calif.). 20 ul nick translation reactions containing 0.5 ng of DNA amplicon, 100 ng of genomic DNA library, 50 uM of each dNTP, 10 uM of Biotin-dUTP, nick translation buffer and 2 units of Bst DNA polymerase were incubated at 37° C. for 30 minutes and stopped by EDTA (10 mM). Biotinylated DNA pulled down with 40 ul of streptavidin magnetic beads were pre-bound with 100 ng gDNA and 100 ug BSA. Beads were consequently washed with high and low salt washing buffers and targeted amplicon was eluted from the beads with NaOH followed by pH neutralization. Appropriate dilutions of eluted material and input control were analyzed by qPCR with primers specific to targeted amplicons and human AluSx5 repeat, used as a normalization control.

Figure 7C:
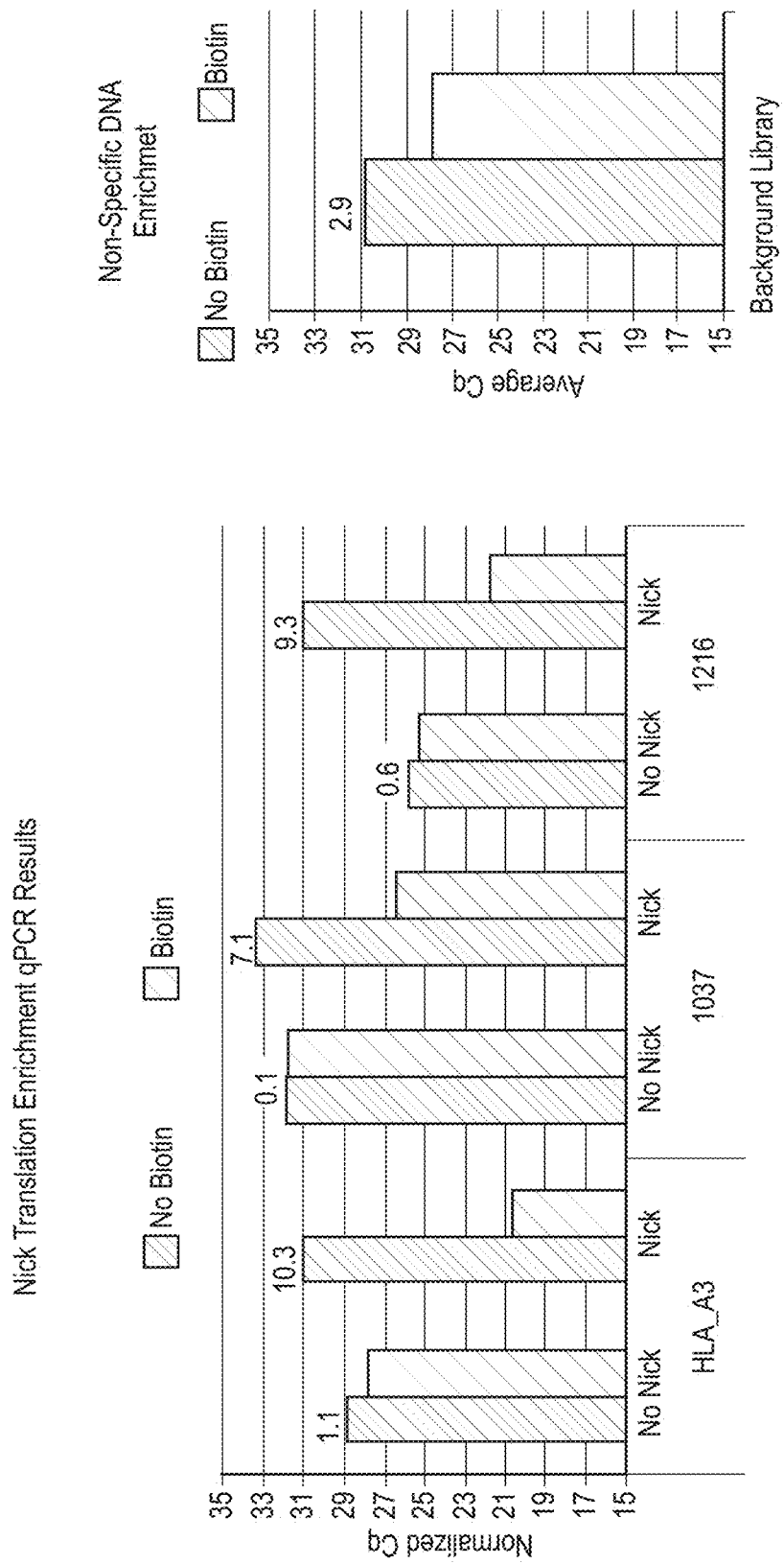

Results were shown in FIG. 7C, left panel presents the results of qPCR analysis for three different amplicons (HLA_A3, 1037 and 1216) enriched in a streptavidin pull down assay following nick translation of target amplicons. Nicked (Nick) or unnicked (No Nick) target DNA amplicons were spiked into 100 ng of genomic DNA library, nick translated with or without Biotin-dUTP (Biotin/No Biotin) and resulted biotinylated DNA was pulled down with magnetic streptavidin beads. Right panel presents the results of qPCR analysis of genomic DNA library carried over in pull down assay. Gray bars represent normalized Cq values and numbers on top of the bars depict fold enrichment for different amplicons and genomic DNA library. As shown, enrichment of target DNA was observed only for conditions that contained nicked targets and Biotin-dUTP in the nick translation reaction mixture.

Example 6

Figure 8B:
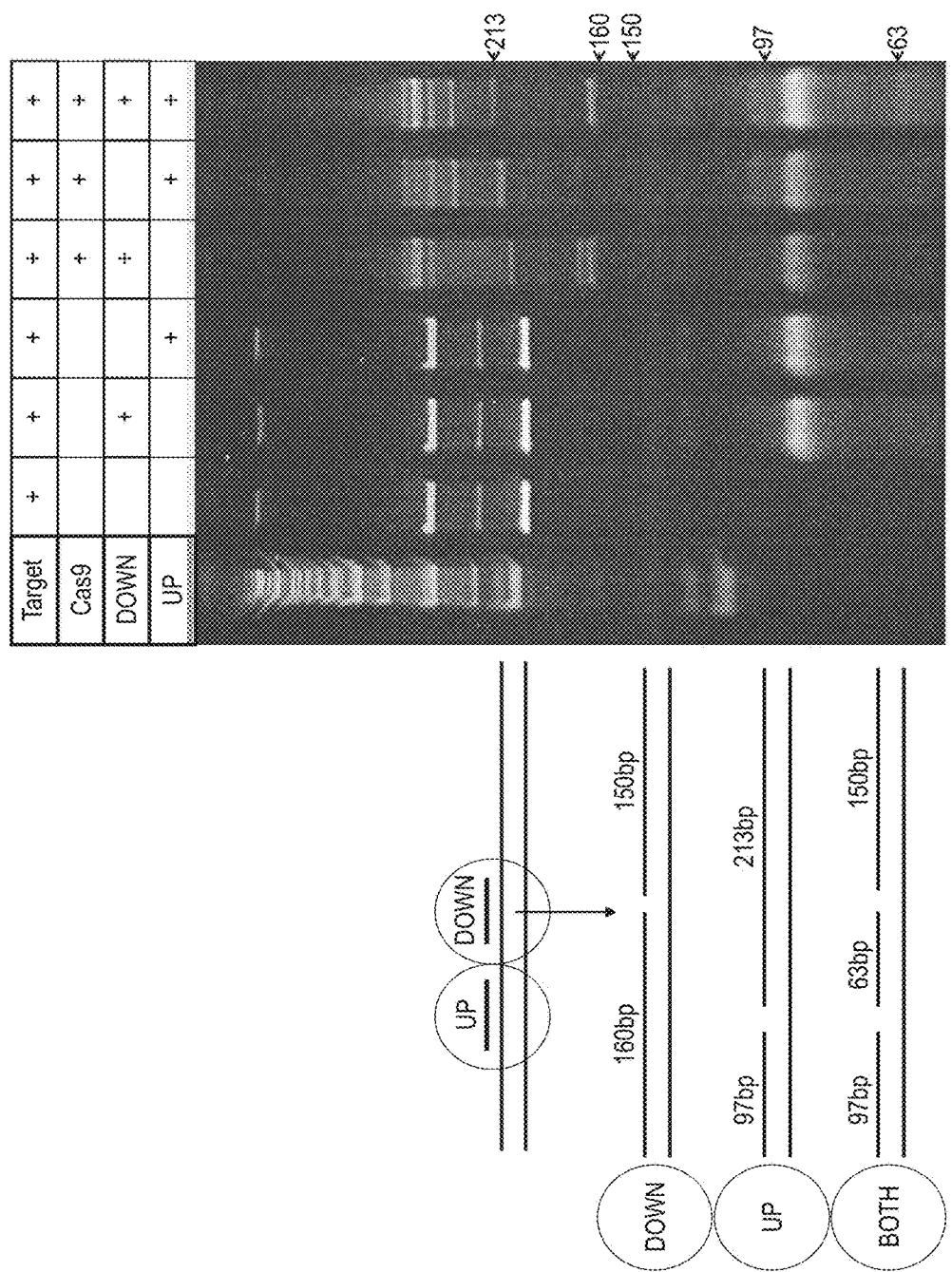

Enriching Target DNA by Generating Double Nicks Using CRISPR-Cas Systems Containing Cas9 Nickases Enrichment of target DNA by generating double nicks on the same DNA strand using CRISPR-Cas systems was illustrated in this example. A 230 bp double-stranded DNA was treated with two Cas9 nickase systems. Each system could generate a nick on the same DNA strand as shown in the left panel of FIG. 8B.

Two crRNA and one tracrRNA were generated by in vitro transcription with T7 RNA polymerase, purified and each crRNA (10 uM) was annealed with tracrRNA in equal molar ratio. Each crRNA:tracrRNA duplex (1 uM) was incubated with purified CAS9 nickase (0.5 uM) at 37° C. for 15 minutes in a Cas9 cleavage buffer (20 mM HEPES pH 7.5, 150 mM KCl, 10 mM MgCl2, 0.5 mM DTT). Formed complexes were pulled and incubated with target DNA amplicon (0.025 uM) for indicated time. Reaction was stopped by complex purification with ZYMO DNA purification-concentration columns and analyzed on 8% TBE-Urea PAAG. The results were shown in the right panel of FIG. 8B. As shown, double nicking occurred as evidenced by a 63 bp DNA fragment.

The 63 bp single-stranded DNA fragment generated as a result of double nicking on the same strand can be displaced with a probe as discussed above, which was illustrated in this example. After treatment with Cas9 nickase systems to 2.5 ng of 300 bp amplicon, a 60mer biotinylated probe was added and hybridized to the target DNA. Specifically, target DNA (0.005 uM) was nicked for 3 hours in CAS9 cleavage buffer with CAS9 complexes (0.1 uM) containing either one or two crRNA:tracrRNA duplexes (0.05 uM). Nicking reactions were stopped by complexes purification with ZYMO DNA purification-concentration columns. Resulting purified DNA (4 nM) was mixed with 100 fold molar excess of biotinylated capture probe, and different aliquots, containing 100 ng of human genomic library DNA were incubated for 2 minutes at 85° C., 75° C., 70° C., 65° C., 60° C. followed by gradual cooling to 40° C. Unnicked target amplicon was subjected to the same denaturation-annealing conditions side by side with samples without biotinylated capture probe. Formed heteroduplexes of nicked amplicon and biotinylated capture probe were pulled down with streptavidin coated magnetic beads, and blocked with genomic DNA to prevent nonspecific target amplicon binding. Beads were consequently washed twice with high and low salt washing buffers and the targeted amplicon was eluted from the beads with NaOH followed by pH neutralization. Appropriate dilutions of eluted material and input control were analyzed by qPCR with primers specific to targeted amplicon and human AluSx5 repeat, used as a normalization control.

The results were shown in FIG. 8E. As shown, there was no enrichment when no capture probe was added; under complete denaturing conditions, enrichment was seen for all target DNAs. Under partially denaturing conditions, targeted enrichment of nicked DNA was observed. qPCR results show successful enrichment of amplicon nicked on the same strand with two Cas9 nickases.

Figure 8C:
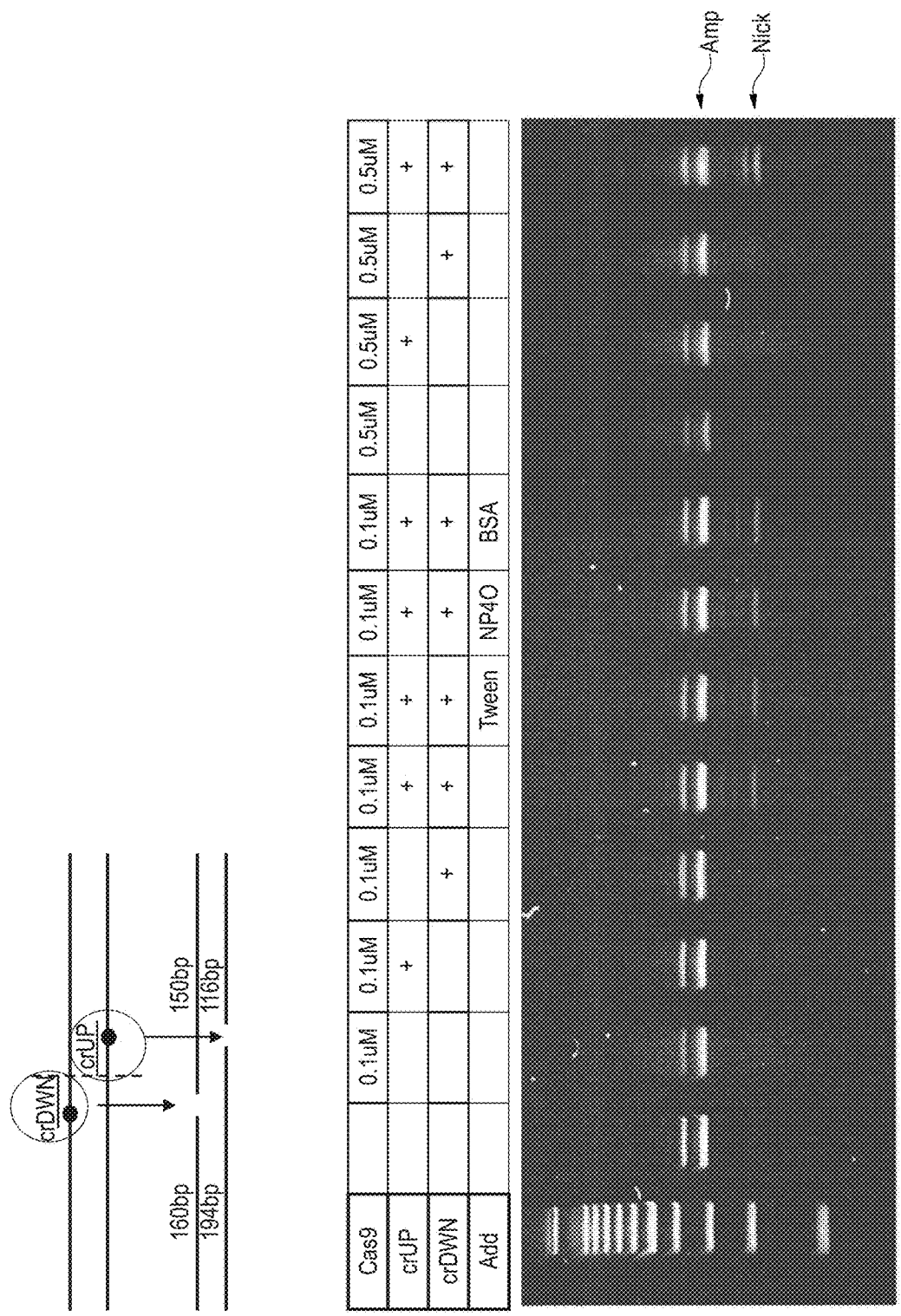

Enrichment of target DNA by generating double nicks on opposite DNA strands using CRISPR-Cas systems was also illustrated in this example. As shown in FIG. 8C, nicking on opposite strands of a 300 bp amplicon was performed, and the fragments generated were analyzed using gel electrophoresis.

Specifically, target DNA was incubated for 3 hours at 37° C. in Cas9 cleavage buffer with different components of Cas9 nicking reaction as depicted on a top of the gel image. Nicking reactions were stopped by complex purification with ZYMO DNA purification-concentration columns. Aliquots of eluted samples were loaded on native 8% PAAG. The results were shown in FIG. 8C. Top two bands represent original DNA amplicon, and faster migrating bands in lanes with both crRNAs represent nicked products.

Figure 8D:
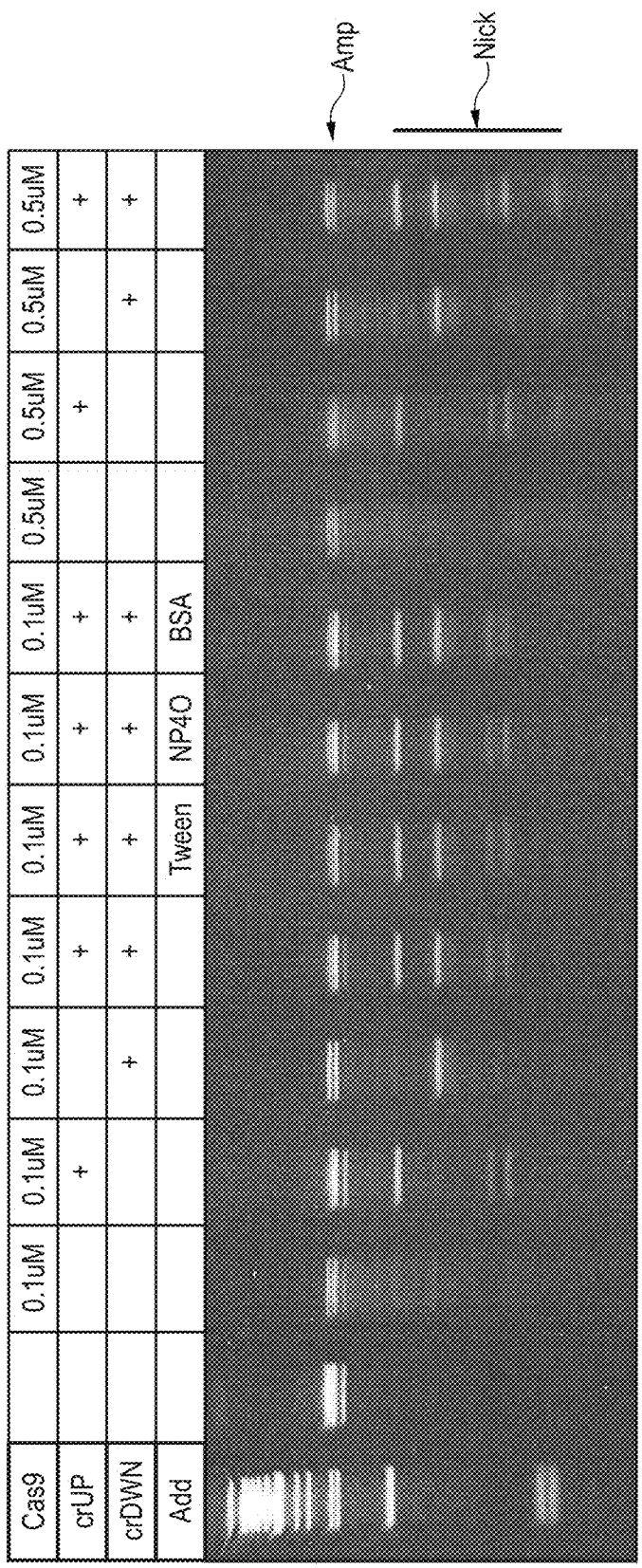

FIG. 8D shows 8% PAAG gel analysis of original and nicked targeted amplicon after brief incubation at 75° C. Target DNA was incubated for 3 hours at 37° C. in Cas9 cleavage buffer with different components of Cas9 nicking reaction as depicted on a top of the gel image. Nicking reactions were stopped by complex purification with ZYMO DNA purification-concentration columns. Aliquots of eluted samples were incubated at 75° C. for 3 minutes, immediately transferred on ice, and loaded on a gel. Top two bands represent original DNA amplicon, faster migrating bands in lane with single of both crRNAs correspond to nicked products. As shown, single-stranded DNAs with proper size were generated.

Example 7

Cas9 Mediated Target Enrichment of BRAF Target DNA

Figure 13:
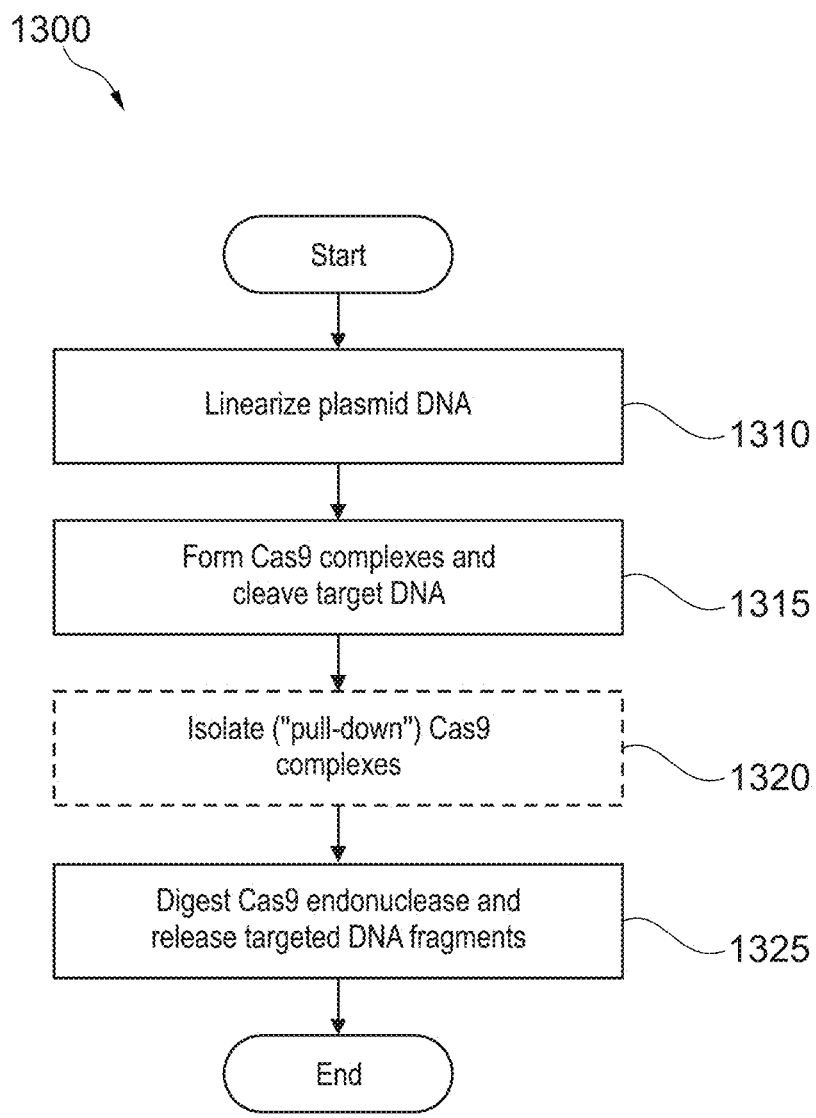
FIG. 13 illustrates a flow diagram of an example of a Cas9 cleavage assay.

FIG. 13 illustrates a flow diagram of an example of a Cas9 cleavage assay 1300. Cas9 cleavage assay 1300 may include, but is not limited to, the following steps.

At a step 1310, a plasmid comprising a target DNA sequence is linearized by restriction endonuclease digestion. In one example, the target DNA sequence is a BRAF DNA sequence and the plasmid is linearized by AlwNI restriction endonuclease digestion.

At a step 1315, Cas9 endonuclease complexes are formed and targeted BRAF DNA sequences are cleaved. The Cas9 endonuclease complex comprises Cas9 endonuclease, a target-specific crRNA, and an auxiliary tracrRNA. crRNA and tracrRNA form a "guide RNA" that targets Cas9 endonuclease to the targeted DNA sequence for double-strand DNA cleavage. In one example, Cas9 endonuclease is a wild type Cas9 endonuclease that cleaves both strands of a targeted DNA sequence. In one example, crRNA and/or tracrRNA are labeled with a tag such as a biotin tag (i.e., crRNA and tracrRNA are biotinylated). In another example, crRNA and tracrRNA are unlabeled.

At an optional step 1320, Cas9 complexes are isolated using streptavidin coated magnetically responsive beads. The Cas9 complexes with fragmented target BRAF DNA therein are bound to the surface of the streptavidin coated beads via a biotin-streptavidin binding complex formed between the biotinylated crRNA and tracrRNA and streptavidin coated beads.

At a step 1325, Cas9 endonuclease is digested using a protease reaction to release targeted and cleaved BRAF DNA fragments. The released BRAF DNA fragments are detected, for example, by agarose gel electrophoresis.

Figure 14:
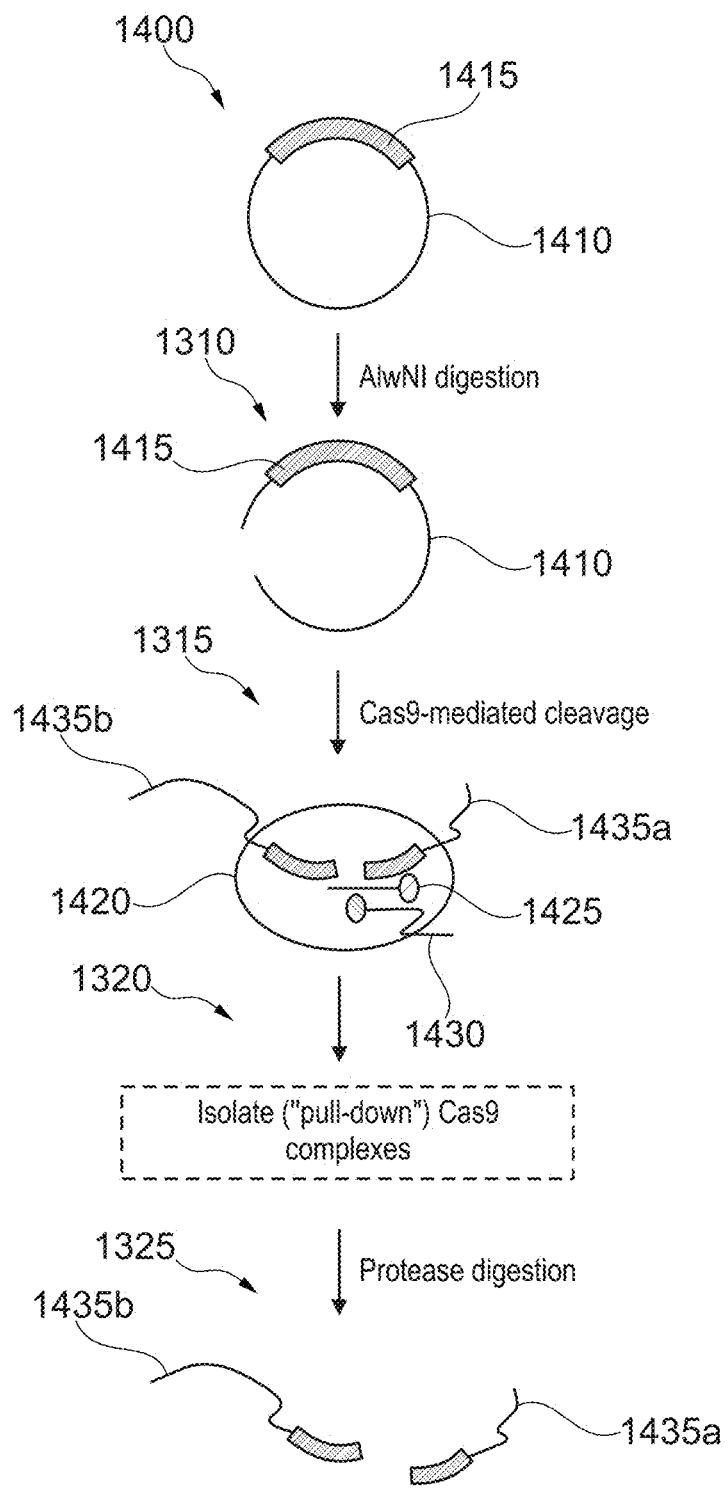
FIG. 14 shows pictorially the steps of the Cas9 cleavage assay of FIG. 13.

FIG. 14 shows pictorially the steps of Cas9 cleavage assay 1300 of FIG. 13. Namely, a plasmid 1410 includes a target BRAF DNA sequence 1415. At step 1310 of Cas9 cleavage assay 1300, plasmid 1410 is linearized by AlwNI restriction endonuclease digestion. In this example, plasmid 1410 is about 3582 bp in size. At step 1315 of Cas9 cleavage assay 1300, Cas9 complexes comprising Cas9 endonuclease 1420, a target-specific crRNA 1425 (e.g., a BRAF specific crRNA), and a tracrRNA 1430 are formed. Target-specific crRNA 1425 and tracrRNA 1430 form a "guide RNA" that targets Cas9 endonuclease 1420 to target BRAF DNA sequence 1415 in plasmid 1410. In this example, target-specific crRNA 1425 and tracrRNA 1430 are biotinylated. In another example (not shown), target-specific crRNA 1425 and tracrRNA 1430 are not labeled. Target BRAF DNA sequence 1415 is cleaved by Cas9 endonuclease 1420 to generate a pair of Cas9 cleavage fragments 1435, i.e., fragment 1435a of about 1242 bp and fragment 1435b of about 2340 bp, that each comprise a portion of target BRAF DNA sequence 1415. At optional step 1320 of Cas9 cleavage assay 1300, streptavidin coated magnetically responsive beads are used to "pull-down" Cas9 complexes and fragments 1435a and 1435b therein. At step 1325 of Cas9 cleavage assay 1300, Cas9 endonuclease 1420 is digested using a protease reaction and fragments 1435a and 1435b are released.

Figure 15:
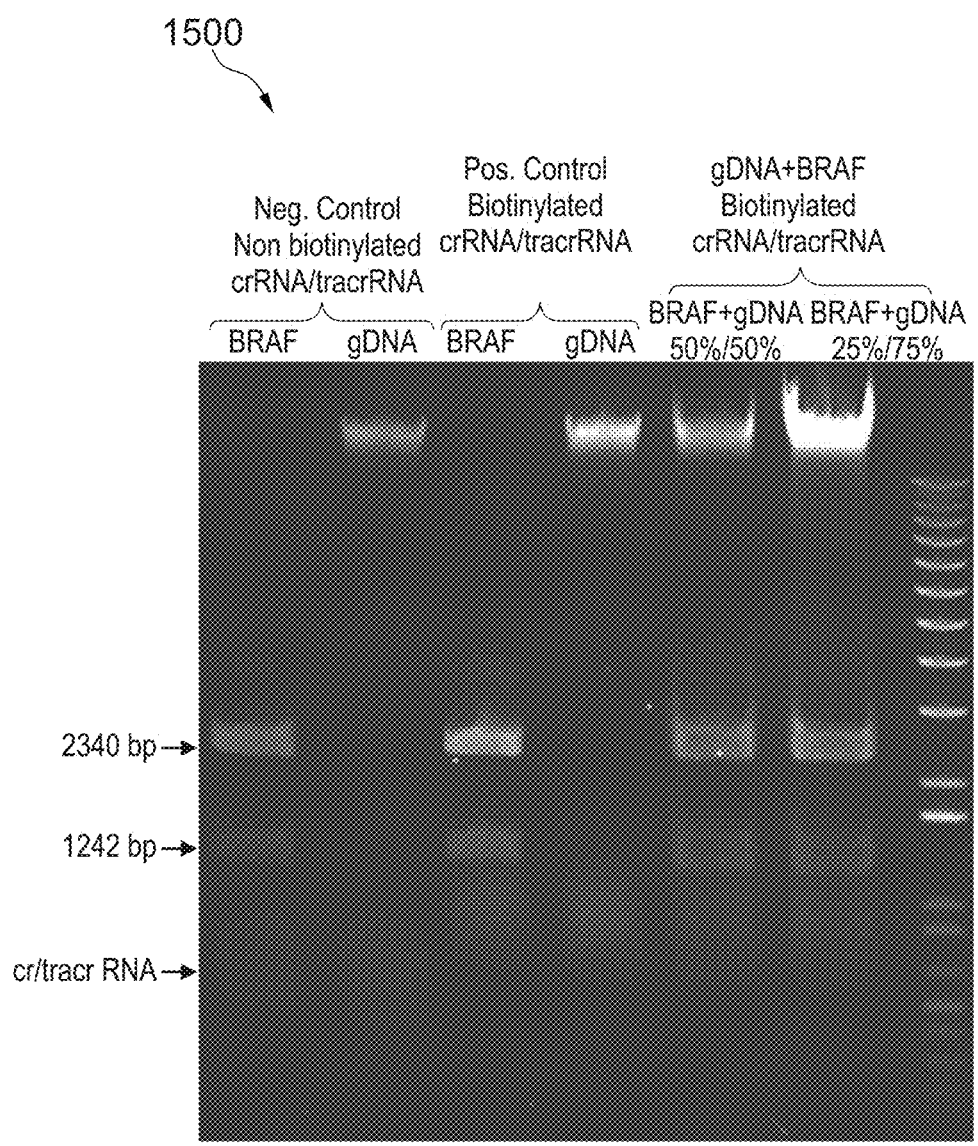
FIG. 15 shows a photograph of an agarose gel of the fragmentation of BRAF plasmid DNA alone or in a mixture comprising BRAF plasmid DNA and genomic DNA using the Cas9 cleavage assay of FIG. 13.

FIG. 15 shows a photograph 1500 of an agarose gel of the fragmentation of BRAF plasmid DNA alone or in a mixture comprising BRAF plasmid DNA and genomic DNA using Cas9 cleavage assay 1300 of FIG. 13. In this example, the Cas9 endonuclease was a wild type endonuclease. Negative control reactions ("Neg. Control") were performed using non-biotinylated crRNA and tracrRNA. Positive control reactions ("Pos. Control") were performed using biotinylated crRNA and tracrRNA. crRNA and tracrRNAs were prepared using an in vitro transcription kit (i.e., Biotin IVT kit). Dual biotinylated crRNA and tracrRNA were also obtained from Bio-Synthesis Inc. In general, dual biotinylated crRNA or tracrRNA yielded better pull down results. Non biotinylated crRNA and tracrRNAs were prepared using an in vitro transcription (ASF3507 (AmpliScribe™ T7-Flash™ Transcription Kit (Epicentre, Illumina)). The experiment was performed using BRAF plasmid DNA alone ("BRAF"), genomic DNA ("gDNA") or mixtures of BRAF plasmid DNA plus genomic DNA (i.e., 50% BRAF+50% gDNA or 25% BRAF+75% gDNA, by weight percent). Cleavage fragments (i.e., 2340 bp and 1242 bp fragments) were detected by agarose gel electrophoresis. The data show that in both the negative control ("Neg. Control") and positive control ("Pos. Control") reactions, the targeted BRAF plasmid DNA was fragmented by Cas9 complexes, while the genomic DNA (gDNA) was not significantly cleaved. The data also show that cleavage of targeted BRAF plasmid DNA in a mixed sample of BRAF plasmid DNA and genomic DNA was not significantly affected by the amount of genomic DNA, i.e., different amounts of gDNA did not interrupt Cas9 cleavage of BRAF plasmid.

Figure 16:
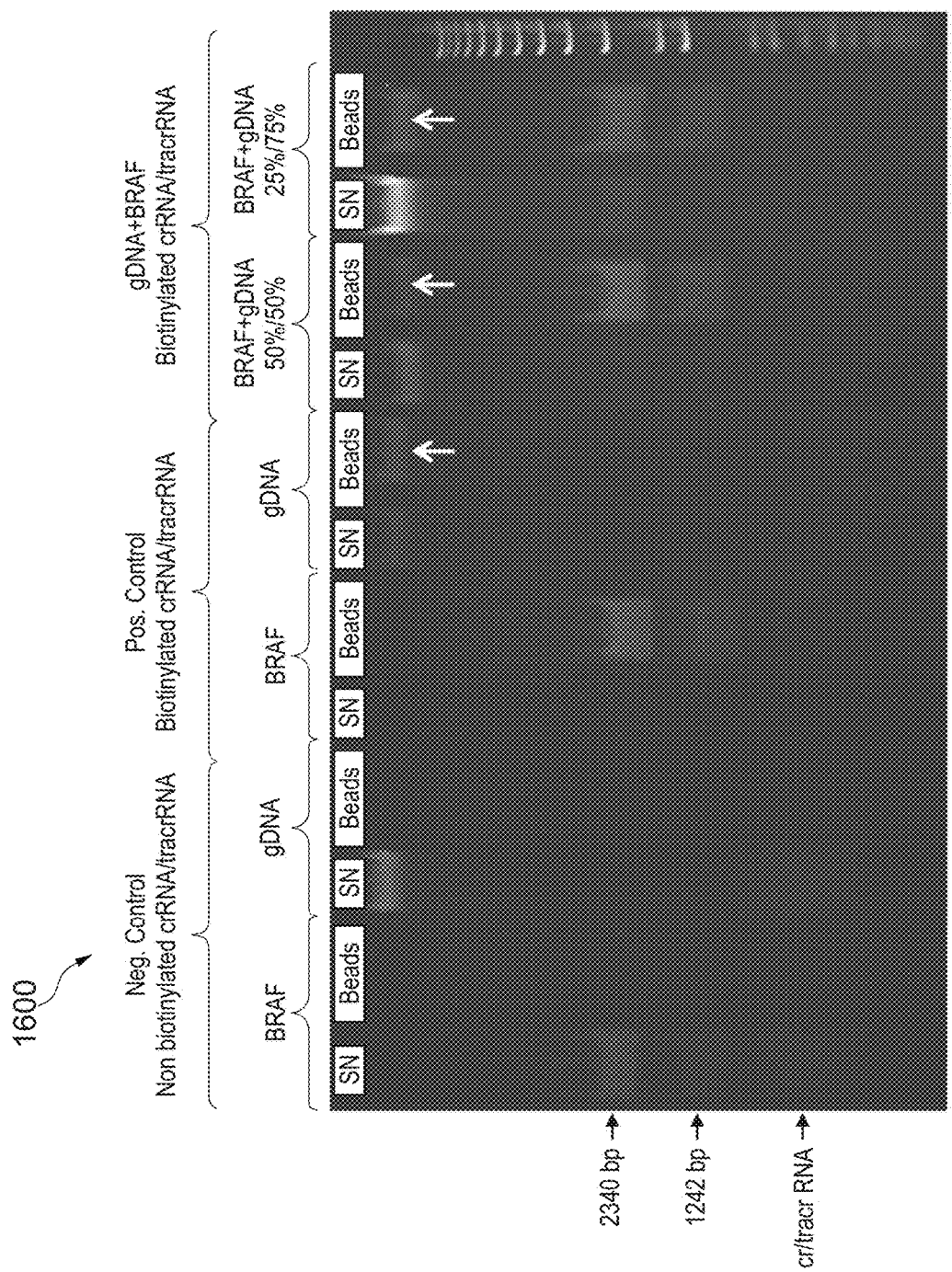
FIG. 16 shows a photograph of an agarose gel of Cas9-mediated pull-down (enrichment) of the fragmented BRAF plasmid DNA of FIG. 15.

FIG. 16 shows a photograph 1600 of an agarose gel of Cas9-mediated pull-down (enrichment) of the fragmented BRAF plasmid DNA of FIG. 15. In this example, streptavidin coated magnetic beads were used to pull-down and isolate Cas9 complexes (optional step 1320 of Cas9 cleavage assay 1300 of FIG. 13) prior to protease digestion and elution of fragmented target DNA sequences (step 1325 of Cas9 cleavage assay 1300). The supernatant (SN) fraction and bead-elution fraction ("Beads") were examined for BRAF DNA cleavage fragments (i.e., 2340 bp and 1242 bp fragments) by agarose gel electrophoresis. The data show that in the negative control samples (Neg. Control), BRAF cleavage fragments and human genomic DNA (gDNA) were detected only in the supernatant fraction (SN). In the positive control samples (Pos. Control) and mixed BRAF+ gDNA samples, BRAF cleavage fragments were detected in the eluted bead fraction. Genomic DNA (indicated by arrows) non-specifically pulled-down by Cas9 complexes was also detected in the eluted bead fraction.

To determine the largest fragment that can be pulled down using Cas9 complexes, HindIII digested lambda DNA fragments were used in Cas9 cleavage and pull down assays.

Figure 17:
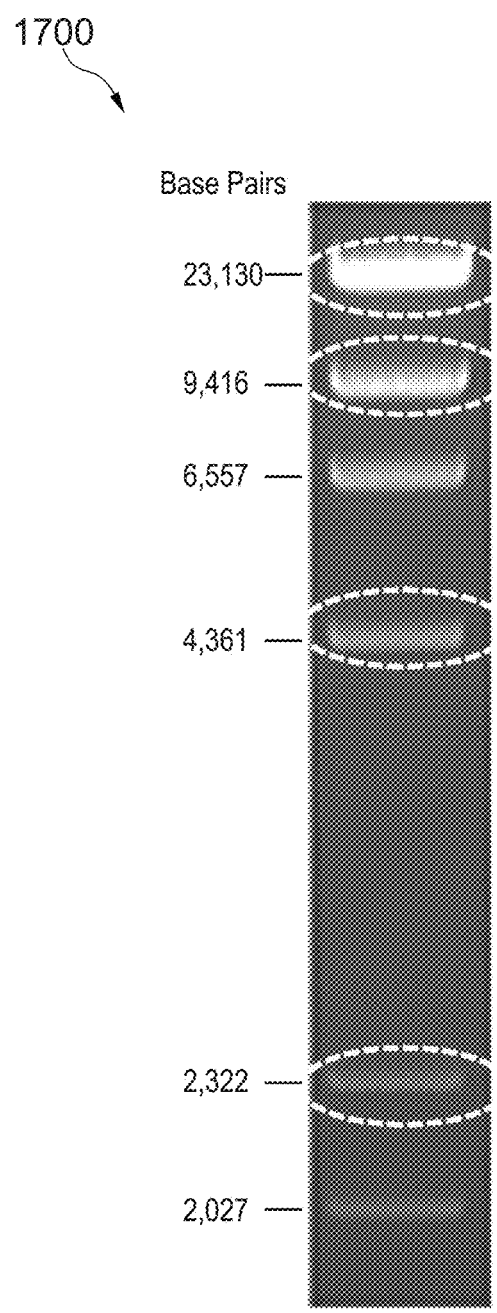
FIG. 17 shows a photograph of the fragment size distribution of HindIII digested phage lambda DNA.

FIG. 17 shows a photograph 1700 of the fragment size distribution of HindIII digested phage lambda DNA. Four different crRNAs were designed to target and cleave the 23.13 kb, 9.4 kb, 4.4 kb, and 2.3 kb HindIII fragments of lambda DNA. The expected Cas9-mediated cleavage fragment sizes for each lambda HindIII fragment are shown in Table 1.

TABLE 1

| Cas9 cleavage of phage lambda DNA fragments | |
|---|---|
| Lambda HindIII Fragment (kb) | Cas9 Cleavage Fragments (kb) |
| 23.13 | 11.72 and 11.41 |
| 9.4 | 5.1 and 4.3 |
| 4.4 | 2.3 and 2.1 |
| 2.3 | 1 and 1.3 |

Figure 18:
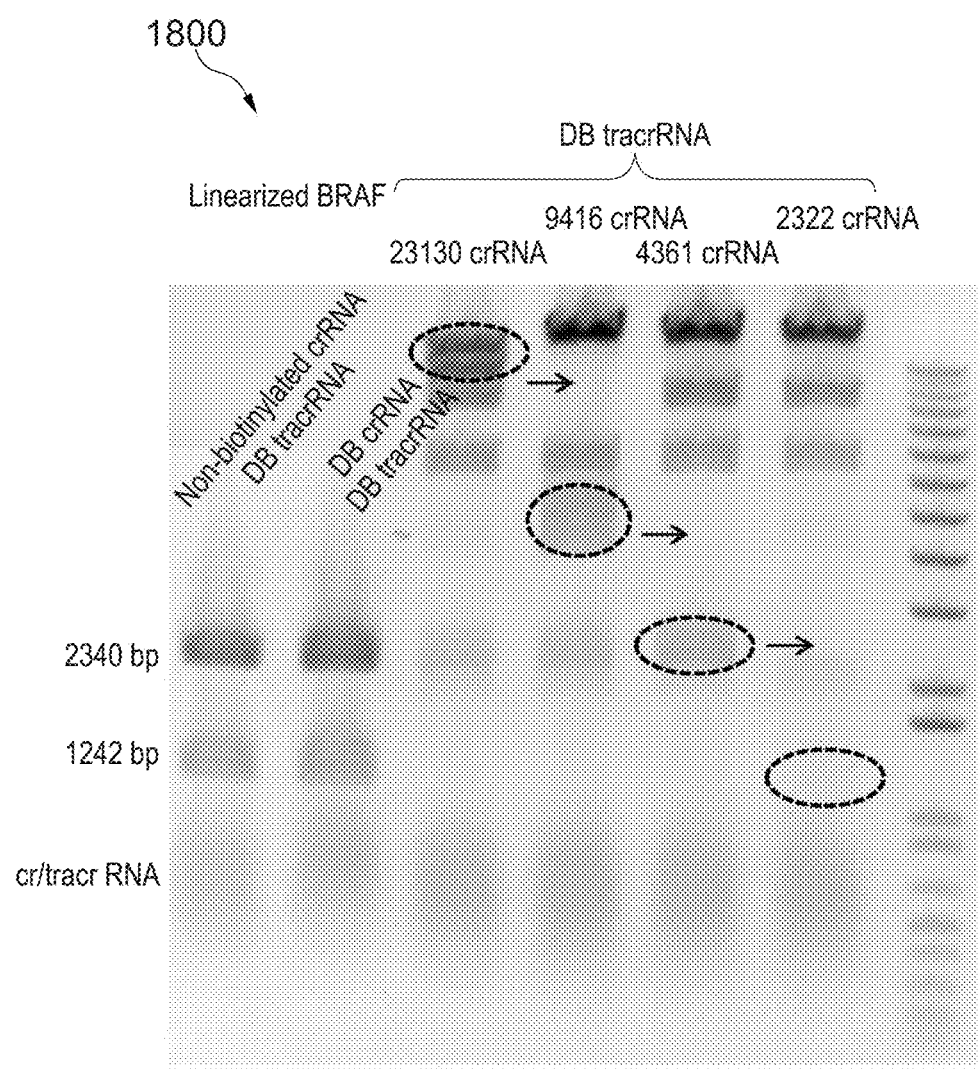
FIG. 18 shows a photograph of an agarose gel of Cas9-mediated cleavage of lambda HindIII-DNA fragments.

FIG. 18 shows a photograph 1800 of an agarose gel of Cas9-mediated cleavage of lambda HindIII-DNA fragments. In this example, Cas9 complexes were formed using 500 nM wild type Cas9 endonuclease, 500 nM dual biotin-labeled (DB) tracrRNA, 500 nM crRNA (unlabeled) and 500 ng HindIII digested lambda DNA. The cleavage reaction was performed in 1× CutSmart buffer. The crRNAs targeting the 23.13, 9.4, 4.4, and 2.3 kb lambda HindIII fragments are designated by 23130 crRNA, 9416 crRNA, 4361 crRNA, and 2322 crRNA, respectively. For each HindIII digested lambda fragment, the position of the expected Cas9-mediated cleavage fragments are indicated by circles. An arrow indicates the expected position of each uncleaved lambda HindIII fragment. BRAF plasmid DNA and dual biotin (DB)-labeled tracrRNA and/or dual biotin (DB)-labeled crRNA were used as a cleavage and pull-down control samples. The data show Cas9-mediated cleavage of all fragment sizes, i.e., 23.13, 9.4, 4.4, and 2.3 kb lambda HindIII fragments.

Figure 19:
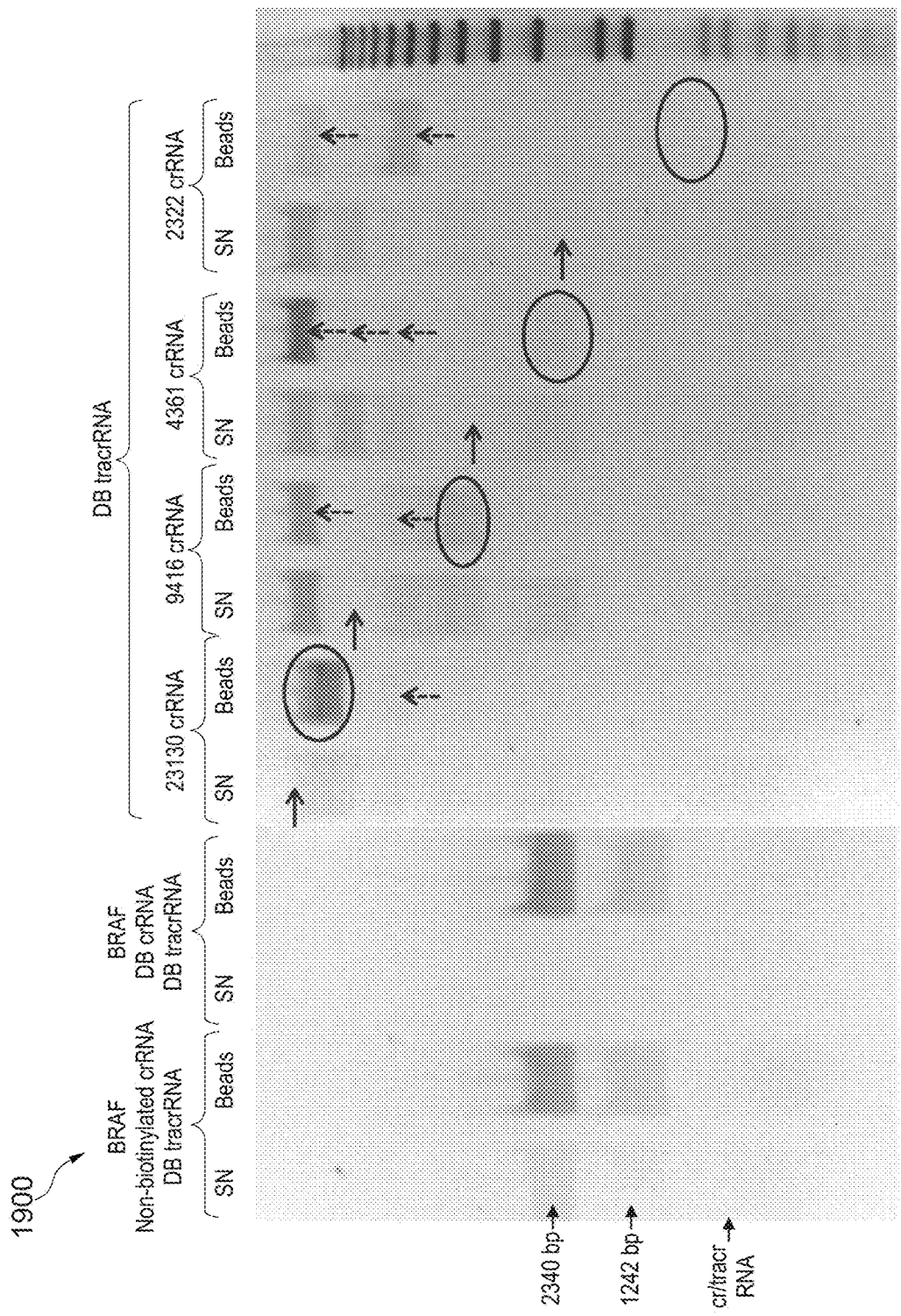
FIG. 19 shows a photograph of an agarose gel of Cas9-mediated pull-down (enrichment) of the targeted and cleaved lambda DNA fragments of FIG. 18.

FIG. 19 shows a photograph 1900 of an agarose gel of Cas9-mediated pull-down (enrichment) of the targeted and cleaved lambda DNA fragments of FIG. 18. The pull-down assay was performed essentially as described with reference to FIG. 16 except that 500 mM NaCl was added to the bead washing buffer. For each HindIII digested lambda fragment, the position of the expected Cas9-mediated cleavage fragments are indicated by circles. A solid arrow indicates the expected position of each uncleaved HindIII digested lambda fragment. BRAF plasmid DNA and dual biotin (DB)-labeled tracrRNA and/or dual biotin (DB)-labeled crRNA were used as a cleavage and pull-down control samples. The data show Cas9-mediated pull-down of the cleaved lambda DNA fragments. Off-target binding (non-specific binding) of Cas9 complexes (indicated by dashed arrows) was also observed in the eluted bead fractions.

The HindIII digested lambda fragment pull-down assay described with reference to FIG. 19 was repeated using a D10A mutant nickase version of Cas9 endonuclease (designated as "Cas9-nickase"). Cas9-nickase creates a single strand break in double stranded DNA but does not generate a double strand break (i.e., it does not cleave the HindIII digested lambda fragments).

Figure 20:
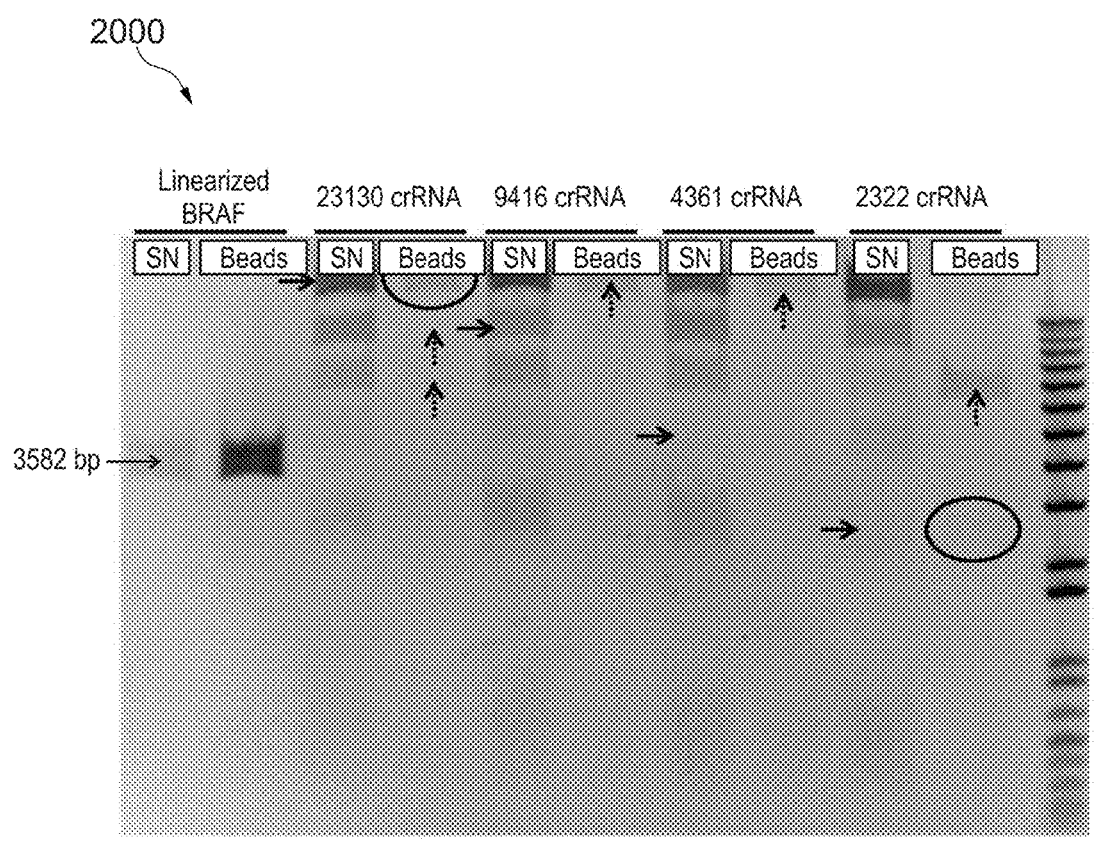
FIG. 20 shows a photograph of an agarose gel of Cas9-nickase-mediated pull-down of lambda HindIII fragments.

FIG. 20 shows a photograph 2000 of an agarose gel of Cas9-nickase-mediated pull-down of HindIII digested lambda fragments. In this example, the pull-down was performed at 37° C. and 500 mM NaCl was added to the bead washing buffer. For each HindIII digested lambda fragment (i.e., 23.13, 9.4, 4.4, and 2.3 kb designated as 23130 crRNA, 9416 crRNA, 4361 crRNA, and 2322 crRNA, respectively), a solid black arrow indicates the expected position of the uncleaved fragment. Linearized BRAF plasmid DNA (3582 bp) was used as a pull-down control. The data show that, as expected, HindIII digested lambda fragments and linearized BRAF plasmid DNA were not cleaved by Cas9-nickase. The data also shows that linearized BRAF plasmid DNA was pulled-down by Cas9-nickase. Pull-down of HindIII digested lambda fragments was only observed for the 23.13 kb and 2.3 kb fragments (indicated by circles). Off-target binding (non-specific binding) of Cas9-nickase complexes (indicated by dashed arrows) was also observed in the eluted bead fractions. The pattern of off-target binding that was observed is different from the pattern observed with the wild type Cas9 complex.

Subsequent experiments (not shown) have demonstrated that more stringent pull-down conditions using Cas9 cleavage and a pull-down incubation temperature of 48° C. and 500 mM NaCl, as well as stringent bead washing at 48° C. and in the presence of 500 mM NaCl can be used to substantially improve the specificity of a pull-down reaction.

Figure 21:
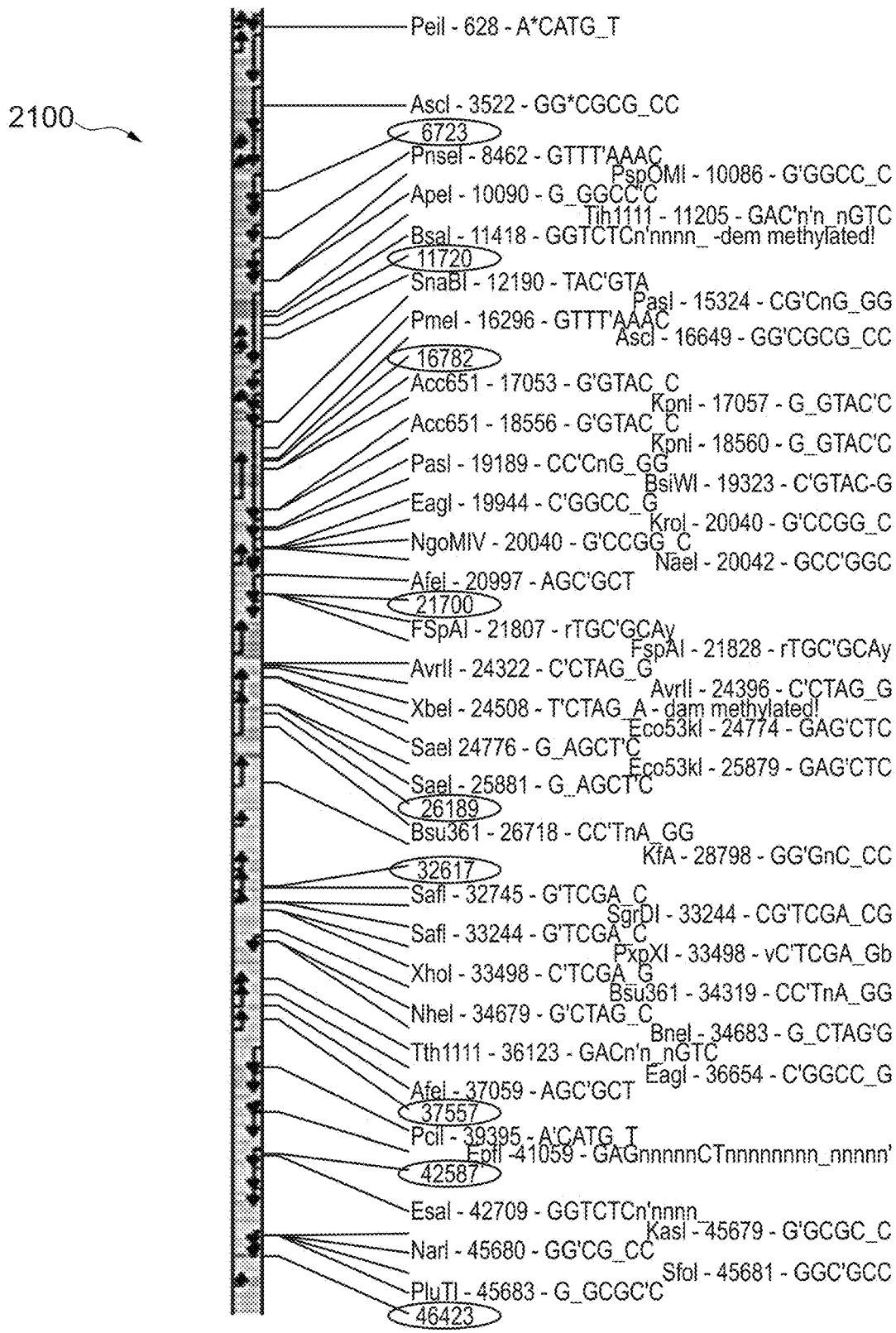
FIG. 21 shows a genomic map of lambda DNA and 9 Cas9 target positions for crRNA design for multiplex enrichment.

To evaluate the multiplexing capability of Cas9-nickase in a library enrichment protocol, nine crRNAs and biotinylated probes were designed for 9 different regions of lambda DNA. FIG. 21 shows a genomic map 2100 of lambda DNA (genome size=48502 bp). The circled sites on genomic map 2100 indicate the targeted regions of the lambda DNA. The biotinylated probes are oligonucleotides that target the displacement loop of each target lambda DNA region in the Cas9-D10A nickase complex. The target lambda DNA regions are at positions 6723, 11720, 16782, 21700, 26189, 32617, 37557, 42587, and 46423 of the lambda genome (indicated by circles).

Figure 22:
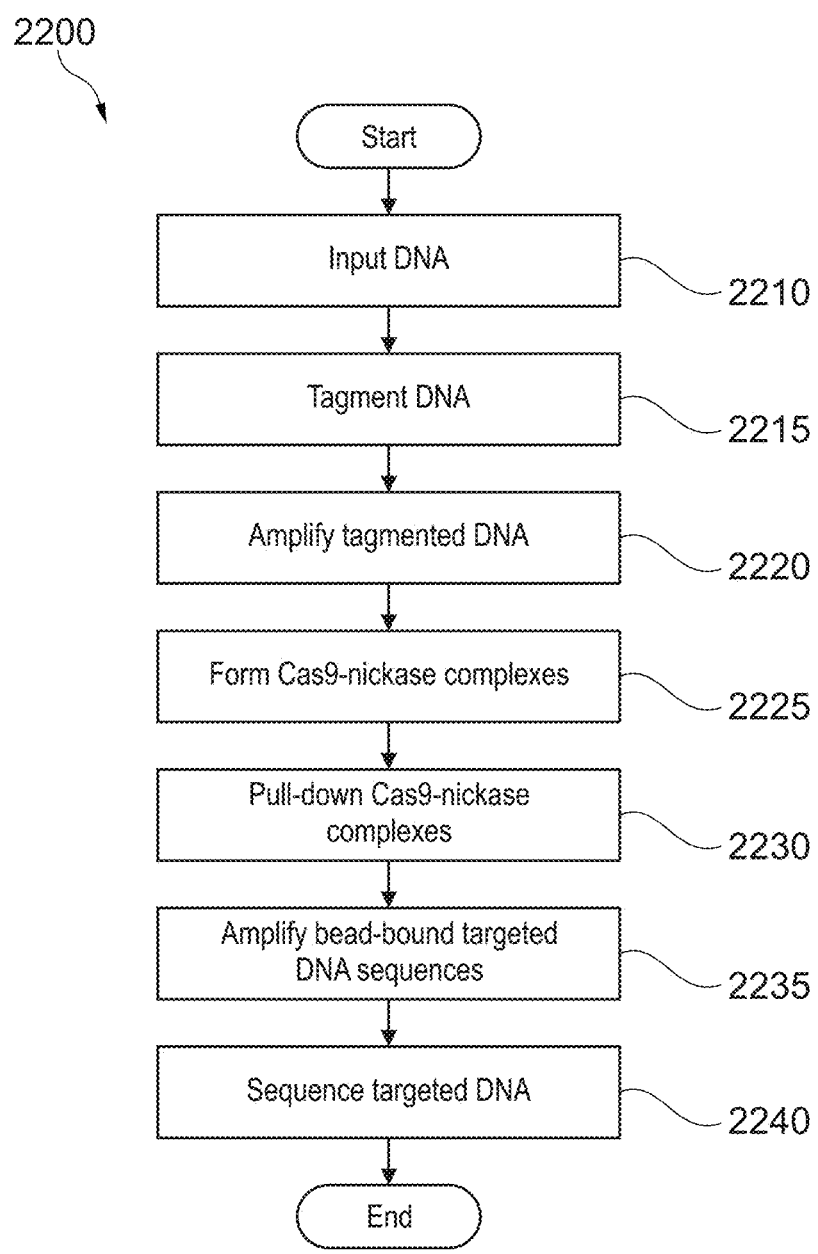
FIG. 22 illustrates a flow diagram of a Cas9-nickase library enrichment protocol.

FIG. 22 illustrates a flow diagram of a Cas9-nickase library enrichment protocol 2200. Library enrichment protocol 2200 may include, but is not limited to, the following steps.

At a step 2210, DNA (e.g., 50 ng) is input for library preparation and enrichment of targeted sequences. In one example, the DNA is lambda DNA as described with reference to FIG. 21. In another example, the DNA is human genomic DNA as described in more detail with reference to FIG. 24.

At a step 2215, the input DNA is tagmented. In one example, the lambda DNA is tagmented using a Nextera™ tagmented library preparation protocol (Illumina Inc.). After completion of the tagmentation reaction, the tagmented lambda DNA is purified using, for example, a Zymo Clean & Concentrator™ kit (Zymo Research).

At a step 2220, the tagmented DNA is amplified. In one example, the tagmented lambda DNA is amplified using 10 cycles of PCR amplification. Following PCR amplification of the tagmented lambda DNA, the amplified fragments are purified using, for example, an SPRI bead-based purification protocol (e.g., Ampure XP from Beckman).

At a step 2225, Cas9-nickase complexes are formed using crRNAs for each targeted DNA region, tracrRNA, and Cas9-nickase. In one example, the tracrRNA is unlabeled. In another example the tracrRNA is biotinylated. In one example, complex formation is performed at 48° C. In another example, complex formation is performed at 37° C.

At a step 2230, a magnetic bead-based pull-down reaction is performed to capture the targeted DNA sequences. In one example, biotinylated probes targeted to the displacement loop of each lambda DNA region in the Cas9-nickase complex and streptavidin coated magnetic beads are used to pull-down the targeted lambda DNA sequences. In another example, biotinylated tracrRNA sequences in the Cas9-nickase complex and streptavidin coated magnetic beads are used to pull-down the targeted lambda DNA sequences. After the bead-based pull-down reaction, the beads and Cas9-nickase complexes thereon are washed using a bead-based wash protocol.

At a step 2235, targeted DNA sequences bound to the streptavidin coated magnetic beads via Cas9-nickase complexes are amplified. In one example, the targeted lambda DNA sequences are amplified using 15 to 20 cycles of PCR amplification. After the bead-based amplification of targeted lambda DNA sequences, an SPRI bead-based purification protocol (e.g., Ampure XP) is used to purify and elute the targeted lambda DNA sequences. In one example, the targeted lambda DNA sequences are eluted using 8 µL of elution buffer.

At a step 2240, the isolated targeted DNA sequences are sequenced. In one example, sequencing is performed using a MiSeq system (Illumina Inc.). Library enrichment protocol 2200 ends.

Figure 23:
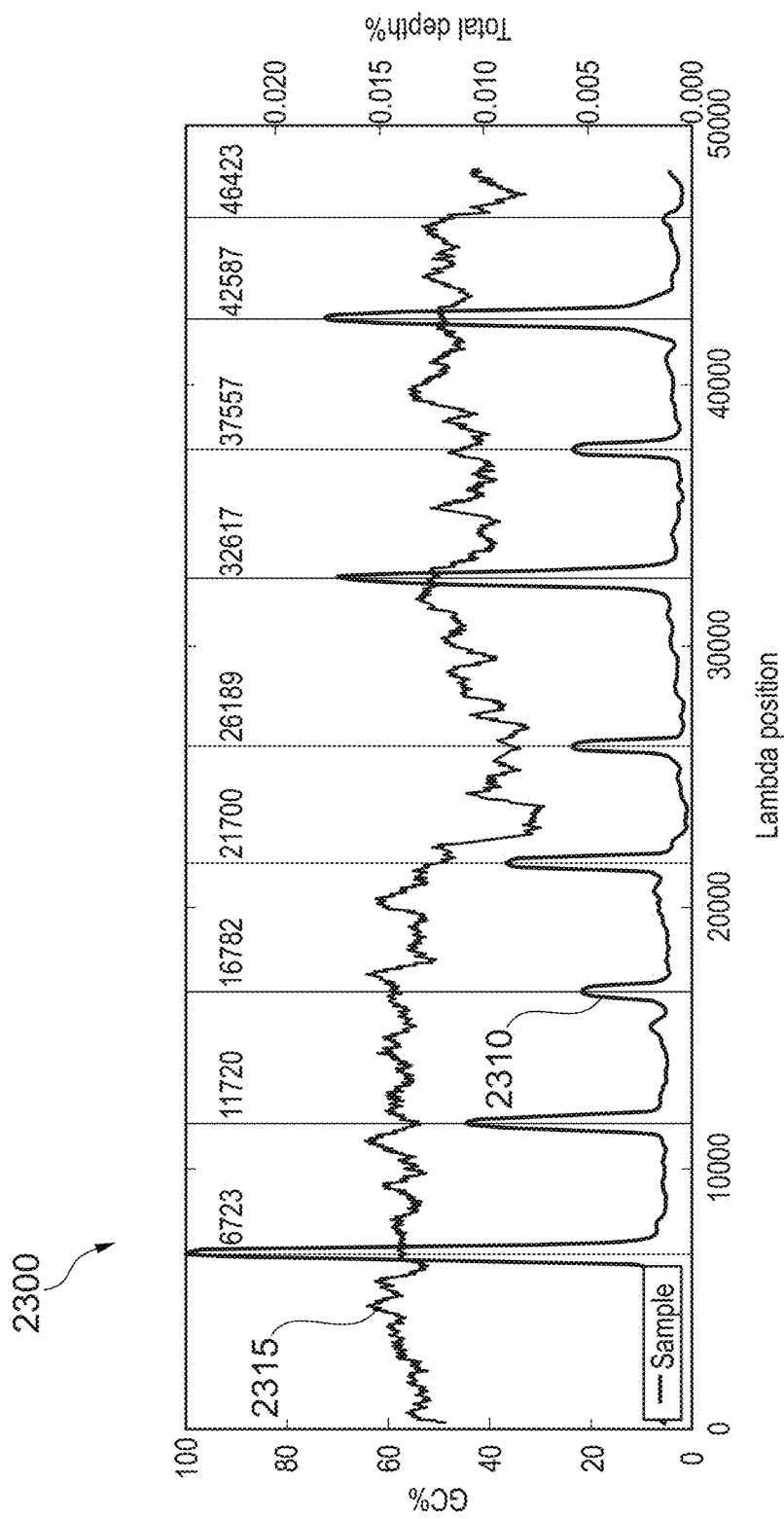
FIG. 23 shows a plot of the percent total depth and percent GC content as a function of position in the lambda genome for a lambda DNA enrichment library prepared using the library enrichment protocol of FIG. 22.

FIG. 23 shows a plot 2300 of the percent total depth and percent GC content as a function of position in the lambda genome for a lambda DNA enrichment library prepared using library enrichment protocol 2200 of FIG. 22. In this example, the Cas9-nickase complex formation and bead-washing protocol steps were performed using 500 mM NaCl and an incubation temperature of 48° C. Biotinylated probes targeted to the displacement loops of each targeted lambda DNA region in the Cas9-D10A nickase complex were used to pull-down the complexes. Plot 2300 shows a line 2310 of the percent total depth for each targeted region and a line 2315 of the percent GC content as a function of position in the lambda genome. The data show significant enrichment for 8 of the 9 targeted lambda regions. The data also show that the different targeted regions show different percentages of enrichment. The variability in target enrichment may be due, for example, to sequence differences or other parameters such as secondary structure of crRNAs or number of off-target sequences with high similarity to a crRNA. The data also show that the observed enrichment is real and not just a function of GC content.

Figure 24:
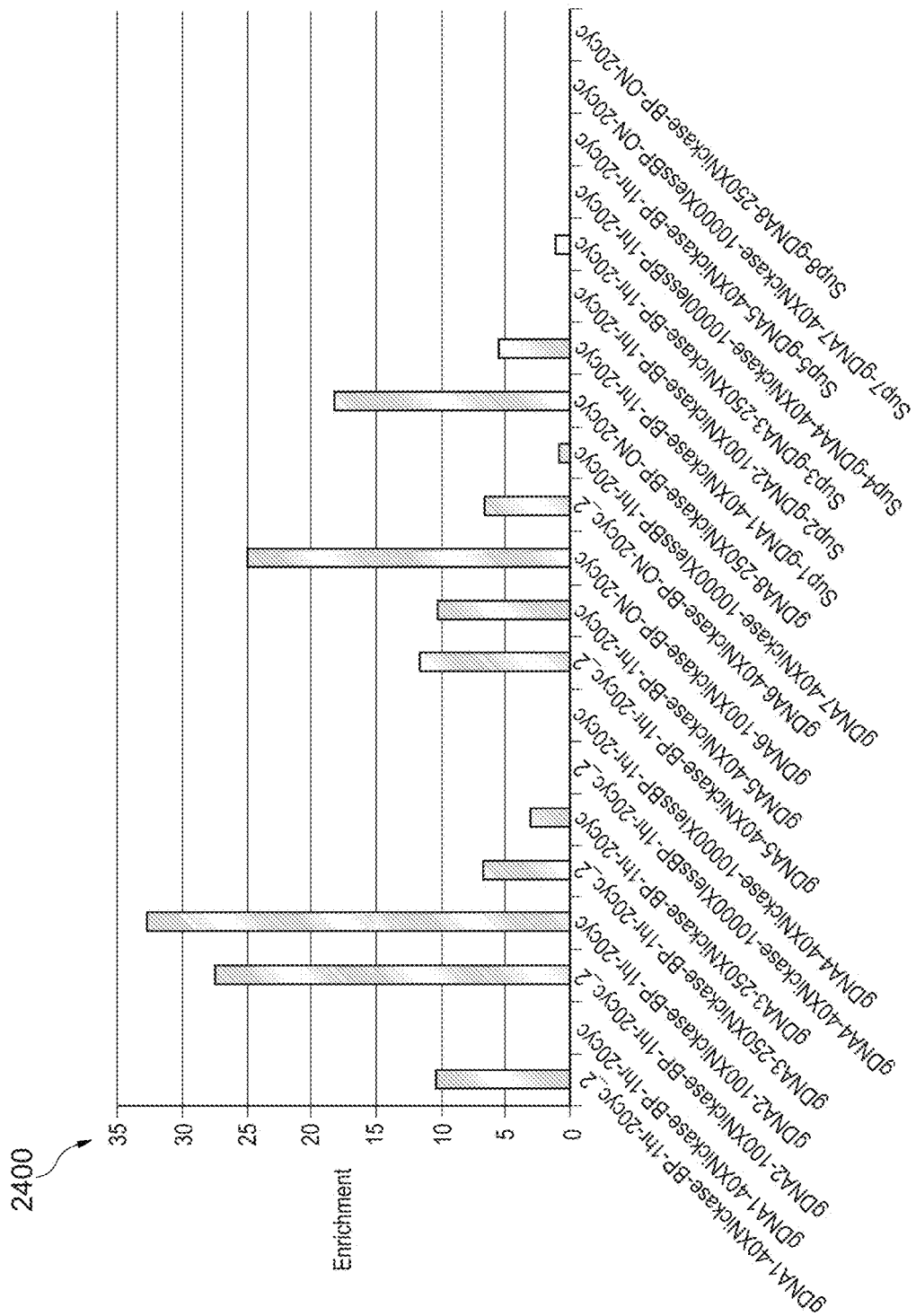
FIG. 24 shows a bar graph of the enrichment of an endogenous BRAF DNA sequence in genomic libraries prepared using the library enrichment protocol of FIG. 22.

FIG. 24 shows a bar graph 2400 of the enrichment of an endogenous BRAF DNA sequence in human genomic libraries prepared using library enrichment protocol 2200 of FIG. 22. In this example, 40×, 100×, or 250× molar excess of Cas9-nickase to genomic DNA (50 ng genomic DNA) were used to form Cas9-nickase complexes (step 2225 of library enrichment protocol 2200). Cas9-nickase complex formation was performed using 500 mM NaCl, an incubation temperature of 48° C. and either a 1 hour or overnight (ON) incubation ("binding time"). Pull-down of Cas9-nickase complexes (step 2230 of library enrichment protocol 2200) was performed using different concentrations of a biotinylated probe specific to the targeted BRAF DNA sequence and a 45 minute incubation period. After the pull-down reaction, the beads and Cas9-nickase complexes thereon are washed for 70 minutes at 48° C. using 1× CutSmart buffer containing 500 mM NaCl. Targeted BRAF DNA sequences were amplified (step 2235 of library enrichment protocol 2200) using 20 cycles of PCR. After the bead-based amplification of targeted BRAF DNA sequences, an SPRI bead-based purification protocol was used to purify and elute (8 µL elution volume) the targeted BRAF DNA sequences. Sequencing (step 2240 of library enrichment protocol 2200) was performed using a MiSeq system. Each bar on the graph represents a library. Libraries are designated by "gDNA-Nickase-biotinylated probe (BP)-binding time-PCR cycles". For example, the first bar in bar graph 2400 is labeled "gDNA1-40×Nickase-BP-1 hr-20cyc_2" and designates a library that was prepared using 40× molar excess of Cas9-nickase to the DNA library, 40× molar excess of biotinylated probe, a binding time (complex formation time) of 1 hour, and 20 cycles of bead-based PCR amplification. The data show that libraries prepared using 100×Cas9-nickase, 100× biotinylated probe, a 1 hour binding time (complex formation), and 20 cycles of bead-based PCR amplification have the highest level of target enrichment (i.e., library "gDNA2-100×Nickase-BP-1 hr-20cyc"). The left part of the graph is from bead elutions and the right part of the graph with Sup1, Sup2 designations is from supernatants after pull down (enrichment). gDNA1,gDNA2 etc. designate libraries prepared from the same human gDNA sample but with different dual indexes (Nextera Sample Prep protocol) for sequencing on a MiSeq instrument.

Figure 25:
FIG. 25 shows a data table of an example of the crRNA design for HindIII digested lambda DNA and forward and reverse strands for an IVT reaction for crRNA synthesis.

FIG. 25 shows a data table 2500 of an example of the crRNA design for HindIII digested lambda DNA and forward and reverse strands for an IVT reaction for crRNA synthesis.

What is claimed:

1. A method for enriching a target nucleic acid from a population of cell free DNAs (cfDNAs) comprising:
   obtaining a population of cfDNAs from a subject's plasma or serum, the population of cfDNAs containing the target nucleic acid;
   providing an endonuclease system having:
      a clustered regularly interspaced short palindromic repeats (CRISPR) RNA (crRNA), and
      a CRISPR-associated (Cas) protein,
      wherein the crRNA contains a target-specific nucleotide region complementary to a region of the target nucleic acid;
   contacting the target nucleic acid with the endonuclease system to form a complex,
      wherein the crRNA in the complex formed by the endonuclease system is labeled with a binding tag; and
   separating the complex from the population of cfDNAs using the binding tag, thereby enriching for the target nucleic acid.

2. The method of claim 1, further comprising separating the target nucleic acid from the complex.

3. The method of claim 2, further comprising amplifying the targeted nucleic acid.

4. The method of claim 1, wherein the endonuclease system further comprises a trans-activating crRNA (tracrRNA).

5. The method of claim 1, wherein the crRNA is a polynucleotide comprising a crRNA polynucleotide fused to a tracrRNA polynucleotide.

6. The method of claim 1, wherein the endonuclease system is a Type II CRISPR-Cas system.

7. The method of claim 1, wherein the target nucleic acid is a double-stranded DNA (dsDNA).

8. The method of claim 1, wherein the binding tag is biotin.

9. The method of claim 8, wherein streptavidin coated beads are used to bind to the biotin binding tag of the complex, thereby separating the complex from the population of cfDNAs.

10. The method of claim 1, wherein the Cas protein is a Cas9 protein.

11. The method of claim 10, wherein the Cas9 protein retains two nuclease domains and is able to produce a double-stranded DNA break.

12. The method of claim 10, wherein the Cas9 protein contains one inactivated nuclease domain comprising a mutation in the domain that cleaves a target nucleic acid strand that is complementary to the crRNA.

13. The method of claim 12, wherein said mutation is D10A.

14. The method of claim 10, wherein the Cas 9 protein contains one inactivated nuclease domain comprising a mutation in the domain that cleaves a target nucleic acid strand that is non-complementary to the crRNA.

15. The method of claim 14, wherein said mutation is H840A.

16. The method of claim 10, wherein the Cas9 protein contains two inactivated nuclease domains.

17. The method of claim 16, wherein the two inactivated nuclease domains comprise a first mutation in the domain that cleaves the strand complementary to the crRNA and a second mutation in the domain that cleaves the strand non-complementary to the crRNA.

18. The method of claim 17, wherein said first mutation is D10A and said second mutation is H840A.

19. The method of claim 1, wherein the entire crRNA is labeled with a binding tag by using in vitro transcription to incorporate one or more biotinylated nucleotides into the crRNA.

* * * * *

UNITED STATES PATENT AND TRADEMARK OFFICE
CERTIFICATE OF CORRECTION

PATENT NO. : 10,457,969 B2
APPLICATION NO. : 14/804068
DATED : October 29, 2019
INVENTOR(S) : Gordon M. Cann et al.

Page 1 of 1

It is certified that error appears in the above-identified patent and that said Letters Patent is hereby corrected as shown below:

On the Title Page

In Item (56) References Cited, in OTHER PUBLICATIONS, Column 2, Line 3, please replace "Imnunoprecipitation" with --Immunoprecipitation--

In Item (56) References Cited, in OTHER PUBLICATIONS, Column 2, Line 8, please replace "inmunoprecipitation" with --immunoprecipitation--

In Item (56) References Cited, in OTHER PUBLICATIONS, Column 2, Line 12, please replace "comple" with --complex--

Signed and Sealed this
Twenty-fifth Day of August, 2020

Andrei Iancu
*Director of the United States Patent and Trademark Office*